US012023500B2

(12) United States Patent
Osorio

(10) Patent No.: US 12,023,500 B2
(45) Date of Patent: Jul. 2, 2024

(54) CONTINGENT CARDIO-PROTECTION FOR EPILEPSY PATIENTS

(71) Applicant: Ivan Osorio, Leawood, KS (US)

(72) Inventor: Ivan Osorio, Leawood, KS (US)

(73) Assignee: Flint Hills Scientific, LLC, Lawrence, KS (US)

(*) Notice: Subject to any disclaimer, the term of this patent is extended or adjusted under 35 U.S.C. 154(b) by 0 days.

(21) Appl. No.: 18/118,966

(22) Filed: Mar. 8, 2023

(65) Prior Publication Data

US 2023/0241389 A1  Aug. 3, 2023

Related U.S. Application Data

(60) Continuation of application No. 16/690,452, filed on Nov. 21, 2019, now Pat. No. 11,607,547, which is a
(Continued)

(51) Int. Cl.
*A61N 1/05* (2006.01)
*A61N 1/36* (2006.01)

(52) U.S. Cl.
CPC ..... *A61N 1/36064* (2013.01); *A61N 1/36053* (2013.01); *A61N 1/36114* (2013.01); *A61N 1/36139* (2013.01); *A61N 1/36185* (2013.01); *A61N 1/0556* (2013.01); *A61N 1/36117* (2013.01)

(58) Field of Classification Search
CPC ............ A61N 1/36064; A61N 1/36053; A61N 1/36114; A61N 1/36139; A61N 1/36185; A61N 1/0556; A61N 1/36117; A61N 1/36007; A61N 1/36071; A61N 1/36082; A61N 1/36135; A61N 1/0456; A61N 1/0553; A61N 1/36017; A61N 1/37211; A61N 1/0502; A61N 1/0504; A61N 1/0529; A61N 1/3606; A61N 1/36067; A61N 1/361; A61N 1/36103; A61N 1/36107; A61N 1/37514; A61N 2/006; A61N 2/02; A61N 1/0472; A61N 1/0531; A61N 1/0534; A61N 1/0539; A61N 1/0551; A61N 1/36021; A61N 1/36025; A61N 1/36096; A61N 1/36132; A61N 1/36146; A61N 1/3756; A61B 5/4094; A61B 5/4836; A61B 5/0031
See application file for complete search history.

(56) References Cited

U.S. PATENT DOCUMENTS

| 2003/0083716 A1* | 5/2003 | Nicolelis ............ A61N 1/36064 607/45 |
| 2007/0093870 A1* | 4/2007 | Maschino .......... A61N 1/36085 607/2 |

* cited by examiner

*Primary Examiner* — Carl H Layno
*Assistant Examiner* — Anh-Khoa N Dinh
(74) *Attorney, Agent, or Firm* — CF3; Stephen Eisenmann

(57) ABSTRACT

A method of treating a medical condition in a patient using an implantable medical device, the implantable medical device including a first electrode coupled to a first cranial nerve structure and a second electrode coupled to a second cranial nerve structure, the method comprising: providing a first electrical signal to the first cranial nerve structure of the patient;
providing a second electrical signal to the second cranial nerve structure of the patient; administering to the patient a responsiveness test and comparing a result of the responsiveness test to a baseline responsiveness test; and initiating a second therapy or issuing a warning based on the comparison of the result of the responsiveness test to the baseline responsiveness test.

14 Claims, 35 Drawing Sheets

Related U.S. Application Data continuation-in-part of application No. 15/437,155, filed on Feb. 20, 2017, now Pat. No. 10,682,515, which is a division of application No. 14/050,173, filed on Oct. 9, 2013, now Pat. No. 9,579,506, which is a continuation-in-part of application No. 13/601,099, filed on Aug. 31, 2012, now Pat. No. 9,314,633, said application No. 16/690,452 is a continuation-in-part of application No. 12/756,065, filed on Apr. 7, 2010, said application No. 13/601,099 is a continuation-in-part of application No. 12/020,097, filed on Jan. 25, 2008, now Pat. No. 8,565,867, and a continuation-in-part of application No. 12/020,195, filed on Jan. 25, 2008, now Pat. No. 8,260,426.

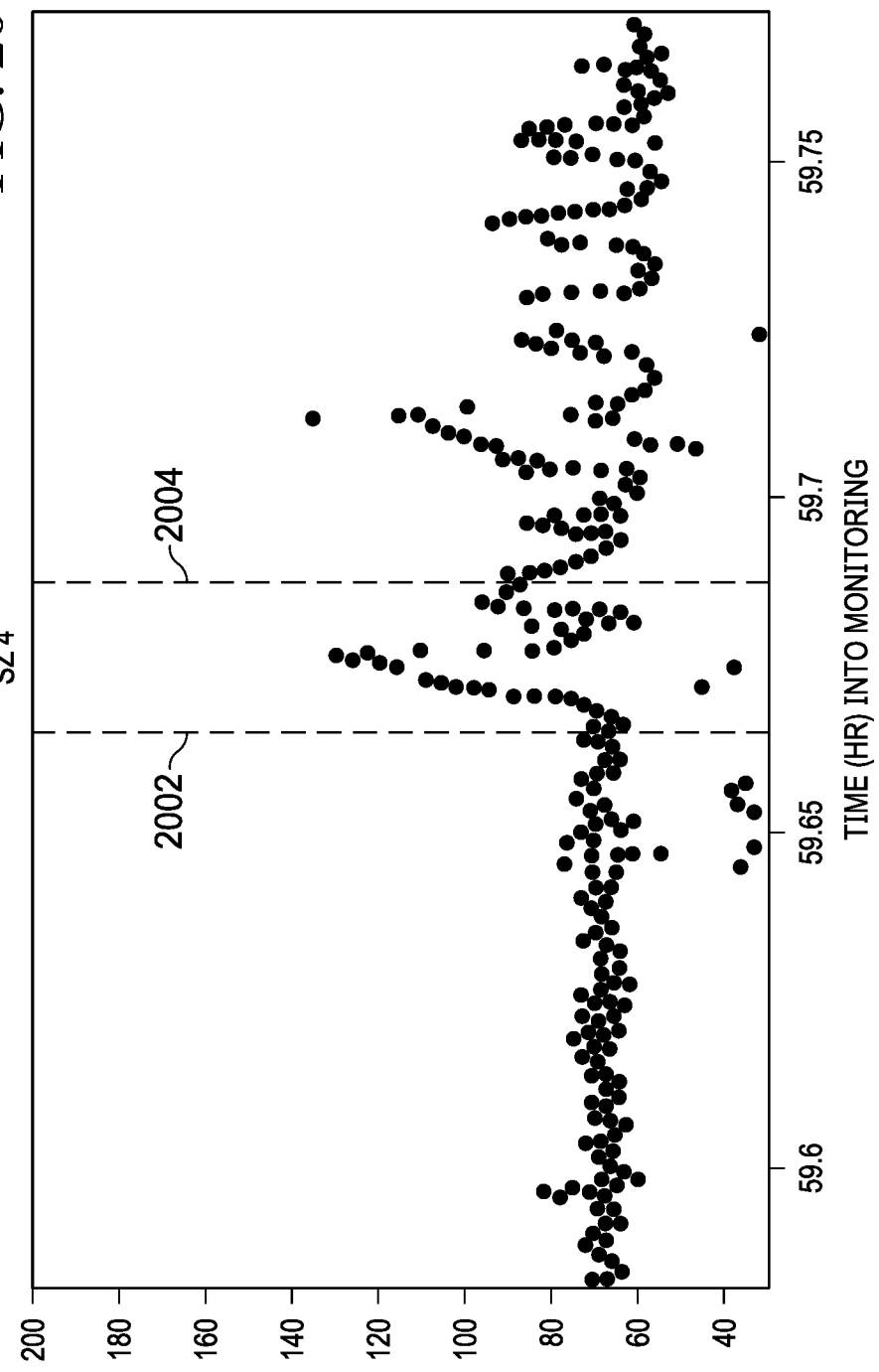

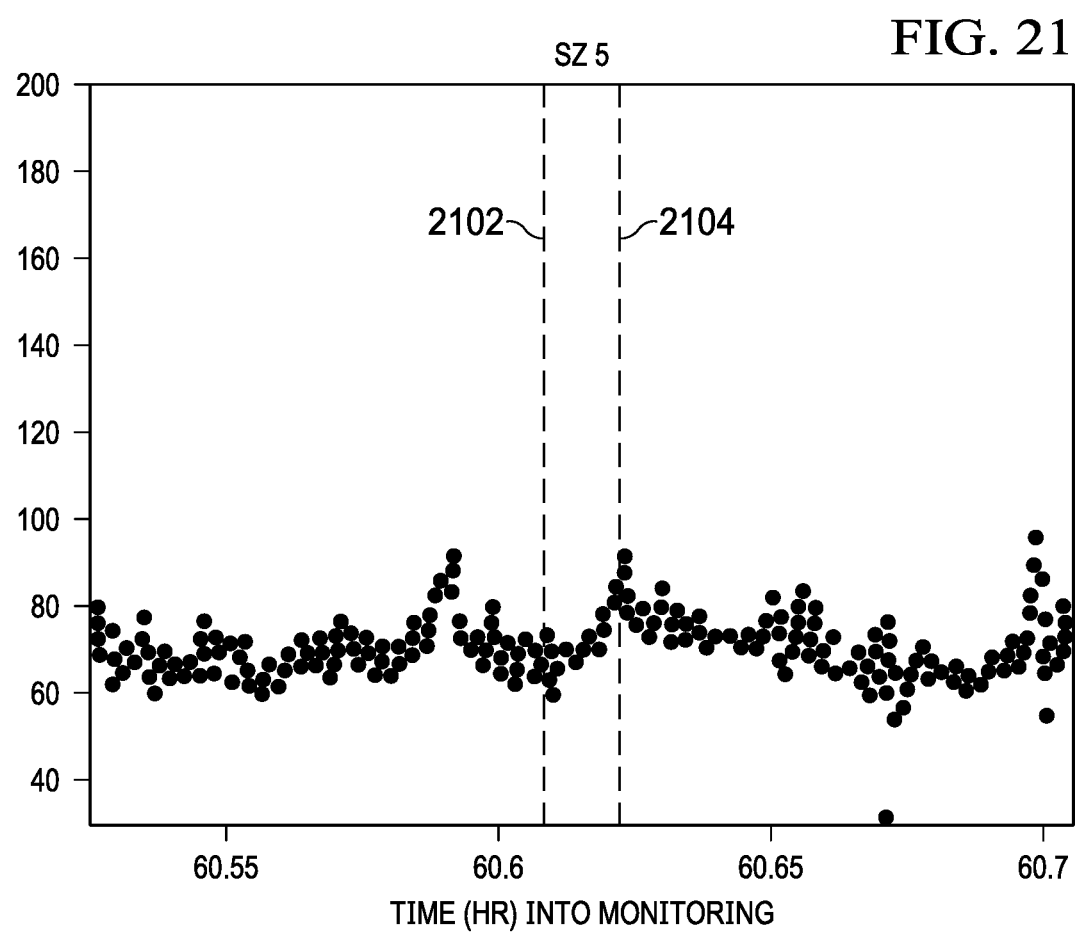

CONTINGENT CARDIO-PROTECTION FOR EPILEPSY PATIENTS

CROSS-REFERENCE TO RELATED APPLICATIONS

This presently being filed application is a continuation of and claims priority to U.S. patent application Ser. No. 16/690,452 entitled "Contingent Cardio-Protection for Epilepsy Patients", filed on Nov. 21, 2019 (now U.S. Pat. No. 11,607,547), which claims priority to and is a continuation-in-part of and claims priority to co-pending U.S. patent application Ser. No. 12/756,065 entitled "Responsiveness Testing of a Patient Having Brain State Changes", filed on Apr. 7, 2010 and U.S. patent application Ser. No. 16/690,452 is also a continuation-in-part of and claims priority to U.S. patent application Ser. No. 15/437,155 entitled "Contingent Cardio-Protection For Epilepsy Patients", filed on Feb. 20, 2017 (now U.S. Pat. No. 10,682,515), U.S. patent application Ser. No. 15/437,155 claims priority to and is a divisional application of U.S. patent application Ser. No. 14/050,173 entitled "Contingent Cardio-Protection For Epilepsy Patients", filed on Oct. 9, 2013 (now U.S. Pat. No. 9,579,506), which claims priority to and is a continuation-in-part of U.S. patent application Ser. No. 13/601,099 entitled "Contingent Cardio-Protection For Epilepsy Patients", filed on Aug. 31, 2012 (now U.S. Pat. No. 9,314,633), which claims priority to and is a continuation-in-part of U.S. patent application Ser. No. 12/020,195 entitled "Method, Apparatus and System for Bipolar Charge Utilization during Stimulation by an Implantable Medical Device", filed on Jan. 25, 2008 (now U.S. Pat. No. 8,260,426) and claims priority to and is a continuation-in-part of U.S. patent application Ser. No. 12/020,097 entitled "Changeable Electrode Polarity Stimulation by an Implantable Medical Device", filed on Jan. 25, 2008 (now U.S. Pat. No. 8,565,867) all of which are incorporated herein by reference in their entireties.

BACKGROUND OF THE DISCLOSURE

This disclosure relates generally to medical devices, and, more particularly, to methods, apparatus, and systems for performing vagus nerve stimulation (VNS) for treating epileptic seizures characterized by cardiac changes, including ictal tachycardia.

DESCRIPTION OF THE RELATED ART

While seizures are the best known and most studied manifestation of epilepsy, cardiac alterations are prevalent and may account for the high rate of sudden unexpected death (SUDEP) in these patients. These alterations may include changes in rate (most commonly tachycardia, rarely bradycardia or asystole), rhythm (PACs, PVCs,), conduction (e.g., bundle branch block) and repolarization abnormalities (e.g., Q-T prolongation, which occurs primarily during (ictal) but also between seizures (inter-ictally). In addition, S-T segment depression (a sign of myocardial ischemia) is observed during epileptic seizures. Significant elevations in heart-type fatty acid binding protein (H-FABP), a cytoplasmic low-molecular weight protein released into the circulation during myocardial injury have been documented in patients with epilepsy and without evidence of coronary artery disease, not only during seizures but also during free-seizure periods. H-FABP is a more sensitive and specific marker of myocardial ischemia than troponin I or CK-MB. Elevations in H-FABP appear to be un-correlated with duration of illness, of the recorded seizures, or with the Chalfont severity score of the patients.

The cardiac alterations in epilepsy patients, both during and between seizures, have a multi-factorial etiology, but a vago-sympathetic imbalance seems to play a prominent role in their generation. The majority of epileptic seizures enhance the sympathetic tone (plasma noradrenaline and adrenaline rise markedly after seizure onset) causing tachycardia, arterial hypertension and increases in the respiratory rate, among others. Recurrent and frequent exposure to the outpouring of catecholamines associated with seizures in patients with pharmaco-resistant epilepsies may, for example, account for abnormalities that increase the risk of sudden death such as prolongation of the Q-T interval which leads to often fatal tachyarrhythmias such as torsade de pointe. Further evidence in support of the role of catecholamines in SUDEP is found in autopsies of SUDEP victims, revealing interstitial myocardial fibrosis (a risk factor for lethal arrhythmias), myocyte vacuolization, atrophy of cardiomyocytes, leukocytic infiltration, and perivascular fibrosis. Restoration of the sympathetic-parasympathetic tone to normal levels, a therapeutic objective that may be accomplished by enhancing parasympathetic activity through among others, electrical stimulation of the vagus nerve, may decrease the rate and severity of cardiac and autonomic co-morbidities in these patients.

While there have been significant advances over the last several decades in treatments for epileptic seizures, the management of co-morbidities—in particular the cardiac alterations associated with seizures-remains largely unaddressed. There is a need for improved epilepsy treatments that address cardiac impairments associated with seizures. Pharmacological therapies for neurological diseases (including epilepsy) have been available for many decades. A more recent treatment for neurological disorders involves electrical stimulation of a target tissue to reduce symptoms or effects of the disorder. Such therapeutic electrical signals have been successfully applied to brain, spinal cord, and cranial nerves tissues improve or ameliorate a variety of conditions. A particular example of such a therapy involves applying an electrical signal to the vagus nerve to reduce or eliminate epileptic seizures, as described in U.S. Pat. Nos. 4,702,254, 4,867,164, and 5,025,807, which are hereby incorporated herein by reference in their entirety.

The endogenous electrical activity (i.e., activity attributable to the natural functioning of the patient's own body) of a neural structure may be modulated in a variety of ways. One such way is by applying exogenous (i.e., from a source other than the patient's own body) electrical, chemical, or mechanical signals to the neural structure. In some embodiments, the exogenous signal ("neurostimulation" or "neuromodulation") may involve the induction of afferent action potentials, efferent action potentials, or both, in the neural structure. In some embodiments, the exogenous (therapeutic) signal may block or interrupt the transmission of endogenous (natural) electrical activity in the target neural structure. Electrical signal therapy may be provided by implanting an electrical device underneath the skin of a patient and delivering an electrical signal to a nerve such as a cranial nerve.

In one embodiment, the electrical signal therapy may involve detecting a symptom or event associated with the patient's medical condition, and the electrical signal may be delivered in response to the detection. This type of stimulation is generally referred to as "closed-loop," "active," "feedback," "contingent" or "triggered" stimulation. Alternatively, the system may operate according to a predetermined program to periodically apply a series of electrical pulses to the nerve intermittently throughout the day, or over another predetermined time interval. This type of stimulation is generally referred to as "open-loop," "passive," "non-feedback," "non-contingent" or "prophylactic," stimulation.

In other embodiments, both open- and closed-loop stimulation modes may be used. For example, an open-loop electrical signal may operate as a "default" program that is repeated according to a programmed on-time and off-time until a condition is detected by one or more body sensors and/or algorithms. The open-loop electrical signal may then be interrupted in response to the detection, and the closed-loop electrical signal may be applied-either for a predetermined time or until the detected condition has been effectively treated. The closed-loop signal may then be interrupted, and the open-loop program may be resumed. Therapeutic electrical stimulation may be applied by an implantable medical device (IMD) within the patient's body or, in some embodiments, externally.

Closed-loop stimulation of the vagus nerve has been proposed to treat epileptic seizures. Many patients with intractable, refractory seizures experience changes in heart rate and/or other autonomic body signals near the clinical onset of seizures. In some instances the changes may occur prior to the clinical onset, and in other cases the changes may occur at or after the clinical onset. Where the changes involves heart rate, most often the rate increases, although in some instances a drop or a biphasic change (up-then-down or down-then-up) may occur. It is possible using a heart rate sensor to detect such changes and to initiate therapeutic electrical stimulation (e.g., VNS) based on the detected change. The closed-loop therapy may be a modified version of an open-loop therapy. See, e.g., U.S. Pat. Nos. 5,928,272, and 6,341,236, each hereby incorporated by reference herein. The detected change may also be used to warn a patient or third party of an impending or occurring seizure.

VNS therapy for epilepsy patients typically involves a train of electrical pulses applied to the nerve with an electrode pair including a cathode and an anode located on a left or right main vagal trunk in the neck (cervical) area. Only the cathode is capable of generating action potentials in nerve fibers within the vagus nerve; the anode may block some or all of the action potentials that reach it (whether endogenous or exogenously generated by the cathode). VNS as an epilepsy therapy involves modulation of one or more brain structures. Therefore, to prevent the anode from blocking action potentials generated by the cathode from reaching the brain, the cathode is usually located proximal to the brain relative to the anode. For vagal stimulation in the neck area, the cathode is thus usually the upper electrode and the anode is the lower electrode. This arrangement is believed to result in partial blockage of action potentials distal to or below the anode (i.e., those that would travel through the vagus nerve branches innervating the lungs, heart and other viscerae). Using an upper-cathode/lower-anode arrangement has also been favored to minimize any effect of the vagus nerve stimulation on the heart.

Stimulation of the left vagus nerve, for treatment of epilepsy has complex effects on heart rate (see Frei & Osorio, Epilepsia 2001), one of which includes slowing of the heart rate, while stimulation of the right vagus nerve has a more prominent bradycardic effect. Electrical stimulation of the right vagus nerve has been proposed for use in the operating room to slow the heart during heart bypass surgery, to provide a surgeon with a longer time period to place sutures between heartbeats (see, e.g., U.S. Pat. No. 5,651, 373). Some patents discussing VNS therapy for epilepsy treatment express concern with the risk of inadvertently slowing the heart during stimulation. In U.S. Pat. No. 4,702,254, it is suggested that by locating the VNS stimulation electrodes below the inferior cardiac nerve, "minimal slowing of the heart rate is achieved" (col. 7 lines 3-5), and in U.S. Pat. No. 6,920,357, the use of a pacemaker to avoid inadvertent slowing of the heart is disclosed.

Cranial nerve stimulation has also been suggested for disorders outside the brain such as those affecting the gastrointestinal system, the pancreas (e.g., diabetes, which often features impaired production of insulin by the islets of Langerhans in the pancreas), or the kidneys. Electrical signal stimulation of either the brain alone or the organ alone may have some efficacy in treating such medical conditions, but may lack maximal efficacy.

While electrical stimulation has been used for many years to treat a number of conditions, a need exists for improved VNS methods of treating epilepsy and its cardiac co-morbidities as well as other brain and non-brain disorders.

SUMMARY OF THE DISCLOSURE

In one aspect, the present disclosure relates to a method of treating a patient having epilepsy comprising receiving at least one body data stream, analyzing the at least one body data stream using a seizure or event detection algorithm to detect whether or not the patient is having and/or has had an epileptic seizure, receiving a cardiac signal of the patient, applying a first electrical signal to a vagus nerve of the patient based on a determination that the patient is not having and/or has not had an epileptic seizure characterized by a decrease in the patient's heart rate, wherein the first electrical signal is not a vagus nerve conduction blocking electrical signal, and applying a second electrical signal to a vagus nerve of the patient based on a determination that the patient is having and/or has had an epileptic seizure characterized by a decrease in the patient's heart rate, wherein the second electrical signal is a pulsed electrical signal that blocks action potential conduction in the vagus nerve.

In one aspect, the present disclosure relates to a method of treating a patient having epilepsy comprising sensing a cardiac signal and a kinetic signal of the patient, analyzing at least one of the cardiac signal and the kinetic signal; determining whether or not the patient has had an epileptic seizure based on the analyzing; in response to a determination that the patient has had an epileptic seizure, determining whether or not the seizure is characterized by a decrease in the patient's heart rate, applying a first electrical signal to a vagus nerve of the patient based on a determination that the patient has had an epileptic seizure characterized by a decrease in the patient's heart rate, wherein the first electrical signal is a pulsed electrical signal that blocks action potential conduction in the vagus nerve; and applying a second electrical signal to a vagus nerve of the patient based on one of a) a determination that the patient has not had an epileptic seizure, and b) a determination that the patient has had an epileptic seizure that is not characterized by a decrease in the patient's heart rate, wherein the second electrical signal is not a vagus nerve conduction blocking electrical signal.

In one aspect, the present disclosure relates to a system for treating a medical condition in a patient, comprising at least one electrode coupled to a vagus nerve of the patient, a programmable electrical signal generator, a sensor for sensing at least one body data stream, a seizure detection module capable of analyzing the at least one body data stream and determining, based on the analyzing, whether or not the patient is having and/or has had an epileptic seizure, a heart rate determination unit capable of determining a heart rate of a patient proximate in time to an epileptic seizure detected by the seizure detection module, and a logic unit for applying a first electrical signal to the vagus nerve using the at least one electrode based on a determination by the seizure detection module that the patient is having and/or has had an epileptic seizure characterized by a decrease in the patient's heart rate, wherein the first electrical signal is a pulsed electrical signal that blocks action potential conduction in the vagus nerve, and for applying a second electrical signal to the vagus nerve using the at least one electrode as a cathode based upon one of a) a determination that the patient is not having and/or has not had an epileptic seizure, and b) a determination that the patient is having and/or has had an epileptic seizure that is not characterized by a decrease in the patient's heart rate, wherein the second electrical signal is not a vagus nerve conduction blocking electrical signal. In one embodiment, the seizure detection module may comprise the heart rate determination unit.

In one aspect, the present disclosure relates to a method of treating a patient having epilepsy comprising applying a first electrical signal to a vagus nerve of the patient, wherein the first electrical signal is an open-loop electrical signal having a programmed on-time and a programmed off-time, sensing at least one body signal of the patient, determining the start of an epileptic seizure based on the at least one body signal, determining whether or not the seizure is characterized by a decrease in the patient's heart rate, applying a second, closed-loop electrical signal to a vagus nerve of the patient based on a determination that the epileptic seizure is not characterized by a decrease in the patient's heart rate, and applying a third, closed-loop electrical signal to a vagus nerve of the patient based on a determination that the seizure is characterized by a decrease in the patient's heart rate, wherein the third electrical signal is applied to block action potential conduction on the vagus nerve.

In one aspect, the present disclosure relates to a method of controlling a heart rate of an epilepsy patient comprising sensing a kinetic signal of the patient; analyzing said kinetic signal to determine at least one kinetic index; receiving a cardiac signal of the patient; analyzing the cardiac signal to determine the patient's heart rate; determining if the patient's heart rate is commensurate with the at least one kinetic index; and applying a first electrical signal to a vagus nerve of the patient based on a determination that the patient's heart rate is not commensurate with the kinetic index. In one embodiment, the at least one kinetic index comprises at least one of an activity level or an activity type of the patient, and determining if the heart rate is commensurate with the kinetic index comprises determining if the heart rate is commensurate with the at least one of an activity level or an activity type.

In one aspect, the present disclosure relates to a method of controlling a heart rate of an epilepsy patient comprising sensing at least one of a kinetic signal and a metabolic (e.g., oxygen consumption) signal of the patient; receiving a cardiac signal of the patient; analyzing the cardiac signal to determine the patient's heart rate; determining if the patient's heart rate is commensurate with the at least one of a kinetic and a metabolic signal of the patient; and applying a first electrical signal to a vagus nerve of the patient based on a determination that the patient's heart rate is not commensurate with the at least one of a kinetic signal and a metabolic signal. In one embodiment, the method further comprises determining at least one of an activity level or an activity type of the patient based on the at least one of a kinetic and a metabolic signal, and determining if the heart rate is commensurate with the kinetic signal comprises determining if the heart rate is commensurate with the at least one of an activity level or an activity type.

In one aspect, the present disclosure relates to a method of treating a patient having epilepsy comprising sensing at least one body signal of the patient; determining whether or not the patient is having or has had an epileptic seizure based on the at least one body signal; sensing a cardiac signal of the patient; determining whether or not the seizure is associated with a change in the patient's cardiac signal; applying a first therapy to a vagus nerve of the patient based on a determination that the patient is having or has had an epileptic seizure that is not associated with a change in the patient's cardiac signal, wherein the first therapy is selected from an electrical, chemical, mechanical (e.g., pressure) or thermal signal. The method further comprises applying a second therapy to a vagus nerve of the patient based on a determination that the patient has had an epileptic seizure associated with a change in the patient's cardiac signal, wherein the second therapy is selected from an electrical, chemical, mechanical (e.g., pressure) or thermal signal. In some embodiments, a third therapy may be applied to a vagus nerve based a determination that the patient has not had an epileptic seizure, wherein the third therapy is selected form an electrical, chemical, mechanical or thermal signal.

BRIEF DESCRIPTION OF THE DRAWINGS

The disclosure may be understood by reference to the following description taken in conjunction with the accompanying drawings, in which like reference numerals identify like elements, and in which:

FIG. 20 is a graph relating to the automated detection and control of ictal and peri-ictal chronotropic instability, according to one embodiment.

FIG. 21 is a graph relating to the automated detection and control of ictal and peri-ictal chronotropic instability, according to one embodiment.

Figure 1A:
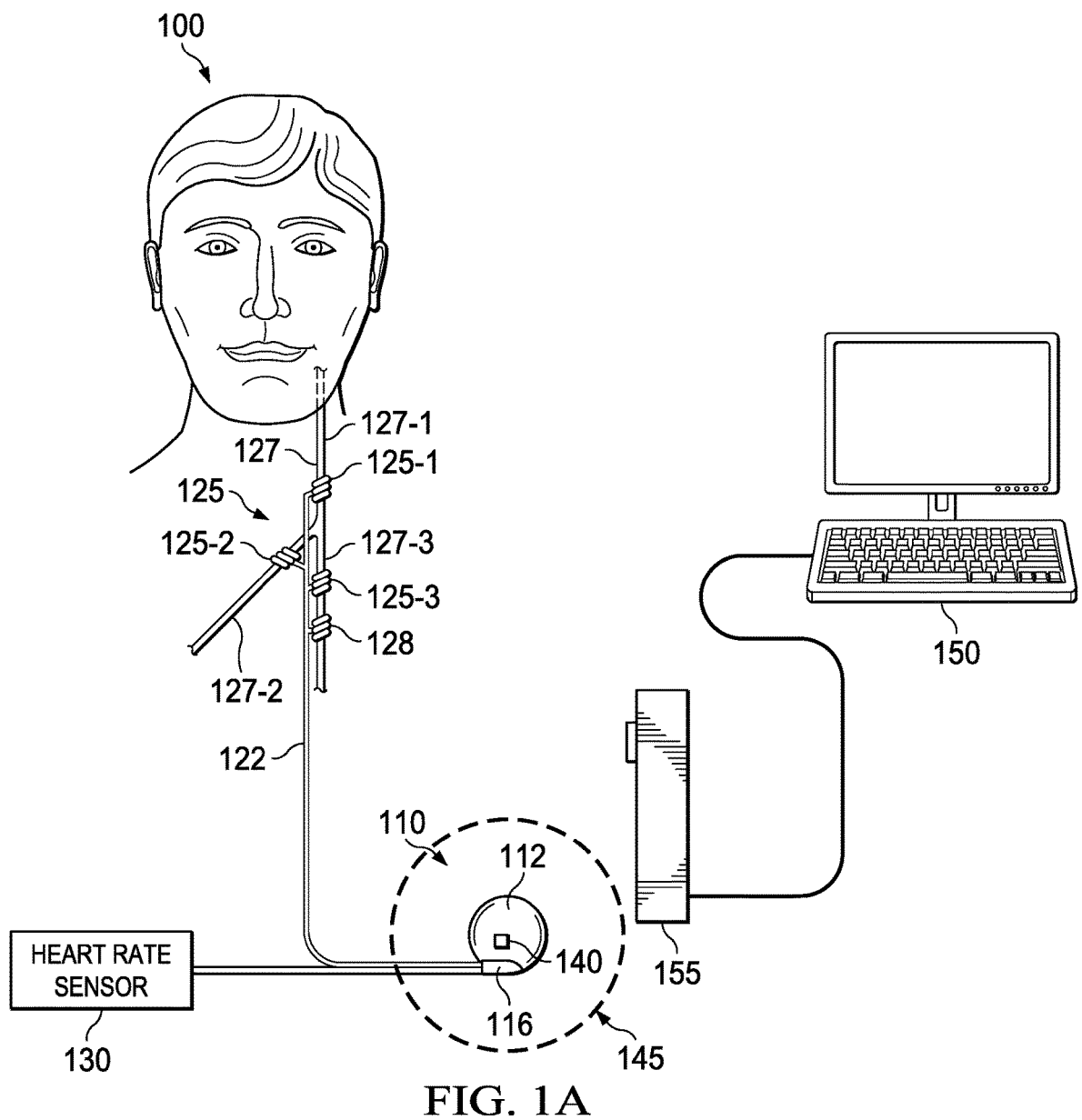
FIGS. 1A-1E provide stylized diagrams of an implantable medical device implanted into a patient's body for providing first and second electrical signals to a vagus nerve of a patient for treating epileptic seizures, in accordance with one illustrative embodiment of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are provided in detail. In any actual embodiment, numerous implementation-specific decisions must be made to achieve the design-specific goals. Such a development effort, while possibly complex and time-consuming, would nevertheless be a routine task for persons of skill in the art given this disclosure.

This application does not intend to distinguish between components that differ in name but not function. "Including" and "includes" are used in an open-ended fashion, and should be interpreted to mean "including, but not limited to." "Couple" or "couples" are intended to mean either a direct or an indirect electrical connection. "Direct contact," "direct attachment," or providing a "direct coupling" indicates that a surface of a first element contacts the surface of a second element with no substantial attenuating medium there between. Small quantities of substances, such as bodily fluids, that do not substantially attenuate electrical connections do not vitiate direct contact. "Or" is used in the inclusive sense (i.e., "and/or") unless a specific use to the contrary is explicitly stated.

"Electrode" or "electrodes" may refer to one or more stimulation electrodes (i.e., electrodes for applying an electrical signal generated by an IMD to a tissue), sensing electrodes (i.e., electrodes for sensing a body signal), and/or electrodes capable of either stimulation or sensing. "Cathode" and "anode" have their standard meanings, as the electrode at which current leaves the IMD system and the electrode at which current enters the IMD system, respectively. Reversing the polarity of the electrodes can be effected by any switching technique known in the art.

A "pulse" is used herein to refer to a single application of electrical charge from the cathode to target neural tissue. A pulse may include both a therapeutic portion (in which most or all of the therapeutic or action-potential-generating effect occurs) and a charge-balancing portion in which the polarity of the electrodes are reversed and the electrical current is allowed to flow in the opposite direction to avoid electrode and/or tissue damage. Individual pulses are separated by a time period in which no charge is delivered to the nerve, which can be called the "interpulse interval." A "burst" is used herein to refer to a plurality of pulses, which may be separated from other bursts by an interburst interval in which no charge is delivered to the nerve. The interburst intervals have a duration exceeding the interpulse interval duration. In one embodiment, the interburst interval is at least twice as long as the interpulse interval. The time period between the end of the last pulse of a first burst and the initiation of the first pulse of the next subsequent burst can be called the "interburst interval." In one embodiment, the interburst interval is at least 100 msec.

A plurality of pulses can refer to any of (a) a number of consecutive pulses within a burst, (b) all the pulses of a burst, or (c) a number of consecutive pulses including the final pulse of a first burst and the first pulse of the next subsequent burst.

"Stimulate," "stimulating" and "stimulator" may generally refer to applying a signal, stimulus, or impulse to neural tissue (e.g., a volume of neural tissue in the brain or a nerve) for affecting it neuronal activity. While the effect of such stimulation on neuronal activity is termed "modulation," for simplicity, the terms "stimulating" and "modulating", and variants thereof, are sometimes used interchangeably herein. The modulation effect of a stimulation signal on neural tissue may be excitatory or inhibitory, and may potentiate acute and/or long-term changes in neuronal activity. For example, the modulation effect of a stimulation signal may comprise: (a) initiating action potentials in the target neural tissue; (b) inhibition of conduction of action potentials (whether endogenous or exogenously generated, or blocking their conduction (e.g., by hyperpolarizing or collision blocking), (c) changes in neurotransmitter/neuromodulator release or uptake, and (d) changes in neuroplasticity or neurogenesis of brain tissue. Applying an electrical signal to an autonomic nerve may comprise generating a response that includes an afferent action potential, an efferent action potential, an afferent hyperpolarization, an efferent hyperpolarization, an afferent sub-threshold depolarization, and/or an efferent sub-threshold depolarization. The terms tachycardia and bradycardia are used here in a relative (i.e., any decrease or decrease in heart rate relative to a reference value) or in an absolute sense (i.e., a pathological change relative to a normative value). In particular, "tachycardia is used interchangeably with an increase heart rate and "bradycardia" may be used interchangeably with a decrease in heart rate.

A variety of stimulation therapies may be provided in embodiments of the present disclosure. Different nerve fiber types (e.g., A, B, and C-fibers that may be targeted) respond differently to stimulation from electrical signals because they have different conduction velocities and stimulation threshold. Certain pulses of an electrical stimulation signal, for example, may be below the stimulation threshold for a particular fiber and, therefore, may generate no action potential. Thus, smaller or narrower pulses may be used to avoid stimulation of certain nerve fibers (such as C-fibers) and target other nerve fibers (such as A and/or B fibers, which generally have lower stimulation thresholds and higher conduction velocities than C-fibers). Additionally, techniques such as a pre-pulse may be employed wherein axons of the target neural structure may be partially depolarized (e.g., with a pre-pulse or initial phase of a pulse) before a greater current is delivered to the target (e.g., with a second pulse or an initial phase such a stair step pre-pulse to deliver a larger quantum of charge). Furthermore, opposing polarity phases separated by a zero current phase may be used to excite particular axons or postpone nerve fatigue during long term stimulation.

Cranial nerve stimulation, such as vagus nerve stimulation (VNS), has been proposed to treat a number of medical conditions, including epilepsy and other movement disorders, depression and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the variety of disorders for which cranial nerve stimulation has been proposed or suggested, the fact that detailed neural pathways for many (if not all) cranial nerves remain relatively unknown, makes predictions of efficacy for any given disorder difficult or impossible. Even if such pathways were known, the precise stimulation parameters that would modulate particular pathways relevant to a particular disorder generally cannot be predicted.

Cardiac signals suitable for use in embodiments of the present disclosure may comprise one or more of an electrical (e.g., EKG), acoustic (e.g., phonocardiogram or ultrasound/ECHO), force or pressure (e.g., apexcardiogram), arterial pulse pressure and waveform or thermal signals that may be recorded and analyzed to extract features such as heart rate, heart rate variability, rhythm (regular, irregular, sinus, ventricular, ectopic, etc.), morphology, etc.

It appears that sympatho-vagal imbalance (lower vagal and higher sympathetic tone) plays an important role in generation of a wide spectrum of ictal and interictal alterations in cardiac dynamics, ranging from rare unifocal PVCs to cardiac death. Without being bound by theory, restoration of the vagal tone to a level sufficient to counteract the pathological effects of elevated catecholamines may serve a cardio-protective purpose that would be particularly beneficial in patients with pharmaco-resistant epilepsies, who are at highest risk for SUDEP.

In one embodiment, the present disclosure provides methods and apparatus to increase cardiac vagal tone in epilepsy patients by timely delivering therapeutic electrical currents to the trunks of the right or left vagus nerves or to their cardiac rami (branches), in response to increases in sympathetic tone, by monitoring among others, heart rate, heart rhythm, EKG morphology, blood pressure, skin resistance, catecholamine or their metabolites and neurological signals such as EEG/ECOG, kinetic (e.g., amplitude velocity, direction of movements) and cognitive (e.g., complex reaction time).

In one embodiment, the present disclosure provides a method of treating a medical condition selected from the group consisting of epilepsy, neuropsychiatric disorders (including but not limited to depression), eating disorders/obesity, traumatic brain injury, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, gastrointestinal disorders, kidney disorders, and reproductive endocrine disorders (including infertility).

Figure 1B:
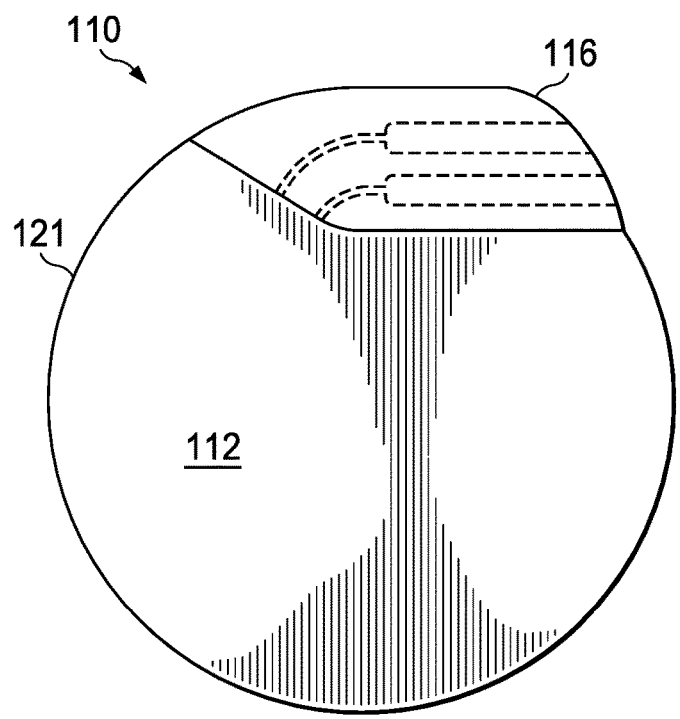

FIGS. 1A-1E depict a stylized implantable medical system 100 for implementing one or more embodiments of the present disclosure. FIGS. 1A and 1B illustrate an electrical signal generator 110 having main body 112 comprising a case or shell (commonly referred to as a "can") 121 (FIG. 1B) with a header 116 for connecting to a lead assembly 122. An electrode assembly 125, preferably comprising at least an electrode pair, is conductively connected to the distal end of an insulated, electrically conductive lead assembly 122, which preferably comprises a plurality of lead wires (at least one wire for each electrode of the electrode assembly 125). Lead assembly 122 is attached at its proximal end to one or more connectors on header 116 (FIG. 1B).

Electrode assembly 125 may be surgically coupled to a target tissue for delivery of a therapeutic electrical signal, which may be a pulsed electrical signal. The target tissue may be a cranial nerve, such as a vagus nerve 127 (FIGS. 1A, 1C-E) or another cranial nerve such as a trigeminal nerve. Electrode assembly 125 includes one or more electrodes 125-1, 125-2, 125-3, which may be coupled to the target tissue. The electrodes may be made from any of a variety of conductive metals known in the art, e.g., platinum, iridium, oxides of platinum or iridium, or combinations of the foregoing. In one embodiment, the target tissue is a vagus nerve 127, which may include an upper main trunk portion 127-1 above a cardiac branch 127-2, and a lower main trunk portion 127-3 below the cardiac branch.

Figure 1C:
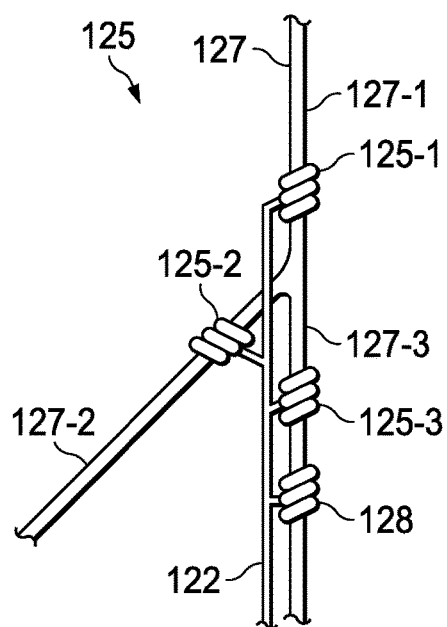

In one embodiment, at least one electrode may be coupled to the main trunk of the vagus nerve, and at least one electrode 125-2 may be coupled to a cardiac branch 127-2 of the vagus nerve (FIG. 1C). The at least one main trunk electrode may be coupled to an upper main trunk 127-1 (e.g., electrode 125-1, FIG. 1C) or a lower main trunk 127-3 (e.g., electrode 125-3). The at least one main trunk electrode (125-1, 125-3) may be used as a cathode to provide a first electrical signal to the upper (127-1) or lower (127-3) main trunk. Cardiac branch electrode 125-2 may be used as a cathode to provide a second electrical signal to cardiac branch 127-2. An additional electrode to function as the anode may be selected from one or more of the other electrodes in electrode assembly 125, can 121, or a dedicated anode.

In some embodiments (FIGS. 1D, 1E), electrode assembly 125 may include a main trunk electrode pair comprising a cathode 125-1a and an anode 125-1b for coupling to a main trunk of a vagus nerve 127. The main trunk electrode pair 125-1a, 125-1b may be coupled to an upper main trunk 127-1 of a vagus nerve (FIG. 1D), or to a lower main trunk 127-3 (FIG. 1E) for delivering a first electrical signal. Without being bound by theory, it is believed that few or no vagal afferent fibers in the lower main trunk 127-3 pass into cardiac branch 127-2 and, accordingly, that effects of the first electrical signal on cardiac function may be minimized by coupling electrode pair 125-1a and 125-1b to the lower main trunk 127-3 instead of upper main trunk 127-1. Cardiac effects may also be minimized by alternative embodiments in which the first electrical signal is applied to a lower main trunk 127-3 using a single electrode (e.g., 125-3, FIG. 1C) as a cathode and an anode that is not coupled to the vagus nerve 127 (e.g., by using can 121 as an anode).

In some embodiments (FIGS. 1D, 1E), electrode assembly 125 may include a cardiac branch electrode pair comprising a cathode 125-2a and an anode 125-2b for coupling to a cardiac branch of a vagus nerve. The second cardiac branch electrode pair may be used to provide a second electrical signal to a cardiac branch of the nerve to affect the cardiac function of the patient.

Referring again to FIGS. 1C-1E, a first electrical signal may be provided to generate afferent action potentials in a main trunk of a vagus nerve to modulate electrical activity of the patient's brain without significantly affecting the patient's heart rate. The second electrical signal may generate efferent action potentials to module the cardiac activity of the patient, and in particular to slow the patient's heart rate (e.g., to treat an epilepsy patient having seizures characterized by ictal tachycardia) and maintain or restore a sympathetic/parasympathetic balance to a non-pathological state. The first electrical signal may be applied to the main trunk of the vagus nerve in a variety of ways, so long as at least one electrode is coupled to the main trunk as a cathode. As noted, the cathode may be coupled to either an upper (127-1) or lower (127-3) main trunk, and an anode may be provided by any of the other electrodes on the vagus nerve (e.g., 125-1b, 125-2b, 125-3, FIGS. 1C-1E) or by a separate anode not coupled to the vagus nerve (e.g., can 121). In one alternative embodiment, an electrode 125-3 may be coupled to a lower main trunk 127-3 of the vagus nerve to function as an anode. In yet another embodiment, each individual electrode element in FIGS. 1A-E (e.g., 125-1, 125-2, 125-3, 125-1a, 125-1g, 125-2a, 125-2b) may comprise an electrode pair comprising both an anode and a cathode. In an additional embodiment, each individual electrode element may comprise three electrodes (e.g., one serving as cathode and the other two as anodes). Suitable electrode assemblies are available from Cyberonics, Inc., Houston, Texas, USA as the Model 302, PerenniaFlex and PerenniaDura electrode assemblies. In view of the present disclosure, persons of skill in the art will appreciate that many electrode designs could be used in embodiments of the present disclosure including unipolar electrodes.

Embodiments of the present disclosure may comprise electrical signals with either charge-balanced or non-charge-balanced pulses (e.g., monopolar/monophasic, direct current (DC)). Charge-balanced pulses involve a first phase in which the stimulation occurs (i.e., action potentials are induced in target nerve fibers), and a second phase in which the polarity of the electrodes are reversed (i.e., the stimulation phase cathode becomes the charge-balancing phase anode, and vice versa). The result is a pulse having two opposite-polarity phases of equal charge, such that no net charge flows across the electrode during a pulse. Charge-balancing is often used to avoid damage to the electrodes that may result if a pulse results in a net charge flowing across the electrodes.

In some instances, charge-balancing may involve a passive discharge phase as illustrated in, e.g., FIG. 1A of US Publication 2006/0173493, which is hereby incorporated by reference in its entirety. In passive charge-balancing, the charge-balancing phase typically involves allowing a capacitor having a charge equal to the charge applied to the nerve during the stimulation phase to discharge through the polarity-reversed electrodes. Passive charge-balancing typically uses much lower initial current than the stimulation phase, with the current declining to zero over a much longer time period than the pulse width of the stimulation phase. A lower current is typically selected in the charge-balancing phase so as to avoid or minimize nerve recruitment during the charge-balancing phase. In active charge-balancing, the charge-balancing phase is not accomplished by the passive discharge of a capacitor, but by providing a second phase having an opposite polarity but the same charge magnitude (pulse width multiplied by current) as the first phase. As is usually the case with passive charge-balancing, active charge-balancing typically involves a much lower current that is applied over a longer time period than the stimulation phase, so as to avoid nerve recruitment. In some instances, however, the active charge-balancing phase may be used as a second stimulation phase by selecting a current magnitude of the cathode in the charge-balancing phase (typically a second electrode, which may be the anode of the initial stimulation phase) that is sufficient to generate action potentials in nerve fibers of the target tissue.

Embodiments of the present disclosure may be implemented using passive charge balancing or active charge-balancing, and the latter may be provided as a stimulation phase or a non-stimulation phase. Some embodiments may be implemented with non-charge-balanced pulses. Persons of skill in the art, having the benefit of the present disclosure, may select the type of charge balancing (if desired) based upon a number of factors including but not limited to whether or not the charge-balancing is intended to affect the cardiac cycle or not, whether afferent or efferent stimulation is desired, the number and location of available electrodes for applying the electrical signal, the fibers intended to be recruited during a particular phase and their physiological effects, among many other factors.

In the discussion of electrical signals in the present disclosure, unless otherwise stated, references to electrodes as cathodes or anodes refers to the polarities of the electrodes during a stimulation phase of a pulse, whether the pulse is a charge-balanced pulse or a non-charge-balanced pulse (e.g., monopolar/monophasic or DC). It will be appreciated that where charge-balanced pulses are employed, the polarities will be reversed during a charge-balancing phase. Where active charge-balancing is used, cardiac effects may be further amplified or ameliorated, depending upon the location of the electrodes being used.

Returning to FIG. 1A, in some embodiments, a heart rate sensor 130, and/or a kinetic sensor 140 (e.g., a triaxial accelerometer) may be included in the system 100 to sense one or more of a cardiac signal or data stream and a kinetic data stream of the patient. In one embodiment, the heart rate sensor may comprise a separate element 130 that may be coupled to generator 110 through header 116 as illustrated in FIG. 1A. In another embodiment, the electrodes 125-1, 125-2, 125-3 and/or the can 121 may be used as sensing electrodes to sense heart rate. An accelerometer may be provided inside generator 110 in one embodiment to sense a kinetic signal (e.g., body movement) of the patient. One or more of the heart rate sensor 130 and the kinetic sensor 140 may be used by a seizure detection algorithm in the system 100 to detect epileptic seizures. In alternative embodiments, other body signals (e.g., blood pressure, brain activity, blood oxygen/$CO_2$ concentrations, temperature, skin resistivity, etc.) of the patient may be sensed and used by the seizure detection algorithm to detect epileptic seizures. Signal generator 110 may be implanted in the patient's chest in a pocket or cavity formed by the implanting surgeon below the skin (indicated by line 145, FIG. 1A).

Returning to FIGS. 1A and 1C, a first electrode 125-1 may be wrapped or otherwise electrically coupled to an upper main trunk 127-1 of a vagus nerve 127 of the patient, and a second electrode 125-2 may be wrapped or coupled to a cardiac branch 127-2 of the vagus nerve. In one embodiment, a third electrode 125-3 may be coupled to a lower main trunk 127-3 of the vagus nerve below the cardiac branch 127-2 of the vagus nerve, instead of or in addition to first electrode 125-1 coupled to the upper main trunk above the cardiac branch. In some embodiments, third electrode 125-3 may be omitted. Electrode assembly 125 may be secured to the nerve by a spiral anchoring tether 128 (FIG. 1C), which in one embodiment does not include an electrode but in alternative embodiments may contain up to three electrodes that serve as cathode(s) and anode(s) in any possible combination. Lead assembly 122 may further be secured, while retaining the ability to flex, by a suture connection 130 to nearby tissue (FIG. 1C). In particular embodiments, any of first, second and third electrodes 125-1, 125-2, and 125-3 may be used as either a cathode or as an anode. In general, the foregoing electrodes may be used as a cathode when the particular electrode is the closest electrode (among a plurality of electrodes) to the target organ (e.g., heart, brain, stomach, liver, etc.) to be stimulated. While a single electrode (e.g., 125-1, 125-2, or 125-3) is illustrated in connection with upper main trunk 127-1, cardiac branch 127-2, and lower main trunk 127-3 in FIGS. 1A and 1C for simplicity, it will be appreciated that one or more additional electrodes can be provided on each of the foregoing neural structures to provide greater flexibility in stimulation.

In one embodiment, the open helical design of the electrodes 125-1, 125-2, 125-3, is self-sizing, flexible, minimize mechanical trauma to the nerve and allow body fluid interchange with the nerve. The electrode assembly 125 preferably conforms to the shape of the nerve, providing a low stimulation threshold by allowing a large stimulation contact area with the nerve. Structurally, the electrode assembly 125 comprises an electrode ribbon (not shown) for each of electrodes 125-1, 125-2, 125-3, made of a conductive material such as platinum, iridium, platinum-iridium alloys, and/or oxides thereof. The electrode ribbons are individually bonded to an inside surface of an elastomeric body portion of the spiral electrodes 125-1, 125-2, 125-3 (FIG. 1C), which may comprise spiral loops of a multi-loop helical assembly. Lead assembly 122 may comprise three distinct lead wires or a triaxial cable that are respectively coupled to one of the conductive electrode ribbons. One suitable method of coupling the lead wires to the electrodes 125-1, 125-2, 125-3 comprises a spacer assembly such as that disclosed in U.S. Pat. No. 5,531,778, although other known coupling methods may be used.

The elastomeric body portion of each loop may be composed of silicone rubber or other biocompatible elastomeric compounds, and the fourth loop 128 (which may have no electrode in some embodiments) acts as the anchoring tether for the electrode assembly 125.

In one embodiment, electrical pulse generator 110 may be programmed with an external computer 150 using programming software known in the art for stimulating neural structures, and a programming wand 155 to facilitate radio frequency (RF) communication between the external computer 150 (FIG. 1A) and the implanted pulse generator 110. In one embodiment, wand 155 and software permit wireless, non-invasive communication with the generator 110 after surgical implantation. Wand 155 may be powered by internal batteries, and provided with a "power on" light to indicate sufficient power for communications. Another indicator light may be provided to show that data transmission is occurring between the wand and the generator. In other embodiments, wand 155 may be omitted, e.g., where communications occur in the 401-406 MHz bandwidth for Medical Implant Communication Service (MICS band).

In some embodiments of the disclosure, a body data stream may be analyzed to determine whether or not a seizure has occurred. Many different body data streams and seizure detection indices have been proposed for detecting epileptic seizures. Additional details on method of detecting seizure from body data are provided in U.S. Pat. Nos. 8,337,404 and 8,382,667, both issued in the name of the present applicant and both entitled, "Detecting, Quantifying, and/or Classifying Seizures Using Multimodal Data," as well as in co-pending U.S. patent application Ser. No. 13/288,886, filed Nov. 3, 2011, each hereby incorporated by reference in its entirety herein. Seizure detection based on the patient's heart rate (as sensed by implanted or external electrodes), movement (as sensed by, e.g., a triaxial accelerometer), responsiveness, breathing, blood oxygen saturation, skin resistivity/conductivity, temperature, brain activity, and a number of other body data streams are provided in the foregoing patents and co-pending applications.

In one embodiment, the present disclosure provides a method for treating a patient with epilepsy in which a body data stream is analyzed using a seizure detection algorithm to determine whether or not the patient has had an epileptic seizure. As used herein, the term "has had an epileptic seizure" includes instances in which a seizure onset has been detected, as well as instances in which the seizure onset has been detected and the seizure is still ongoing (i.e., the seizure has not ended). If the analysis results in a determination that the patient has not had an epileptic seizure, a signal generator may apply a first electrical signal to a main trunk of a vagus nerve of the patient. If the analysis results in a determination that the patient has had an epileptic seizure, the signal generator may apply a second electrical signal to a cardiac branch of a vagus nerve of the patient. In some embodiments, the application of the first electrical signal to the main trunk is terminated, and only the second electrical signal to the cardiac branch is provided once a seizure is detected.

In alternative embodiments, both the first and second electrical signals may be applied to the main trunk and cardiac branch, respectively, of the vagus nerve in response to a determination that the patient has had a seizure (i.e., the first electrical signal continues to be applied to the main trunk of the vagus nerve and the second signal is initiated). Where both the first and second electrical signals are provided, the two signals may be provided sequentially, or in alternating fashion to the main trunk and the cardiac branch. In one embodiment, the first signal may be provided to the main trunk by using one of the upper main trunk electrode 125-1 or the lower main trunk electrode 125-3 as the cathode and the cardiac branch electrode 125-2 as the anode, or by using both of the upper main trunk electrode and the lower main trunk electrode as the cathode and the anode. The second signal may be provided (e.g., by rapidly changing the polarity of the electrodes) by using the cardiac branch electrode 125-2 as the cathode and a main trunk electrode 125-1 or 125-3 as the anode.

In still other embodiments, the second electrical signal is applied to the cardiac branch of the vagus nerve only if the analysis results in a determination that the patient is having and/or has had an epileptic event that is accompanied by an increase in heart rate, and the second electrical signal is used to lower the heart rate back towards a rate that existed prior to the seizure onset. Without being bound by theory, the present inventors believe that slowing the heart rate at the onset of seizures—particularly where the seizure is accompanied by an increase in heart rate—may improve the ability of VNS therapy to provide cardio-protective benefits.

Prior patents describing vagus nerve stimulation as a medical therapy have cautioned that undesired slowing of the heart rate may occur, and have proposed various methods of avoiding such a slowing of the heart rate. In U.S. Pat. No. 6,341,236, it is suggested to sense heart rate during delivery of VNS and if a slowing of the heart rate is detected, either suspending delivery of the VNS signal or pacing the heart using a pacemaker. The present application discloses a VNS system that detects epileptic seizures, particularly epileptic seizures accompanied by an increase in heart rate, and intentionally applies an electrical signal to slow the heart rate in response to such a detection. In another aspect, the present application discloses VNS systems that provide a first electrical signal to modulate only the brain during periods in which no seizure has been detected, and either 1) a second electrical signal to modulate only the heart (to slow its rate) or 2) both a first electrical signal to the brain and a second electrical signal to the heart, in response to a detection of the onset of an epileptic seizure. These electrical signals may be delivered simultaneously, sequentially (e.g., delivery of stimulation to the brain precedes delivery of stimulation to the heart or vice versa), or delivery of the first and second signals may be interspersed or interleaved.

The first electrode may be used as a cathode to provide an afferent first electrical signal to modulate the brain of the patient via main trunk electrode 125-1. Electrode 125-1 may generate both afferent and efferent action potentials in vagus nerve 127. One or more of electrodes 125-2 and 125-3 are used as anodes to complete the circuit. Where this is the case, some of the action potentials may be blocked at the anode(s), with the result that the first electrical signal may predominantly modulate the brain by afferent actions traveling toward the brain, but may also modulate one or more other organs by efferent action potentials traveling toward the heart and/or lower organs, to the extent that the efferent action potentials are not blocked by the anode(s).

The second electrode may be used as a cathode to provide an efferent second electrical signal to slow the heart rate of the patient via cardiac branch electrode 125-2. Either first electrode 125-1 or a third electrode 125-3 (or can 121) may be used as an anode to complete the circuit. In one embodiment, the first electrical signal may be applied to the upper (127-1) or lower (127-3) main trunk of the vagus nerve in an open-loop manner according to programmed parameters including an off-time and an on-time. The on-time and off-time together establish the duty cycle determining the fraction of time that the signal generator applies the first electrical. In one embodiment, the off-time may range from 7 seconds to several hours or even longer, and the on-time may range from 5 seconds to 300 seconds. It should be noted that the duty cycle does not indicate when current is flowing through the circuit, which is determined from the on-time together with the pulse frequency (usually 10-200, Hz, and more commonly 20-30 Hz) and pulse width (typically 0.1-0.5 milliseconds). The first electrical signal may also be defined by a current magnitude (e.g., 0.25-3.5 milliamps), and possibly other parameters (e.g., pulse width, and whether or not a current ramp-up and/or ramp-down is provided, a frequency, and a pulse width.

In one embodiment, a seizure detection may result in both applying the first electrical signal to provide stimulation to the brain in close proximity to a seizure detection (which may interrupt or terminate the seizure), as well as application of the second electrical signal which may slow the heart, thus exerting a cardio-protective effect. In a particular embodiment, the second electrical signal is applied only in response to a seizure detection that is characterized by (or accompanied or associated with) an increase in heart rate, and is not applied in response to seizure detections that are not characterized by an increase in heart rate. In this manner, the second electrical signal may help interrupt the seizure by restoring the heart to a pre-seizure baseline heart rate when the patient experiences ictal tachycardia (elevated heart rate during the seizure), while leaving the heart rate unchanged if the seizure has no significant effect on heart rate.

In still further embodiments, additional logical conditions may be established to control when the second electrical signal is applied to lower the patient's heart rate following a seizure detection. In one embodiment, the second electrical signal is applied only if the magnitude of the ictal tachycardia rises above a defined level. In one embodiment, the second electrical signal is applied to the cardiac branch only if the heart rate increases by a threshold amount above the pre-ictal baseline heart rate (e.g., more than 20 beats per minute above the baseline rate). In another embodiment, the second electrical signal is applied to the cardiac branch only if the heart rate exceeds an absolute heart rate threshold (e.g., 100 beats per minute, 120 beats per minute, or other programmable threshold). In a further embodiment, a duration constraint may be added to one or both of the heart rate increase or absolute heart rate thresholds, such as a requirement that the heart rate exceed the baseline rate by 20 beats per minute for more than 10 seconds, or exceed 110 beats per minute for more than 10 seconds, before the second electrical signal is applied to the cardiac branch in response to a seizure detection.

In another embodiment, the heart rate sensor continues to monitor the patient's heart rate during and/or after application of the second electrical signal, and the second electrical signal is interrupted or terminated if the patient's heart rate is reduced below a low heart rate threshold, which may be the baseline heart rate that the patient experienced prior to the seizure, or a rate lower or higher than the baseline pre-ictal heart rate. The low rate threshold may provide a measure of safety to avoid undesired events such as bradycardia and/or syncope.

In yet another embodiment, heart rate sensor 130 may continue to monitor heart rate and/or kinetic sensor 140 may continue to monitor body movement in response to applying the second electrical signal, and the second electrical signal may be modified (e.g., by changing one or more parameters such as pulse frequency, or by interrupting and re-initiating the application of the second electrical signal to the cardiac branch of the vagus nerve) to control the heart rate below an upper heart rate threshold and/or body movement exceeds one or more movement thresholds. For example, the frequency or duration of the second electrical signal applied to the cardiac branch of the vagus nerve may be continuously modified based the instantaneous heart rate as monitored during the course of a seizure to control what would otherwise be an episode of ictal tachycardia below an upper heart rate threshold. In one exemplary embodiment, the second electrical signal may be programmed to provide a 30-second pulse burst at 30 Hz, with the pulses having a pulse width of 0.25 milliseconds and a current of 1.5 milliamps. If, at the end of the 30 second burst, the heart rate remains above 120 beats per minute, and is continuing to rise, the burst may be extended to 1 minute instead of 30 seconds, the frequency may be increased to 50 Hz, the pulse width may be increased to 350 milliseconds, or combinations of the foregoing. In still further embodiments, additional therapies (e.g., oxygen delivery, drug delivery, cooling therapies, etc.) may be provided to the patient if the body data (heart rate, kinetic activity, etc.) indicates that the patient's seizure is not under control or terminated.

Abnormalities or changes in EKG morphology or rhythm relative to an interictal morphology or rhythm may also trigger delivery of current to the heart via the trunks of vagi or its cardiac rami. In other embodiments, pharmacological agents such as beta-blockers may be automatically released into a patient's blood stream in response to the detection of abnormal heart activity during or between seizures.

In one embodiment, the first electrical signal and the second electrical signal are substantially identical. In another embodiment, the first electrical signal may vary from the second electrical signal in terms of one or more of pulse width, number of pulses, amplitude, frequency, interpulse-interval, stimulation on-time, and stimulation off-time, among other parameters and degree, rate or type of charge balancing.

The number of pulses applied to the main trunk or cardiac branch, respectively, before changing the polarity of the first and second electrodes need not be one. Thus, two or more pulses may be applied to the main trunk before applying pulses to the cardiac branch of the vagus nerve. More generally, the first and second signals can be independent of one another and applied according to timing and programming parameters controlled by the controller 210 and stimulation unit 220.

In one embodiment, one or more pulse bursts of the first electrical signal are applied to the main trunk of the vagus nerve in response to a detected seizure before applying one or more bursts of the second electrical signal to the cardiac branch. In another embodiment, the first and second signals are interleaved on a pulse-by-pulse basis under the control of the controller 210 and stimulation unit 220.

Typically, VNS can be performed with pulse frequency of 20-30 Hz (resulting in a number of pulses per burst of 140-1800, at a burst duration from 7-60 sec). In one embodiment, at least one of the first electrical signal and the second electrical signal comprises a microburst signal. Microburst neurostimulation is discussed by U.S. Ser. No. 11/693,451, filed Mar. 2, 2007 and published as United States patent Publication No. 20070233193, and incorporated herein by reference in its entirety. In one embodiment, at least one of the first electrical signal, the second electrical signal, and the third electrical signal is characterized by having a number of pulses per microburst from 2 pulses to about 25 pulses, an interpulse interval of about 2 msec to about 50 msec, an interburst period of at least 100 msec, and a microburst duration of less than about 1 sec.

Cranial nerves such as the vagus nerve include different types of nerve fibers, such as A-fibers, B-fibers and C-fibers. The different fiber types propagate action potentials at different velocities. Each nerve fiber is directional—that is, endogenous or natural action potentials can generally propagate action potentials in only one direction(e.g., afferently to the brain or efferently to the heart and/or viscera). That direction is referred to as the orthodromic direction. Exogenous stimulation (e.g., by electrical pulses) may induce action potentials in both the orthodromic direction as well as the antidromic direction. Depending upon the desired effects of stimulation (e.g., afferent modulation of the brain, efferent modulation of the heart, etc.) certain measures (e.g., cooling, pressure, etc.) may be taken to block propagation in either the efferent or the afferent direction. It is believed that the anode may block at least some action potentials traveling to it from the cathode. For example, referring to FIG. 1, both afferent and efferent action potentials may be generated in an upper main trunk of vagus nerve 127-1 by applying a pulse to the nerve using upper main trunk electrode 125-1 as a cathode. Action potentials generated at upper main trunk electrode 125-1 and traveling toward the heart on cardiac branch 127-2 may be blocked by cardiac branch anode 125-2. Action potentials traveling from the upper main trunk 127-1 to the lower organs in lower main trunk 127-3 may be either blocked (by using lower main trunk electrode 125-3 as an anode either with or instead of cardiac branch electrode 125-2) or allowed to travel to the lower organs (by not using electrode structure 125-3 as an electrode).

Action potentials may be generated and allowed to travel to the heart by making the electrode 125-2 the cathode. If cardiac branch electrode 125-2 is used as a cathode, action potentials will reach the heart in large numbers, while action potentials traveling afferently toward the brain may be blocked in the upper trunk if upper electrode 125-1 is made the anode.

In a further embodiment of the disclosure, rapid changes in electrode polarity may be used to generate action potentials to collision block action potentials propagating in the opposite direction. To generalize, in some embodiments, the vagus nerve can be selectively stimulated to propagate action potentials either afferently (i.e., to the brain) or efferently (i.e., to the heart and/or lower organs/viscerae).

Figure 2:
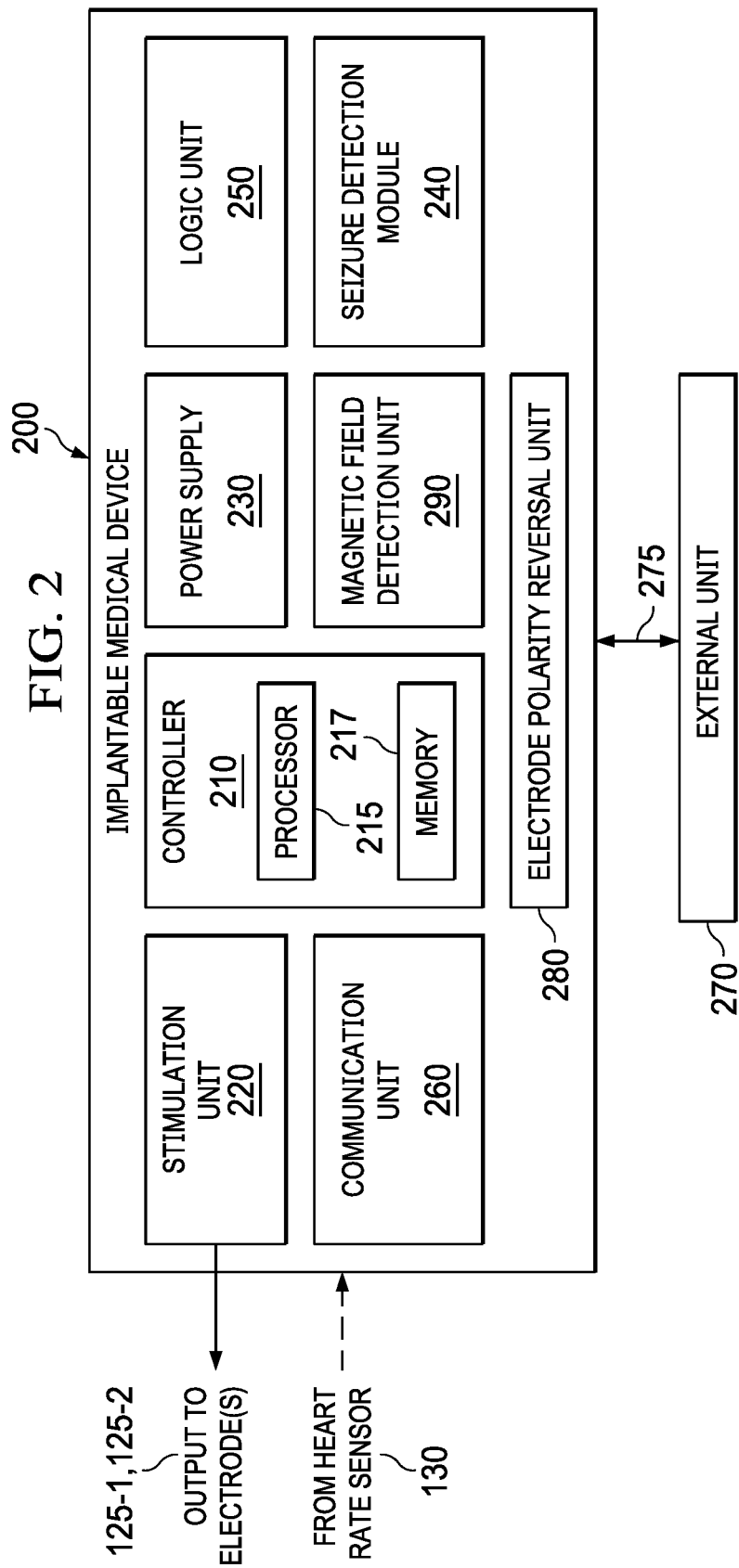
FIG. 2 illustrates a block diagram depiction of an implantable medical device of FIG. 1, in accordance with one illustrative embodiment of the present disclosure.

Turning now to FIG. 2, a block diagram depiction of an implantable medical device, in accordance with one illustrative embodiment of the present disclosure is illustrated. The IMD 200 may be coupled to various electrodes 125 and/or 127 via lead(s) 122 (FIGS. 1A, 1C). First and second electrical signals used for therapy may be transmitted from the IMD 200 to target areas of the patient's body, specifically to various electrodes associated with the leads 122. Stimulation signals from the IMD 200 may be transmitted via the leads 122 to stimulation electrodes (electrodes that apply the therapeutic electrical signal to the target tissue) associated with the electrode assembly 125, e.g., 125-1, 125-2, 125-3 (FIG. 1A).

The IMD 200 may comprise a controller 210 capable of controlling various aspects of the operation of the IMD 200. The controller 210 is capable of receiving internal data and/or external data and controlling the generation and delivery of a stimulation signal to target tissues of the patient's body. For example, the controller 210 may receive manual instructions from an operator externally, may perform stimulation based on internal calculations and programming, and may receive and/or process sensor data received from one or more body data sensors such as electrodes 125-1, 125-2, 125-3, or heart rate sensor 130. The controller 210 is capable of affecting substantially all functions of the IMD 200.

The controller 210 may comprise various components, such as a processor 215, a memory 217, etc. The processor 215 may comprise one or more micro controllers, microprocessors, etc., that are capable of executing a variety of software components. The processor may receive, pre-condition and/or condition sensor signals, and may control operations of other components of the IMD 200, such as stimulation unit 220, seizure detection module 240, logic unit 250, communication unit 260, and electrode polarity reversal unit 280. The memory 217 may comprise various memory portions, where a number of types of data (e.g., internal data, external data instructions, software codes, status data, diagnostic data, etc.) may be stored. The memory 217 may store various tables or other database content that could be used by the IMD 200 to implement the override of normal operations. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering a variety of electrical signal therapy signals to one or more electrodes via leads. The stimulation unit 220 is capable of delivering a programmed, first electrical signal to the leads 122 coupled to the IMD 200. The electrical signal may be delivered to the leads 122 by the stimulation unit 220 based upon instructions from the controller 210. The stimulation unit 220 may comprise various types of circuitry, such as stimulation signal generators, impedance control circuitry to control the impedance "seen" by the leads, and other circuitry that receives instructions relating to the type of stimulation to be performed.

Signals from sensors (electrodes that are used to sense one or more body parameters such as temperature, heart rate, brain activity, etc.) may be provided to the IMD 200. The body signal data from the sensors may be used by a seizure detection algorithm embedded or processed in seizure detection module 240 to determine whether or not the patient is having and/or has had an epileptic seizure. The seizure detection algorithm may comprise hardware, software, firmware or combinations thereof, and may operate under the control of the controller 210. Although not shown, additional signal conditioning and filter elements (e.g., amplifiers, D/A converters, etc., may be used to appropriately condition the signal for use by the seizure detection module 240. Sensors such as heart sensor 130 and kinetic sensor 140 may be used to detect seizures, along with other autonomic, neurologic, or other body data.

The IMD 200 may also comprise an electrode polarity reversal unit 280. The electrode polarity reversal unit 280 is capable of reversing the polarity of electrodes (125-1, 125-2, 125-3) associated with the electrode assembly 125. The electrode polarity reversal unit 280 is shown in more detail in FIG. 3. In preferred embodiments, the electrode polarity reversal unit is capable of reversing electrode polarity rapidly, i.e., in about 10 microseconds or less, and in any event at a sufficiently rapid rate to permit electrode polarities to be changed between adjacent pulses in a pulsed electrical signal.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230 may comprise a lithium/thionyl chloride cell or a lithium/carbon monofluoride (LiCFx) cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 comprises a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming. The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

In one embodiment, the communication unit 260 can transmit a log of stimulation data and/or seizure detection data to the patient, a physician, or another party.

Figure 1D:
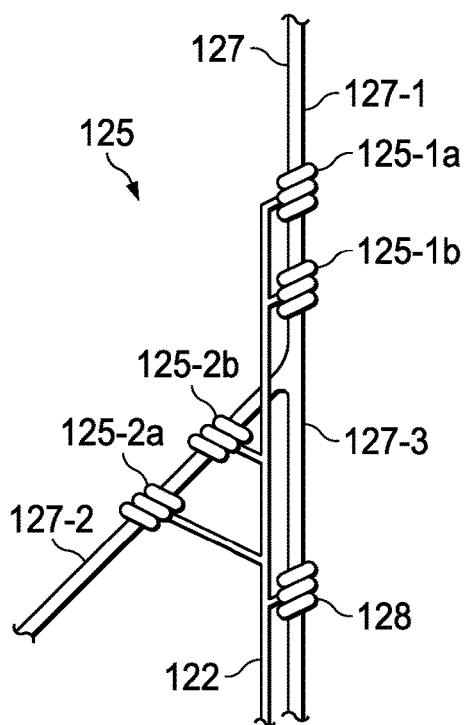
Figure 1E:
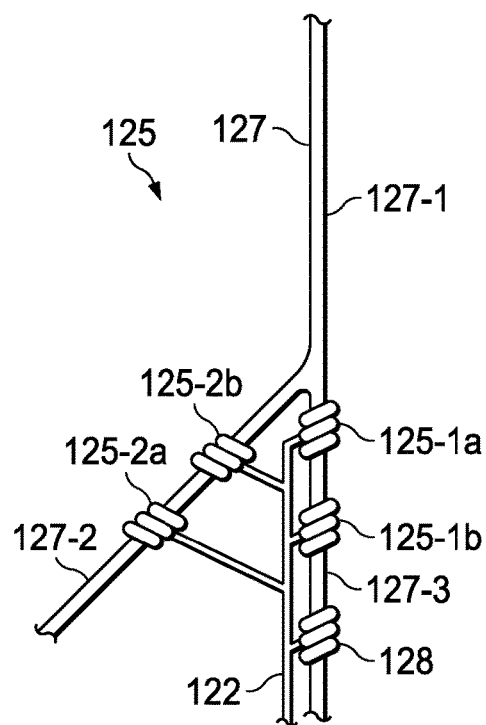

In one embodiment, a method of treating an epileptic seizure is provided that involves providing simultaneously both a first electrical signal to a main trunk of a vagus nerve and a second electrical signal to a cardiac branch of the vagus nerve. As used herein "simultaneously" refers to the on-time of the first and second signals, and does not require that individual pulses of the first signal and the second signal be simultaneously applied to target tissue. The timing of pulses for the first electrical signal and the second electrical signal may be determined by controller 210 in conjunction with stimulation unit 220. Where active charge-balancing is used, it may be possible to use the active charge-balancing phase of pulses of the first electrical signal as the stimulation phase of the second electrical signal by selecting a current magnitude of the cathode in the charge-balancing phase (typically a second electrode, which may be the anode of the initial stimulation phase) that is sufficient to generate action potentials in nerve fibers of the target tissue. Controller 210 may in some embodiments provide simultaneous delivery of first and second electrical signals by interleaving pulses for each of the first and second electrical signals based upon the programmed timing of pulses for each signal and the appropriate polarity of each of first and second electrodes 125-1 and 125-2. In some embodiments, additional electrodes may be used to minimize the induction of action potentials to the heart or the brain provided by the first electrical signal or the second electrical signal. This may be accomplished, in one embodiment, by using an anode located on either the upper main trunk or the cardiac branch to block impulse conduction to the heart or brain from the cathode, or by providing dedicated electrode pairs on both the main trunk and cardiac branches (FIGS. 1D, 1E). When beneficial, steps to avoid collisions of actions potentials travelling in opposite directions may be implemented, while steps to promote collisions may be taken when clinically indicated. In some embodiments, the method further includes sensing a cardiac signal and a kinetic signal of the patient, and detecting a seizure event with a seizure detection algorithm.

In one embodiment, a first electrical signal is applied to a main trunk of a vagus nerve and a second electrical signal is simultaneously applied to a cardiac branch of a vagus nerve. A pulse of the first electrical signal is generated with the electrical signal generator 110 and applied to the main trunk of the vagus nerve using a first electrode (e.g., 125-1, 125-1a) as a cathode and a second electrode (e.g., 125-1b, 125-3, or 125-2) as an anode. The method includes sensing a cardiac signal and a kinetic signal of the patient, and detecting a seizure event with a seizure detection algorithm. A pulse of the second electrical signal (having the appropriate pulse width and current) is generated and applied (under appropriate timing control by controller 110 and stimulation unit 220) to the cardiac branch of the vagus nerve using a second electrode (e.g., 125-2, 125-2a) as a cathode and another electrode (e.g., 125-3, 125-1, 125-2b) as an anode. Another pulse of the first electrical signal may thereafter be generated and applied to the main trunk under timing and parameter control of controller 210 and stimulation unit 220. By appropriate selection of cathodes and anodes, the first and second electrical signals may be interleaved and provided simultaneously to the main trunk and cardiac branches of the vagus nerve. In some embodiments, the number of electrodes may be minimized by provided a polarity reversal unit that may rapidly change the polarity of particular electrodes to allow their use in delivering both the first and second signals.

The IMD 200 is capable of delivering stimulation that can be contingent, periodic, random, coded, and/or patterned. The stimulation signals may comprise an electrical stimulation frequency of approximately 0.1 to 10,000 Hz. The stimulation signals may comprise a pulse width in the range of approximately 1-2000 micro-seconds. The stimulation signals may comprise current amplitude in the range of approximately 0.1 mA to 10 mA. Appropriate precautions may be taken to avoid delivering injurious current densities to target neural tissues, e.g., by selecting current, voltage, frequency, pulse width, on-time and off-time parameters to maintain current density below thresholds for damaging tissues.

The IMD 200 may also comprise a magnetic field detection unit 290. The magnetic field detection unit 290 is capable of detecting magnetic and/or electromagnetic fields of a predetermined magnitude. Whether the magnetic field results from a magnet placed proximate to the IMD 200, or whether it results from a substantial magnetic field encompassing an area, the magnetic field detection unit 290 is capable of informing the IMD of the existence of a magnetic field. The changeable electrode polarity stimulation described herein may be activated, deactivated, or alternatively activated or deactivated using a magnetic input.

The magnetic field detection unit 290 may comprise various sensors, such as a Reed Switch circuitry, a Hall Effect sensor circuitry, and/or the like. The magnetic field detection unit 290 may also comprise various registers and/or data transceiver circuits that are capable of sending signals that are indicative of various magnetic fields, the time period of such fields, etc. In this manner, the magnetic field detection unit 290 is capable of detecting whether the detected magnetic field relates to an input to implement a particular first or second electrical signal (or both) for application to the main trunk of cardiac branches, respectively, of the vagus nerve.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, one or more of the circuitry and/or software units associated with the various blocks illustrated in FIG. 2 may be combined into a programmable device, such as a field programmable gate array, an ASIC device, etc.

Figure 3:
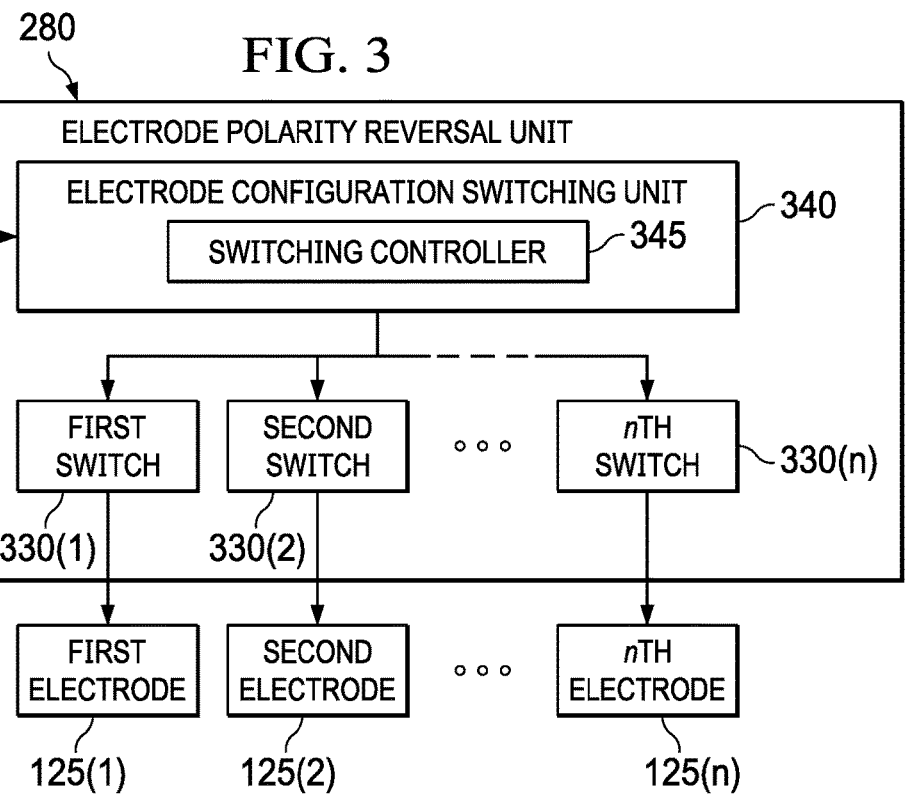
FIG. 3 illustrates a block diagram depiction of an electrode polarity reversal unit shown in FIG. 2, in accordance with one illustrative embodiment of the present disclosure.

FIG. 3 shows in greater detail an electrode polarity reversal unit 280 (FIG. 2) in one embodiment. The electrode polarity reversal unit 280 comprises an electrode configuration switching unit 340, which includes a switching controller 345. The switching controller 345 transmits signals to one or more switches, generically, n switches 330(1), 330(2), . . . 330(n) which effect the switching of the configuration of two or more electrodes, generically, n electrodes 125(1), 125(2), . . . 125(n). Although FIG. 3 shows equal numbers of switches 330 and electrodes 125, persons of skill in the art having the benefit of the present disclosure will understand that the number of switches 330 and their connections with the various electrodes 125 can be varied as a matter of routine optimization. A switching timing unit 333 can signal to the electrode configuration switching unit 340 that a desired time for switching the electrode configuration has been reached.

Instructions for implementing two or more stimulation regimens, which may include at least one open-loop electrical signal and at least one closed-loop electrical signal, may be stored in the IMD 200. These stimulation signals may include data relating to the type of stimulation signal to be implemented. In one embodiment, an open-loop signal may be applied to generate action potentials for modulating the brain of the patient, and a closed-loop signal may be applied to generate either action potentials for slowing the heart rate of the patient, or both action potentials to modulate the brain of the patient as well as action potentials for slowing the heart rate of the patient. In some embodiments, the open-loop and closed-loop signals may be provided to different target portions of a vagus nerve of the patient by switching the polarity of two or more electrodes using an electrode polarity reversal unit as described in FIG. 3 above. In alternative embodiments, additional electrodes may be provided to generate each of the open-loop and closed-loop signals without electrode switching.

In one embodiment, a first open-loop mode of stimulation may be used to provide an electrical signal to a vagus nerve using a first electrode as a cathode on a main trunk (e.g., 127-1 or 127-3 using electrodes 125-1 or 125-3, respectively) of a vagus nerve, and a second electrode as an anode on either a main trunk (e.g., electrode 125-3, when electrode 125-1 is used as a cathode) or cardiac branch (e.g., electrode 125-2) of a vagus nerve. The first open-loop signal may include a programmed on-time and off-time during which electrical pulses are applied (the on-time) and not-applied (the off-time) in a repeating sequence to the vagus nerve.

A second, closed-loop signal may be provided in response to a detected event (such as an epileptic seizure, particularly when accompanied by an increase in the patient's heart rate) using a different electrode configuration than the first, open-loop signal. In one embodiment, the second, closed-loop signal is applied to a cardiac branch using the second electrode 125-2 as a cathode and the first electrode on the main trunk (e.g., 125-1 or 125-3) as an anode. The second, closed-loop signal may involve generating efferent action potentials on the cardiac branch of the vagus nerve to slow the heart rate. In some embodiments, the first, open-loop signal may be interrupted/suspended in response to the detected event, and only the second, closed-loop signal is applied to the nerve. In other embodiments, the first, open loop signal may not be interrupted when the event is detected, and both the first, open-loop signal and the second, closed-loop signal are applied to the vagus nerve. In another embodiment, a third, closed-loop signal may also be provided in response to the detected event. The third, closed-loop signal may involve an electrical signal using the same electrode configuration as the first, open-loop electrical signal, but may provide a different electrical signal to the main trunk of the vagus nerve than either the first, open-loop signal or the second, closed-loop signal. The first, open-loop signal may be interrupted, terminated or suspended in response to the detected event, and the third, closed-loop signal may be applied to the nerve either alone or with the second, closed-loop signal. In some embodiments, both the second and third closed-loop signals may be provided in response to a detected epileptic seizure by rapidly changing the polarity of the first (125-1) and second (125-2) electrodes from cathode to anode and back, as pulses are provided as part of the second and third electrical signals, respectively. In one embodiment, the third electrical signal may involve modulating the brain by using a main trunk electrode (e.g., upper main trunk electrode 125-1) as a cathode and another electrode (e.g., cardiac branch electrode 125-2 or lower main trunk electrode 125-3) as an anode. The third electrical signal may comprise, for example, a signal that is similar to the first electrical signal but which provides a higher electrical current than the first electrical signal, and for a longer duration than the first signal or for a duration that is adaptively determined based upon a sensed body signal (in contrast, for example, to a fixed duration of the first electrical signal determined by a programmed on-time). By rapidly changing polarity of the electrodes, pulses for each of the second and third electrical signals may be provided such that the second and third signals are provided simultaneously to the cardiac branch and main trunk of the vagus nerve. In other embodiments, the first, second and third electrical signals may be provided sequentially rather than simultaneously.

In some embodiments, one or more of the first, second and third electrical signals may comprise a microburst signal, as described more fully in U.S. patent application Ser. Nos. 11/693,421, 11/693,451, and 11/693,499, each filed Mar. 29, 2007 and each hereby incorporated by reference herein in their entirety.

In one embodiment, each of a plurality of stimulation regimens may respectively relate to a particular disorder, or to particular events characterizing the disorder. For example, different electrical signals may be provided to one or both of the main trunk and cardiac branches of the vagus nerve depending upon what effects accompany the seizure. In a particular embodiment, a first open-loop signal may be provided to the patient in the absence of a seizure detection, while a second, closed-loop signal may be provided when a seizure is detected based on a first type of body movement of the patient as detected by, e.g., an accelerometer, a third, closed-loop signal may be provided when the seizure is characterized by a second type of body movement, a fourth, closed-loop signal may be provided when the seizure is characterized by an increase in heart rate, a fifth, closed-loop signal may be provided when the seizure is characterized by a decrease in heart rate, and so on. More generally, stimulation of particular branches or main trunk targets of a vagus nerve may be provided based upon different body signals of the patient. In some embodiments, additional therapies may be provided based on different events that accompany the seizure, e.g., stimulation of a trigeminal nerve or providing a drug therapy to the patient through a drug pump. In one embodiment, different regimens relating to the same disorder may be implemented to accommodate improvements or regressions in the patient's present condition relative to his or her condition at previous times. By providing flexibility in electrode configurations nearly instantaneously, the present disclosure greatly expands the range of adjustments that may be made to respond to changes in the patient's underlying medical condition.

The switching controller 345 may be a processor that is capable of receiving data relating to the stimulation regimens. In an alternative embodiment, the switching controller may be a software or a firmware module. Based upon the particulars of the stimulation regimens, the switching timing unit 333 may provide timing data to the switching controller 345. The first through nth switches 330(1-*n*) may be electrical devices, electro-mechanical devices, and/or solid state devices (e.g., transistors).

Figure 4:
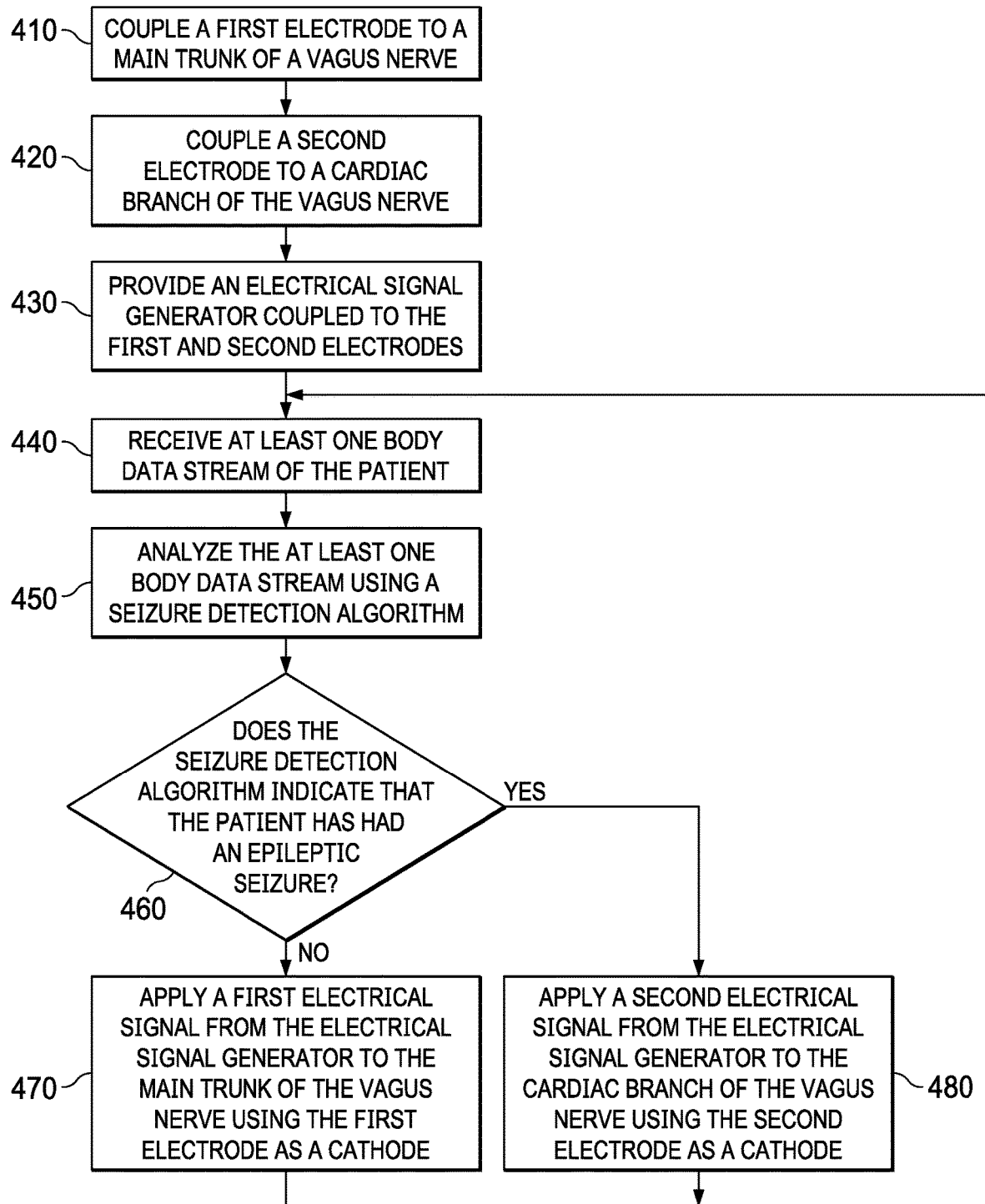
FIG. 4 illustrates a flowchart depiction of a method for providing first and second electrical signals to a main trunk and a cardiac branch of a vagus nerve, respectively, based upon whether or not the patient is having and/or has had an epileptic seizure, in accordance with an illustrative embodiment of the present disclosure.

FIG. 4 shows one embodiment of a method of treating a patient having epilepsy according to the present disclosure. In this embodiment, a first electrode is coupled to a main trunk of a vagus nerve of the patient (410) and a second electrode is coupled to a cardiac branch of the vagus nerve (420). An electrical signal generator is coupled to the first and second electrodes (430).

The method further involves receiving at least one body data stream of the patient (440). The data may be sensed by a sensor such as heart rate sensor 130 (FIG. 1A) or a sensor that is an integral part of, or coupled to, an IMD 200 (FIG. 2) such as electrical pulse generator 110 (FIG. 1A), and the IMD may also receive the data from the sensor. The at least one body data stream is then analyzed using a seizure detection algorithm (450), and the seizure detection algorithm determines whether or not the patient is having and/or has had an epileptic seizure (460).

If the algorithm indicates that the patient is not having and/or has not had an epileptic seizure, the method comprises applying a first electrical signal from the electrical signal generator to the main trunk of a vagus nerve using the first electrode as a cathode (470). In one embodiment, applying the first electrical signal comprises continuing to apply a programmed, open-loop electrical signal periodically to the main trunk of the vagus nerve according a programmed on-time and off-time.

If the algorithm indicates that the patient is having and/or has had an epileptic seizure, the method comprises applying a second electrical signal from the electrical signal generator to the cardiac branch of the vagus nerve using the second electrode as a cathode (480). Depending upon which electrical signal (first or second) is applied, the method may involve changing the polarity of one or both of the first electrode and the second electrode. In one embodiment, the method may comprise suspending the first electrical and applying the second electrical signal. In one embodiment, the method comprises continuing to receive at least one body data stream of the patient at 440 after determining whether or not the patient is having and/or has had an epileptic seizure.

In an alternative embodiment, if the seizure detection algorithm indicates that the patient is having and/or has had an epileptic seizure, both the first electrical signal and the second electrical signal are applied to the main trunk and cardiac branches of a vagus nerve of the patient, respectively, at step 480. In a specific implementation of the alternative embodiment, pulses of the first and second electrical signal are applied to the main trunk and cardiac branch of the vagus nerve under the control of controller 210 by rapidly changing the polarity of the first and second electrodes using the electrode polarity reversal unit 280 to apply the first electrical signal to the main trunk using the first electrode as a cathode and the second electrode as an anode, changing the polarity of the first and second electrodes, and applying the second electrical signal to the cardiac branch using the second electrode as a cathode and the first electrode as an anode. Additional pulses for each signal may be similarly applied by rapidly changing the polarity of the electrodes.

In some embodiments, the first electrical signal and the second electrical signal are applied unilaterally, i.e., to a vagal main trunk and a cardiac branch on the same side of the body. In other embodiments, the first and second electrical signals are applied bilaterally, i.e., the second electrical signal is applied to a cardiac branch on the opposite side of the body from the main vagal trunk to which the first electrical signal is applied. In one embodiment, the first electrical signal is applied to a left main trunk to minimize cardiac effects of the first electrical signal, and the second electrical signal is applied to a right cardiac branch, which modulates the sinoatrial node of the heart to maximize cardiac effects of the second electrical signal.

In alternative embodiments, both the first electrode and the second electrode may be coupled to a cardiac branch of a vagus nerve, with the first electrode (e.g., anode) being proximal to the brain relative to the second electrode, and the second electrode (e.g., cathode) being proximal to the heart relative to the first electrode.

Figure 5:
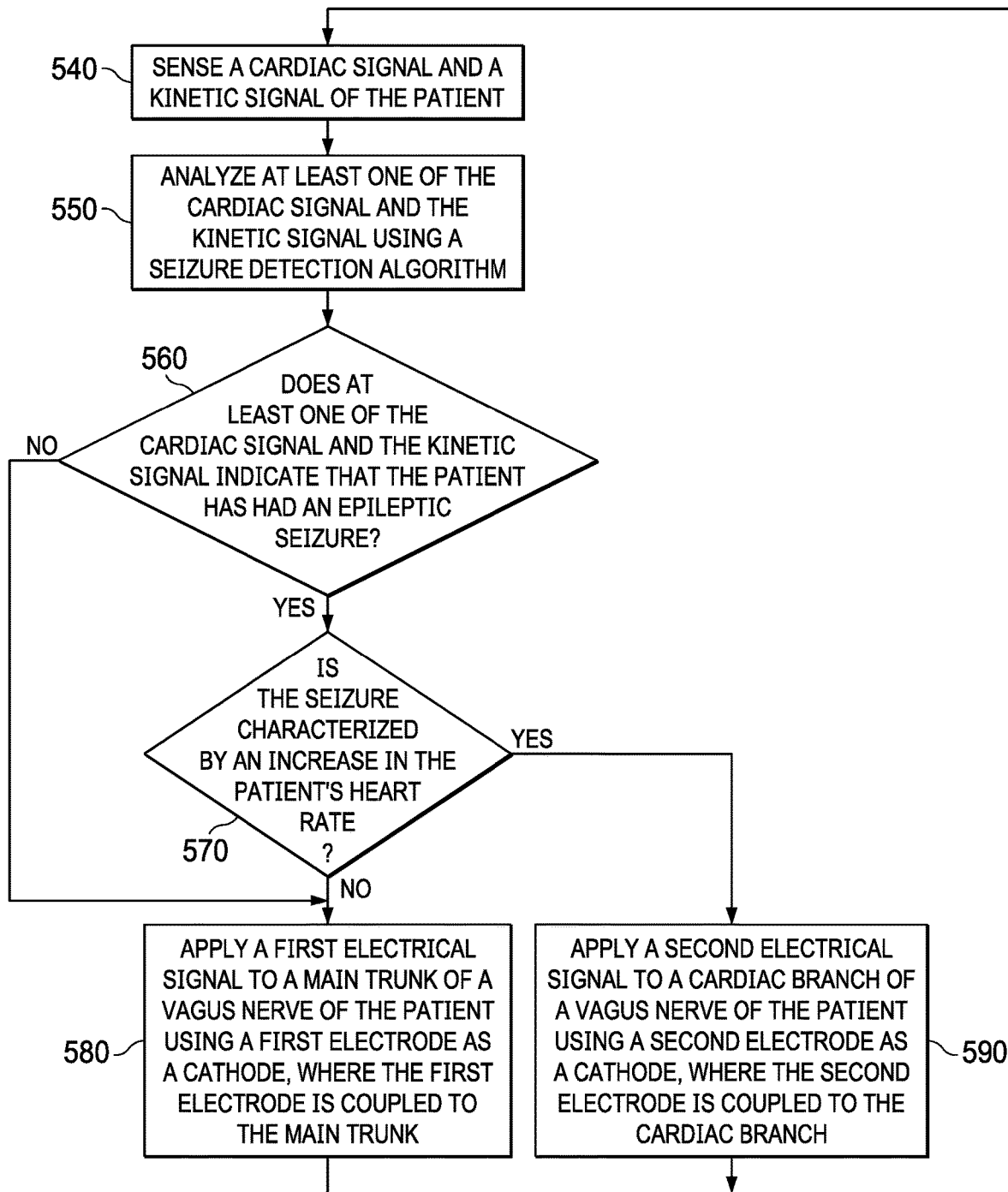
FIG. 5 illustrates a flowchart depiction of a method for providing first and second electrical signals to a main trunk and a cardiac branch of a vagus nerve, respectively, based upon whether or not at least one of a cardiac signal and a kinetic signal indicates that the patient is having and/or has had an epileptic seizure, and whether the seizure is characterized by an increase in heart rate, in accordance with an illustrative embodiment of the present disclosure.

FIG. 5 is a flow diagram of another method of treating a patient having epilepsy according to the present disclosure. A sensor is used to sense a cardiac signal and a kinetic signal of the patient (540). In a particular embodiment, the cardiac sensor may comprise an electrode pair for sensing an ECG (electrocardiogram) or heart beat signal, and the kinetic signal may comprise a triaxial accelerometer to detect motion of at least a portion of the patient's body. The method further comprises analyzing at least one of the cardiac signal and the kinetic signal using seizure detection algorithm (550), and the output of the algorithm is used to determine whether at least one of the cardiac signal and the kinetic signal indicate that the patient is having and/or has had an epileptic seizure (560).

If the patient is not having and/or has not had an epileptic seizure, the method comprises applying a first electrical signal to a main trunk of a vagus nerve of the patient using a first electrode, coupled to the main trunk, as a cathode (580). In one embodiment, the first electrical signal is an open-loop electrical signal having an on-time and off-time.

If the patient is having and/or has had an epileptic seizure, a determination is made whether the seizure is characterized by an increase in the patient's heart rate (570). If the seizure is not characterized by an increase in the patient's heart rate, the method comprises applying the first electrical signal to the main trunk of a vagus nerve using the first electrode as a cathode (580). In one embodiment, the cathode comprises an upper main trunk electrode 125-1 and the anode is selected from a cardiac branch electrode 125-2 and a lower main trunk electrode 125-3. Conversely, if the seizure is characterized by an increase in the patient's heart rate, the method comprises applying a second electrical signal to a cardiac branch of a vagus nerve of the patient using a second electrode, coupled to the cardiac branch, as a cathode (590). The anode is an upper main trunk electrode 125-1 or a lower main trunk electrode 125-3. In one embodiment, the method may comprise suspending the first electrical and applying the second electrical signal.

The method then continues the sensing of the cardiac and kinetic signals of the patient (540) and resumes the method as outlined in FIG. 5.

Figure 6:
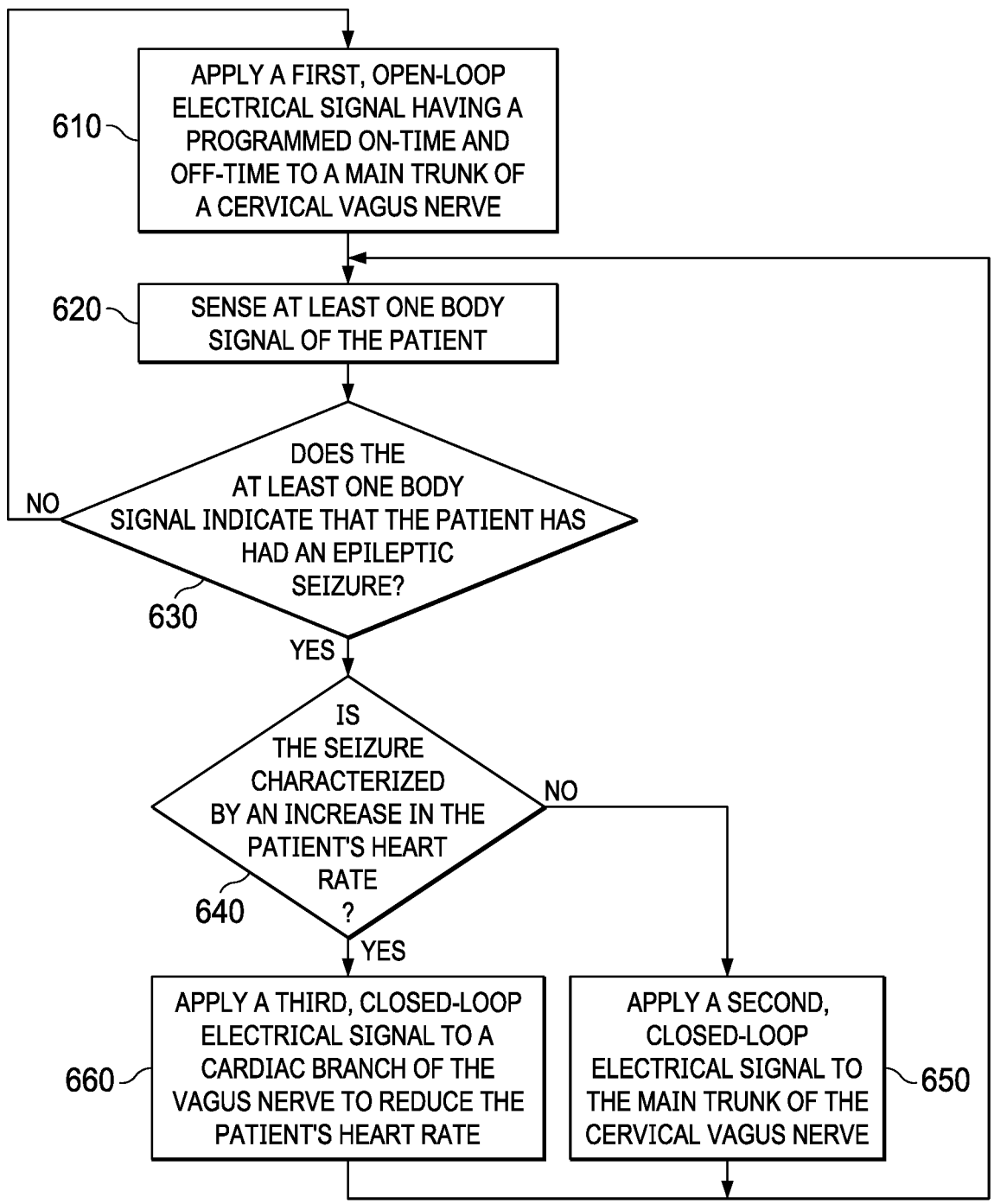
FIG. 6 illustrates a flowchart depiction of a method for providing a first, open-loop electrical signal to a main trunk of a vagus nerve, a second, closed-loop electrical signal to the main trunk of the vagus nerve based upon the patient having had an epileptic seizure not characterized by an increase in heart rate, and a third, closed-loop electrical signal to a cardiac branch of a vagus nerve based upon the patient having had an epileptic seizure characterized by an increase in heart rate, in accordance with an illustrative embodiment of the present disclosure.

FIG. 6 is a flow diagram of a further method of treating a patient having epilepsy according to the present disclosure. The method includes applying a first, open-loop electrical signal to a main trunk of a vagus nerve (610). The open-loop signal is characterized by an off-time in which electrical pulses are applied to the nerve, and an off-time in which electrical pulses are not applied to the nerve.

A sensor is used to sense at least one body signal of the patient (620), and a determination is made whether the at least one body signal indicates that the patient is having and/or has had an epileptic seizure (630). If the patient is not having and/or has not had a seizure, the method continues applying the first, open-loop electrical signal to a main trunk of a vagus nerve (610). If the patient is having and/or has had an epileptic seizure, a determination is made whether the seizure is characterized by an increase in the patient's heart rate (640). In one embodiment, the increase in heart rate is measured from a baseline heart rate existing prior to the seizure, e.g., a median heart rate for a prior period such as the 300 beats prior to the detection of the seizure event, or the 5 minutes prior to the detection of the seizure.

If the seizure is not characterized by an increase in the patient's heart rate, the method comprises applying a second, closed-loop electrical signal to the main trunk of the vagus nerve 650). In one embodiment, the second, closed-loop electrical signal is the same signal as the open-loop electrical signal, except that the second signal (as defined, e.g., by a current intensity, a pulse frequency, a pulse width and an on-time) is applied at a time different from the programmed timing of the first electrical signal. For example, if the first electrical signal comprises an on-time of 30 seconds and an off-time of 5 minutes, but a seizure is detected 1 minute after the end of a programmed on-time, the second electrical signal may comprise applying a 30 second pulse burst at the same current intensity, frequency, and pulse width as the first signal, but four minutes earlier than would have occurred absent the detected seizure. In another embodiment, the second, closed-loop electrical signal is a different signal than the first, open-loop electrical signal, and the method may also comprise suspending the first electrical before applying the second electrical signal. For example, the second, closed-loop electrical signal may comprise a higher current intensity, frequency, pulse width and/or on-time than the first, open-loop electrical signal, and may not comprise an off-time (e.g., the second electrical signal may be applied for a predetermined duration independent of the on-time of the first, open-loop electrical signal, such as a fixed duration of 1 minute, or may continue for as long as the body signal indicates the presence of the seizure event).

Returning to FIG. 6, if the seizure is characterized by an increase in the patient's heart rate, the method comprises applying a third, closed-loop electrical signal to a cardiac branch of a vagus nerve to reduce the patient's heart rate (660). The method may comprise suspending the first electrical as well as applying the third, closed-loop electrical signal. In one embodiment of the disclosure, each of the first, open-loop electrical signal, the second, closed-loop electrical signal, and the third, closed-loop electrical signal are applied unilaterally (i.e., to vagus nerve structures on the same side of the body) to the main trunk and cardiac branch of the vagus nerve. For example, the first, open-loop electrical signal and the second, closed-loop electrical signal may be applied to a left main trunk of the patient's cervical vagus nerve, and the third, closed-loop electrical signal may be applied to the left cardiac branch of the vagus nerve. Similarly, the first, second and third electrical signals may all be applied to the right vagus nerve of the patient. In alternative embodiments, one or more of the first, second and third electrical signals may be applied bilaterally, i.e., one of the first, second and third electrical signals is applied to a vagal structure on the opposite side of the body from the other two signals. For example, in a particular embodiment the first, open-loop signal and the second, closed-loop signal may be applied to a left main trunk of the patient's cervical vagus nerve, and the third, closed-loop electrical signal may be applied to a right cardiac branch of the patient's vagus nerve. Because the right cardiac branch modulates the sinoatrial node of the patient's heart, which is the heart's "natural pacemaker," the third electrical signal may have more pronounced effect in reducing the patient's heart rate if applied to the right cardiac branch.

After applying one of the second (650) and third (660) electrical signals to a vagus nerve of the patient, the method then continues sensing at least one body signal of the patient (620) and resumes the method as outlined in FIG. 6.

In the methods depicted in FIGS. 4-6, one or more of the parameters defining the first, second, and third electrical signals (e.g., number of pulses, pulse frequency, pulse width, On time, Off time, interpulse interval, number of pulses per burst, or interburst interval, among others) can be changed by a healthcare provided using a programmer 150.

Figure 7:
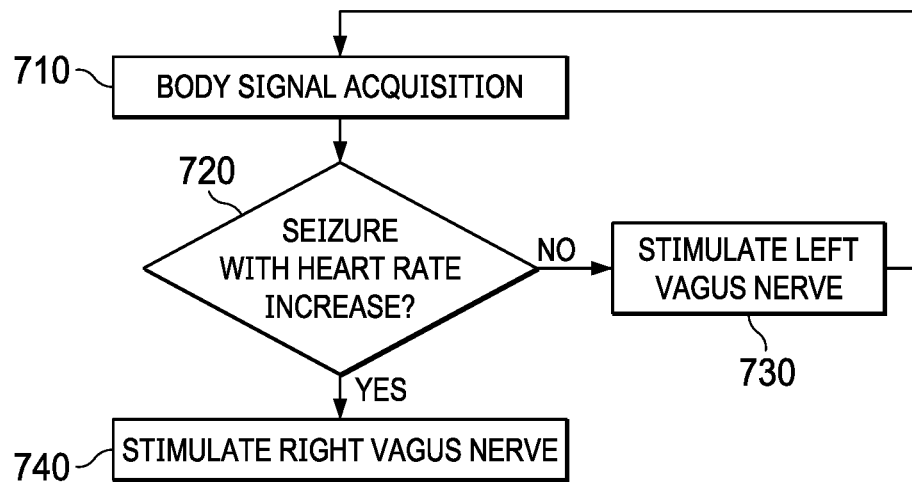
FIG. 7 is a flowchart depiction of a method for providing closed-loop vagus nerve stimulation for a patient with epilepsy by stimulating a right vagus nerve in response to detecting a seizure with tachycardia and stimulating a left vagus nerve in the absence of such a detection. For example if a recumbent person's heart rate is 55 bpm and it increases to 85 during a seizure, this is not clinical/pathological tachycardia, but may be considered tachycardia within the meaning of some embodiments of the present disclosure.

FIG. 7 is a flow diagram of a method of treating patients having seizures accompanied by increased heart rate. In one embodiment, tachycardia is defined as a neurogenic increase in heart rate, that is, an elevation in heart rate that occurs in the absence of motor activity or that if associated with motor activity, the magnitude of the increase in heart rate is larger than that caused by motor activity alone. In one embodiment, a body signal is acquired (710). The body signal may comprise one or more body signals that may be altered, changed or influenced by an epileptic seizure. As non-limiting examples, the body signal may comprise one or more of a cardiac signal such as heart rate, heart rate variability, or EKG complex morphology, a kinetic signal such as an accelerometer signal, a postural signal or body position signal), blood pressure, blood oxygen concentration, skin resistivity or conductivity, pupil dilation, eye movement, EEG, reaction time or other body signals. The body signal may be a real-time signal or a stored signal for delayed or later analysis. It may be acquired, for example, from a sensor element (e.g., coupled to a processor), from a storage device in which the signal data is stored.

The method further comprises determining whether or not the patient is having and/or has had a seizure accompanied by an increase in heart rate (720). In one embodiment, the method comprises a seizure detection algorithm that analyzes the acquired body signal data and determines whether or not a seizure has occurred. In a particular embodiment, the method comprises an algorithm that analyzes one or more of a cardiac signal, a kinetic signal, a cognitive signal, blood pressure, blood oxygen concentration, skin resistivity or conductivity, pupil dilation, and eye movement to identify changes in the one or more signals that indicate a seizure has occurred. The method may comprise an output signal or data flag that may be asserted or set when the detection algorithm determines from the body signal(s) that the patient is having and/or has had a seizure.

The method also comprises determining (720) whether or not the seizure is accompanied by an increase in heart rate. In one embodiment, the body data signal comprises a heart beat signal that may be analyzed to determine heart rate. In some embodiments, the heart beat signal may be used by the seizure detection algorithm to determine whether a seizure has occurred, while in other embodiments seizures are not detected using heart rate. Regardless of how the seizure is detected, however, the method of FIG. 7 comprises determining whether a detected seizure event is accompanied by an increase in heart rate. The increase may be determined in a variety of ways, such as by an increase in an instantaneous heart rate above a reference heart rate (which may be a predetermined interictal value such as 72 beats per minute (bpm), or a real-time measure of central tendency for a time window, such as a 5 minute median or moving average heart rate). Additional details about identifying increases in heart rate in the context of epileptic seizures are provided in U.S. Pat. Nos. 5,928,272, 6,341,236, 6,587,727, 6,671,556, 6,961,618, 6,920,357, 7,457,665, as well as U.S. patent application Ser. Nos. 12/770,562, 12/771,727, 12/771,783, 12/884,051, 12/886,419, 12/896,525, 13/098,262, and 13/288,886, each of which is hereby incorporated by reference in its entirety herein.

If the body data signal does not indicate that the patient is having and/or has had a seizure accompanied by tachycardia, the method comprises applying a first electrical signal to a left vagus nerve. If the body signal does indicate that the patient has experienced a seizure accompanied by tachycardia, the method comprises applying a second electrical signal to a right vagus nerve.

Without being bound by theory, it is believed that stimulation of the right vagus nerve, which enervates the right sinoatrial nerve that functions as the heart's natural pacemaker, will have a more prominent effect in slowing the heart rate than stimulation of the left vagus nerve. The present disclosure takes advantage of this electrical asymmetry of the left and right vagus nerves to minimize the effect of VNS on heart rate except where there is a need for acute intervention to slow the heart rate, i.e., when the patient has experienced and epileptic seizure, and the seizure is accompanied by an increase in heart rate. This may result in, for example, stimulation of the left vagus nerve either when there is no seizure (such as when an open-loop stimulation program off-time has elapsed and the program initiates stimulation in accordance with a programmed signal on-time), or when there is a detected seizure event that is not accompanied by an increase in heart rate (such as absence seizures); and stimulation of the right vagus nerve when there is a detected seizure event accompanied by a heart rate increase. In one embodiment, a programmed, open-loop electrical signal is applied to the left vagus nerve except when an algorithm analyzing the acquired body signal detects a seizure accompanied by a heart rate increase. In response to such a detection, a closed-loop electrical signal is applied to the right vagus nerve to slow the patient's (increased) heart rate. In some embodiments, the response to detecting a seizure accompanied by a heart rate increase may also include interrupting the application of the programmed-open-loop electrical signal to the left vagus nerve. The interrupted open-loop stimulation of the left vagus nerve may be resumed either when the seizure ends or the heart rate returns to a desired, lower heart rate.

In an additional embodiment of the disclosure, electrode pairs may be applied to each of the left and right vagus nerves of the patient, and used depending upon whether or not seizures accompanied by cardiac changes such as tachycardia are detected.

Figure 8:
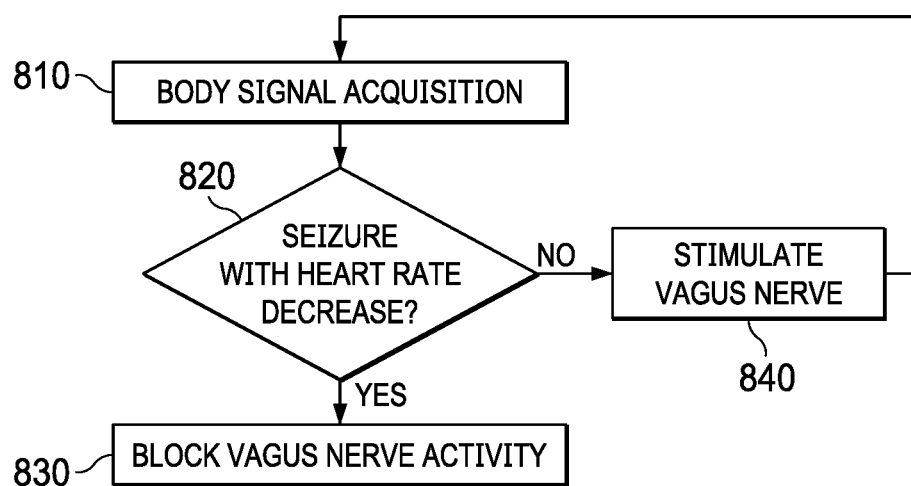
FIG. 8 is a flowchart depiction of a method for providing a closed-loop therapy to a vagus nerve of a patient with epilepsy in response to detecting a seizure associated with a heart rate decrease, wherein said therapy blocks impulse conduction along at least one vagus nerve.

FIG. 8 is a flowchart depiction of a method of treating patients having seizures accompanied by a relative or absolute decrease in heart rate (i.e., a bradycardia episode). Epileptic seizures originating from certain brain regions may trigger decreases in heart rate of a magnitude sufficient to cause loss of consciousness and of postural tone (i.e., syncope). In some subjects the cerebral ischemia associated with the bradycardia may in turn lead to convulsions (i.e., convulsive syncope). If bradycardia-inducing seizures are not controllable by medications, the current treatment is implantation of a demand cardiac pacemaker. In one embodiment of the present disclosure, ictal bradycardia may be treated by preventing vagal nerve impulses from reaching the heart, either by preventing impulses traveling through all fiber types contained in the trunk of the nerve or in one of its branches, or by only blocking impulses within a certain fiber type. In another embodiment, the degree of the nerve impulse blocking within a vagus nerve may be determined based upon the magnitude of bradycardia (e.g., the larger the bradycardia change from the pre-existing baseline heart rate, the larger the magnitude of the block) so as to prevent tachycardia from occurring.

In one embodiment, a body signal is acquired (810). The body signal may comprise one or more body signals that may be altered, changed or influenced by an epileptic seizure. Changes in the body signal may be used to detect the onset or impending onset of seizures. As noted with reference to FIG. 7, the body signal may comprise one or more measure derived from a cardiac signal (e.g., heart rate, heart rate variability, change in EKG morphology), a kinetic signal (e.g., an accelerometer, force of muscle contraction, posture or body position signal), blood pressure, blood oxygen concentration, skin resistivity/conductivity, pupil dilation, eye movement, or other body signals. The body signal may be a real-time signal, a near-real-time signal, or a non-real-time signal, although in preferred embodiments, the signal is a real-time signal or a near-real-time signal. The signal may be acquired from a sensor element (e.g., coupled to a processor) or from a storage device.

Referring again to FIG. 8, the method further comprises determining whether or not the patient is having and/or has had a seizure that is accompanied by a decrease in heart rate (820). In one embodiment, the method comprises using a seizure detection algorithm using one or more of a cardiac, kinetic, neurologic, endocrine, metabolic or tissue stress marker to detect seizures, and to determine if the seizure is associated with a decrease in heart rate. In a particular embodiment, an algorithm-which may comprise software and/or firmware running in a processor in a medical device-analyzes one or more of a cardiac signal, a kinetic signal, blood pressure, blood oxygen concentration, skin resistivity or conductivity, pupil dilation, and eye movement to identify changes in the one or more signals that indicate the occurrence of an epileptic seizure. Such changes may be identified by determining one or more indices from the foregoing signals, such as a cardiac index (e.g., a heart rate), a kinetic index (e.g., a kinetic level or motion type, a magnitude of an acceleration or force, or other indices that may be calculated from an accelerometer signal). The method may include providing an output signal or setting a data flag when the detection algorithm determines from the body signal(s) that the patient is having and/or has had a seizure. In a preferred embodiment, the seizure detection occurs in real time and the output signal or data flag is set immediately upon detection of the seizure.

Once it is determined that the patient is having and/or has had a seizure, the method also comprises determining if the seizure is accompanied by a decrease in heart rate. In one embodiment, the acquired body data signal (810) comprises a heart beat signal that may be analyzed to determine heart rate. In some embodiments, the acquired heart beat signal may be used by the seizure detection algorithm to determine whether a seizure has occurred, while in other embodiments seizures are determined without regard to the patient's heart rate. Regardless of how the seizure is determined, the method of FIG. 8 comprises determining whether a detected seizure event is accompanied by a decrease in heart rate (820). The decrease in heart rate may be determined in a variety of ways, such as by a decrease in an instantaneous heart rate below a reference heart rate value (which may be a predetermined interictal value such as 72 beats per minute (bpm), or a real-time measure of central tendency for a time window or number-of-beats window (e.g., a 5 minute median or moving average heart rate, or a media heart rate for a window selected from 3-300 beats such as a 5, 10, or 300 beat window)). Additional details about identifying decreases in heart rate in the context of epileptic seizures are provided in U.S. patent application Ser. Nos. 12/770,562, 12/771,727, 12/771,783, 12/884,051, 12/886,419, 13/091,033, each of which is hereby incorporated by reference in its entirety herein.

In one embodiment, if the acquired body data signal does not indicate that the patient is having and/or has had a seizure accompanied by a HR decrease, the method comprises applying a first electrical signal to a vagus nerve (840), wherein the first electrical signal is sufficient to generate exogenous action potentials in fibers of the vagus nerve. The second electrical signal is a therapeutic electrical signal to treat the seizure. It may be applied to either the left or right vagus nerves, or both. The first electrical signal may be a signal defined by, among other parameters, an on-time during which electrical pulses are applied to the nerve, and an off-time during which no pulses are applied to the nerve. In some embodiments, the on-time may be determined by the duration and intensity of the change in heart rate, while in other embodiments it may be pre-programmed. Cathode(s) and anode(s) may be placed on the nerve trunks or branches to maximize flow of exogenously generated nerve impulses in a caudal direction (for control of heart rate changes) and a cephalic direction for seizure treatment.

If the body signal indicates that the patient is having and/or has had a seizure accompanied by a decrease in heart rate, the method comprises applying an action to decrease vagal/parasympathetic tone. In one embodiment, the method comprises blocking the passage of impulses through at least one of a vagus nerve trunk or branch. This may be accomplished by applying one or more of a second electrical signal (e.g., a high frequency electrical signal), a thermal signal (e.g., cooling), a chemical signal (e.g., applying a local anesthetic), and/or a mechanical signal (e.g., applying pressure or a vibration) to a vagus nerve of the patient (830). In another embodiment, the method comprises delivering at least one of an anti-cholinergic drug or a sympatho-mimetic drug.

As used herein, blocking vagus nerve activity means blocking intrinsic or native vagal activity (i.e., blocking action potentials not artificially or exogenously induced by an electrical signal generated by a device). The blocking signal may block the conduction of action potentials in all or at least some portion or fraction of the axons of a vagus nerve. In general, such blocking signals are incapable of inducing exogenous action potentials in the axons of the vagus nerve. In one embodiment, the blocking signal may comprise a high frequency, pulsed electrical signal, the pulse frequency being sufficient to inhibit propagation of at least some action potentials in vagus nerve fibers. The electrical signal may comprise a signal in excess of 300 Hz, or other frequency, so long as the frequency and other stimulation signal parameters (such as pulse width and pulse current or voltage) provide a signal capable of inhibiting some or all of the action potentials propagating along fibers of the vagus nerve. In alternative embodiments, the electrical signal may comprise generating unidirectional action potentials for collision blocking of endogenous action potentials.

High frequency vagus nerve stimulation (or other blocking signals such as collision blocking) may inhibit pathological vagus nerve activity associated with the seizure that may be acting to slow the patient's heart rate. By providing such stimulation only when the patient experiences a seizure accompanied by a reduced heart rate (e.g., bradycardia), a therapy may be provided that acts to maintain the patient's heart rate when the patient experiences a seizure involving excessive vagal activity—and consequent undesired slowing of—the heart. In one embodiment, the blocking electrical signal (830) is provided to a right vagus nerve. Without being bound by theory, because the right vagus nerve innervates the right sinoatrial node that functions as the heart's natural pacemaker, it is believed that right-side VNS will have a more significant effect upon the heart rate than stimulation of the left vagus nerve. In alternative embodiments, the blocking signal may be applied to the left vagus nerve, to both the right and left vagus nerves, or to one or both of the left and right cardiac branches of the vagus nerves.

In one embodiment, the method comprises applying a first electrical signal that may be a conventional vagus nerve stimulation signal defined by a plurality of parameters (e.g., a pulse width, a current magnitude, a pulse frequency, an on-time and an off-time). A seizure detection algorithm (e.g., using one or more of a cardiac, kinetic, metabolic, EEG, or other body signal) may be used to detect seizures, and the patient's heart rate may be determined proximate the seizure detection to determine if the seizure is accompanied by a decrease in the patient's heart rate. If the seizure is accompanied by a slowing of the patient's heart rate, the first electrical signal may be suspended, and a second electrical signal may be applied to slow the patient's heart rate. The method may further include sensing the patient's heart rate during or after application of the second electrical signal. In one embodiment, the second electrical signal may be modified (e.g., by changing current magnitude, pulse width, or pulse frequency), or suspended (and possibly resumed) to maintain the patient's heart rate between an upper heart rate threshold and a lower heart rate threshold. In some embodiments, the upper and lower heart rate thresholds may be dynamically set (e.g., as no more than 5 bpm above or below the baseline HR prior to the seizure detection).

Figure 9:
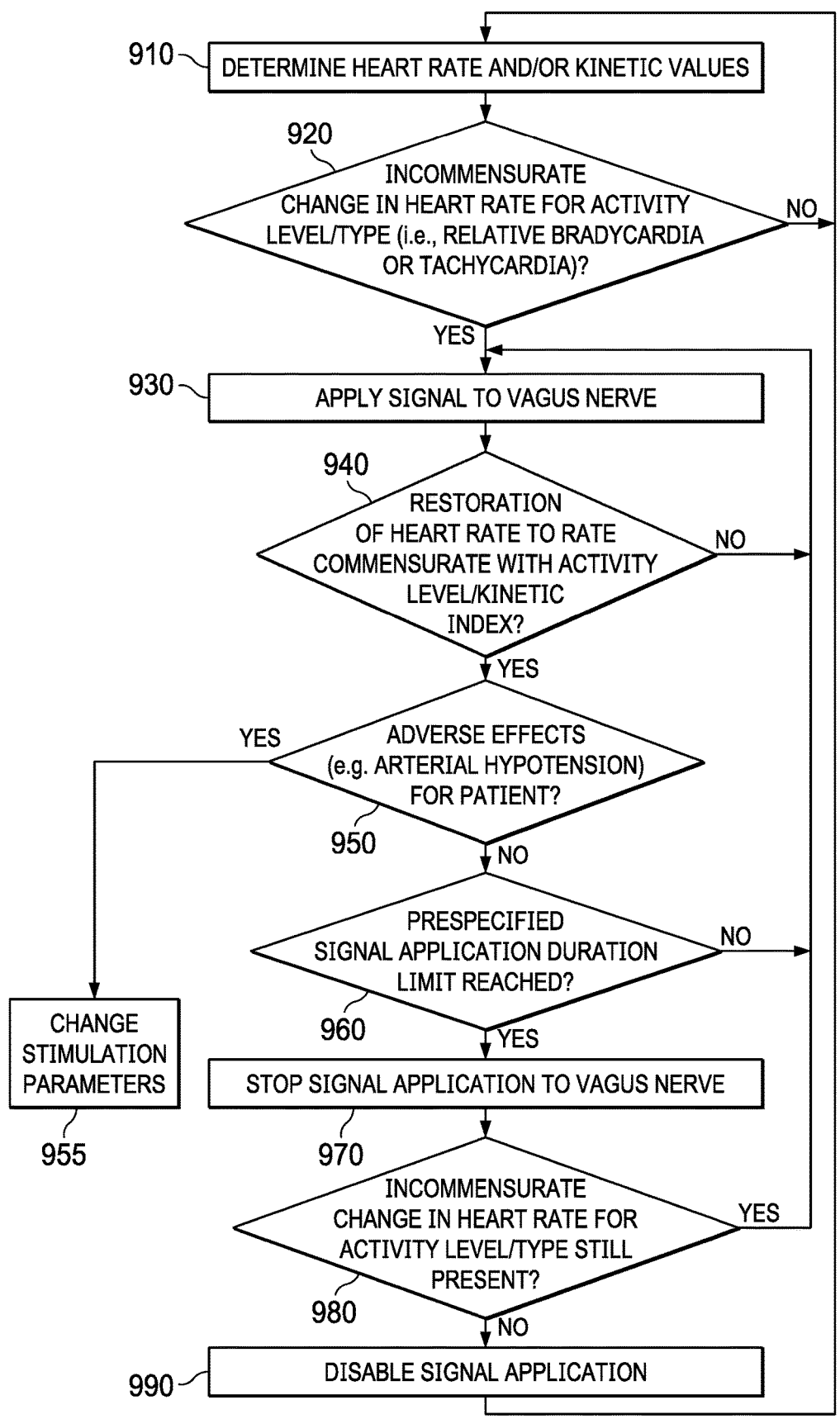
FIG. 9 is a flowchart depicting a method for providing closed-loop vagus nerve stimulation based on an assessment of whether the patient's heart rate is commensurate with the patient's activity level or activity type.

FIG. 9 is a flow diagram of a method of treating a patient with epilepsy by providing closed-loop vagus nerve intervention (e.g., stimulation or blockage of impulse conduction) to maintain the patient's heart rate within a range that is both safe and also commensurate with the activity type or level and state of the patient (e.g., as determined from a kinetic signal from a sensing element such as a triaxial accelerometer or by measuring oxygen consumption). In one embodiment, the method comprises providing vagus nerve stimulation in response to determining that a heart rate is incommensurate with the kinetic signal of the patient, to restore cardiac function to a rate that is commensurate with the patient's kinetic signal. In one embodiment, the stimulation may comprise stimulating a right vagus nerve to slow the patient's heart rate to a level that is safe and/or commensurate with activity level. In another embodiment, the stimulation may comprise providing a blocking signal to increase a slow heart rate to a rate that is safe and/or commensurate with the activity level. Pharmacologic compounds (e.g., drugs) with sympathetic or parasympathetic effects (e.g., enhancing or blocking sympathetic or parasympathetic activity) may be used to restore heart rate to a rate commensurate with kinetic activity of the patient in still other embodiments. In one embodiment, the method involves determining a heart rate and one or more kinetic or metabolic (e.g., oxygen consumption) indices for the patient (910). Heart rate may be determined from an acquired cardiac signal (e.g., from a sensor or stored data). Kinetic and/or metabolic indices may likewise be determined from a kinetic sensor (e.g., an accelerometer, a positional sensor, a GPS device coupled to a clock, or a postural sensor), a metabolic sensor, or from stored data. Sensor data may be subjected to one or more operations such as amplifying, filtering, A/D conversion, and/or other pre-processing and processing operations to enable determination of heart rate (and in some embodiments other cardiac indices such as heart rate variability) and kinetic indices.

The activity level of the patient may be determined from multiple kinetic indications such as an activity level, a type of activity, a posture, a body position, a trunk or limb acceleration or force, or a duration of one of the foregoing, and may be adapted or modified as a function of age, gender, body mass index, fitness level or time of day or other indices of the patient's condition or environment. For example, the kinetic signal may be processed to provide indices that indicate moderate ambulatory motion for an upright patient, vigorous physical exercise (in which the patient may be upright as in running or in a prone position as in some calisthenics exercises), a fall (e.g., associated with a seizure), reclining, resting or sleeping, among other activity levels and kinetic states.

The one or more kinetic indices may then be used to determine (e.g., by retrieving stored data from a lookup table or by calculation using an algorithm) one or more heart rate ranges or values that would be commensurate with the kinetic activity and/or kinetic state, duration, time of day, etc. associated with the indices. In some embodiments, heart rate ranges may be established for particular levels or types of activity (e.g., running, walking), that may be adaptively adjusted depending upon various factors such as the duration of the activity, the patient's fitness level, the time of day, a level of fatigue, an environmental temperature, etc. A commensurate heart rate is one that is within expected ranges or values for the person's effort, and for factors inherent to the patient and the environment.

Returning to FIG. 9, the determined heart rate may be compared to the range(s)/value(s) identified as commensurate with the kinetic indices (920) at a given time point. If the actual heart rate of the patient is within the expected/commensurate range or value associated with the kinetic or metabolic indices at the time point, or is within a specified proximity of a particular range or value, no action may be taken, and the method may involve continuing to analyze the patient's cardiac and kinetic signals or metabolic signals. On the other hand, if the heart rate is outside the expected value or range of values for the kinetic or metabolic indices for that time point, then the heart rate is not commensurate with the kinetic signal of the patient, and a therapy may be provided to the patient by applying one of an electrical, thermal, mechanical or chemical signal to a vagus nerve of the patient (930) or administering to the patient (e.g., intravenously, through mucosae) a drug with cholinergic or anti-cholinergic or adrenergic actions, depending on the case or situation. In one embodiment, the method may comprise applying the signal to a main trunk of a vagus nerve of the patient, and in another embodiment, the signal may be applied to a cardiac branch of a vagus nerve.

In one embodiment, the heart rate of the patient may be higher than a value commensurate with the activity level or kinetic indices of the patient. In this case, the patient is having relative tachycardia. Where this is the case, as previously noted, vagus nerve stimulation may be applied to one or more of a right cardiac branch, left cardiac branch, or right main trunk of the patient's vagus nerve to reduce the patient's heart rate to a rate that is commensurate with the activity level. Embodiments of the disclosure may be used to treat epileptic seizures associated with tachycardia, and other medical conditions associated with tachycardia given the patient's activity level. Therapies (e.g., electrical, chemical, mechanical, thermal) delivered to a patient via the vagus nerves may be employed for tachyarrythmias, angina pectoris or pain in regions innervated by a vagus nerve.

In another embodiment, the patient's heart rate may be lower than a value commensurate with the patient's activity level or kinetic indices, that is, the patient is having relative or absolute bradycardia. High frequency (>>300 Hz) electrical pulses may be applied to the left or right vagus nerves (e.g., a main trunk of the right and/or left vagus nerves or to their cardiac branches) to block propagation of transmission of nerve impulses through their fibers. High-frequency VNS may be applied to block impulses traveling to the heart to abate neurogenic, cardiogenic or iatrogenic bradycardia, or to minimize the cumulative effects on the heart's conduction system and myocardium of epileptic seizures, especially in status epilepticus. Selective blockage of impulses traveling through a vagus nerve to the heart may be accomplished with electrical stimulation to treat adverse cardiac effects associated with disorders such as epilepsy, depression, diabetes or obesity. By blocking vagus nerve conduction to the heart, when the patient's heart rate is incommensurate with the activity level or kinetic indices, a therapy may be provided to revert the change in heart rate (whether the change involves bradycardia or tachycardia). In one embodiment, an electrical signal generator may be used to apply a first therapy signal to a vagus nerve of the patient, and an electrical signal generator (which may be the same or a different electrical signal generator) may apply a vagus nerve conduction blocking electrical signal to a vagus nerve (e.g., a cardiac branch of the vagus nerve) to block cardiac effects that would result from the first electrical signal, absent the vagus nerve conduction blocking electrical signal.

Referring again to FIG. 9, the method may comprise determining the patient's heart rate in response the therapy to determine whether the heart rate has been restored to a rate that is with commensurate with the patient's activity level/kinetic index (940). If not, then the therapy (e.g., VNS to reduce or increase heart rate to an appropriate value) may be continued, with or without parameter modification, or re-initiated after a delay period or confirmation period.

If the heart rate has returned to a range/value commensurate with the activity level of the patient, the method may, in some embodiments, further involve determining whether or not an adverse event has occurred (950). Adverse events may include, without limitation, side effects such as voice alteration, pain, difficulty breathing or other respiratory effects, adverse cardiac effects such as bradycardia (following a determination of relative tachycardia in step 920), tachycardia (following a determination of bradycardia in step 920), and alteration in blood pressure or gastro-intestinal activity.

If an adverse event has occurred, the method may involve changing one or more stimulation parameters to eliminate, reduce or ameliorate the adverse event (955). If no adverse event has occurred, the method may comprise continuing to apply a signal the vagus nerve until a predetermined signal application duration has been reached (960), at which time the signal application may be stopped (970). The method may further comprise determining, after the therapy has been stopped, if the patient's heart rate remains incommensurate with the patient's activity level or type (980), in which case the signal application may be resumed or other appropriate action may be taken (e.g., local or remote alarms or alerts, notification of caregivers/healthcare providers, etc.). If the heart rate has returned to a value that is commensurate or appropriate for the patient's activity level, the signal application may be discontinued (990).

Figure 10:
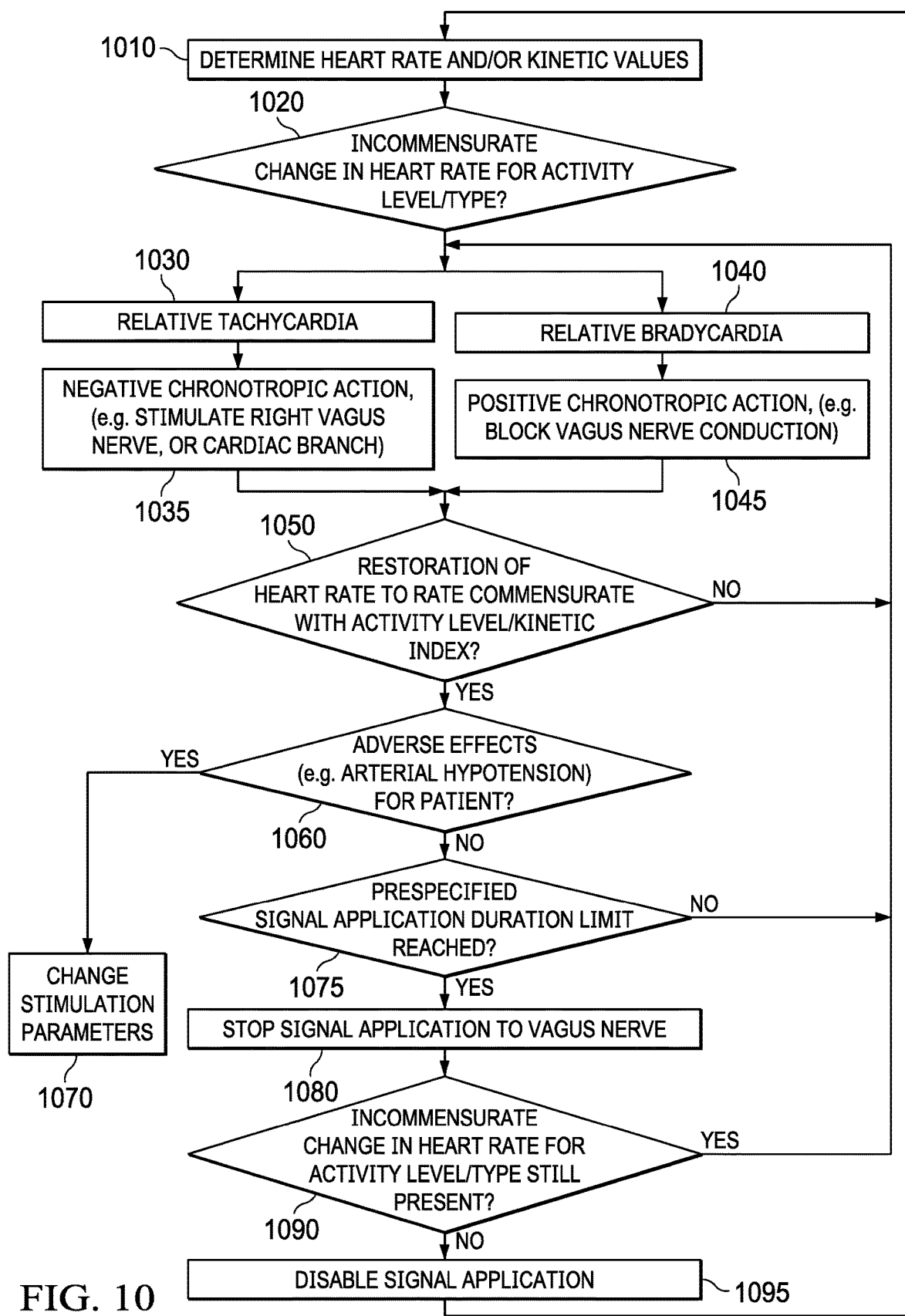
FIG. 10 is a flowchart depicting a method for providing closed-loop vagus nerve stimulation based on a determination that the patient's heart rate is incommensurate with the patient's activity level or activity type, and further in view of whether the incommensurate changes involves relative tachycardia or relative bradycardia.

FIG. 10 is a flow diagram of a method of treating a patient to with epilepsy by providing closed-loop vagus nerve stimulation to treat relative tachycardia or relative bradycardia by restoring the patient's heart rate to a rate that is commensurate with the activity type or level of the patient (e.g., as determined from a kinetic signal from a sensing element such as a triaxial accelerometer or by measuring oxygen consumption). In one embodiment, the method comprises identifying instances of relative tachycardia or relative bradycardia and responding with negative or positive chronotropic actions to restore the heart rate to a level commensurate with the patient's activity type or level.

In one embodiment, the method involves determining a heart rate and an activity type or level for the patient (1010). The patient's heart rate may be determined from an acquired cardiac signal or from stored data. The activity level or type of the patient may be determined from one or more sensor or from stored data. Sensors may include, for example, accelerometers, positional sensors, GPS devices coupled to a clock, postural sensors, and metabolic sensors. Sensor data may be subject to conventional signal processing, and may in addition be adapted or modified as a function of age, gender, body mass index, fitness level or time of day or other indices of the patient's condition or environment.

The patient's activity type or level may then be used to determine one or more heart rate ranges or values that are commensurate with the activity type or level (1020). In some embodiments, heart rate ranges may be established for particular levels or types of activity (e.g., running, walking), that may be adaptively adjusted depending upon various factors such as the duration of the activity, the patient's fitness level, the time of day, a level of fatigue, an environmental temperature, etc. A commensurate heart rate is one that is within expected ranges or values for the person's effort, and for factors inherent to the patient and the environment.

If the heart rate is commensurate with the activity level, in one embodiment no action may be taken, and the method may involve continuing to analyze the patient's cardiac and activity. On the other hand, if the heart rate is outside the identified value or range of values appropriate for the patient's activity type or level then the heart rate is not commensurate with the kinetic signal of the patient. Where this is the case, the method may further comprise determining whether the patient is experiencing relative tachycardia or is experiencing relative bradycardia (1030, 1040).

Where the heart rate of the patient is higher than a value commensurate with the activity level or type, the patient is experiencing relative tachycardia (1030), and the method may comprise initiating a negative chronotropic action (1035) to slow the heart rate to a rate that is commensurate with the activity level or type. In one embodiment, this may involve applying stimulation to one or more of a left or right main vagal trunk or cardiac branch of the patient. In other embodiments, the method may comprise providing a drug to enhance the parasympathetic tone of the patient. In still other embodiments, the method may comprise reducing the patient's sympathetic tone, such as by applying high-frequency stimulation to a sympathetic nerve trunk or ganglion or administering an anti-cholinergic drug. Negative chronotropic actions may be used to treat epileptic seizures associated with tachycardia, and other medical conditions associated with relative tachycardia given the patient's activity level.

Where the heart rate of the patient is lower than a value commensurate with the activity level or type, the patient is experiencing relative bradycardia (1040), and the method may comprise initiating a positive chronotropic action (1045) to increase the heart rate to a rate that is commensurate with the activity level or type. In one embodiment, this may involve applying high-frequency (>>300 Hz) electrical stimulation to one or more of a left or right main vagal trunk or cardiac branch of the patient to reduce the transmission of intrinsic vagus nerve action potentials in at least some vagal fibers. In other embodiments, the method may comprise providing a drug to reduce the parasympathetic tone of the patient. In still other embodiments, the method may comprise increasing the patient's sympathetic tone, such as by applying electrical signals to a sympathetic nerve trunk or ganglion or by administering a sympatho-mimetic drug. Positive chronotropic actions may be used to treat epileptic seizures associated with bradycardia, and other medical conditions associated with relative bradycardia given the patient's activity level.

The method may further comprise, after initiating the negative or positive chronotropic action, determining whether the patient's heart rate has been restored to a rate that is with commensurate with the patient's activity level/kinetic index (1050). If not, then the therapy (e.g., VNS to reduce or increase heart rate to an appropriate value) may be continued, with or without parameter modification, or re-initiated after a delay period or confirmation period.

If the heart rate has returned to a range/value commensurate with the activity level of the patient, the method may, in some embodiments, further involve determining whether or not an adverse event has occurred (1060). Adverse events may include, without limitation, side effects such as voice alteration, pain, difficulty breathing or other respiratory effects, adverse cardiac effects such as bradycardia (following a determination of relative tachycardia in step 1030), or tachycardia (following a determination of bradycardia in step 1040), and alteration in blood pressure or gastric activity.

If an adverse event has occurred, the method may involve changing one or more stimulation parameters to eliminate, reduce or ameliorate the adverse event (1070). If no adverse event has occurred, the method may comprise continuing to stimulate the vagus nerve (or a chemical, thermal or mechanical therapy) until a predetermined stimulation duration has been reached (1075), at which time the stimulation may be stopped (1080). The method may further comprise determining, after the therapy has been stopped, if the patient's heart rate remains incommensurate with the patient's activity level or type (1090), in which case the stimulation may be resumed or other appropriate action may be taken (e.g., local or remote alarms or alerts, notification of caregivers/healthcare providers, use of other forms of therapy, etc.). If the heart rate has returned to a value that is commensurate or appropriate for the patient's activity level, the stimulation may be discontinued (1095).

Additional embodiments consistent with the foregoing description and figures may be made. Non-limiting examples of some such embodiments are provided in the numbered paragraphs below.

100. A method of controlling a heart rate of an epilepsy patient comprising:
   sensing at least one of a kinetic signal and a metabolic signal of the patient;
   analyzing the at least one of a kinetic and a metabolic signal to determine at least one of a kinetic index and a metabolic index;
   receiving a cardiac signal of the patient;
   analyzing the cardiac signal to determine the patient's heart rate;
   determining if the patient's heart rate is commensurate with the at least one of a kinetic index and a metabolic index; and
   applying an electrical signal to a vagus nerve of the patient based on a determination that the patient's heart rate is not commensurate with the at least one of a kinetic signal and a metabolic signal of the patient.

101. The method of numbered paragraph 100, wherein determining at least one of a kinetic index and a metabolic index comprises determining at least one of an activity level or an activity type of the patient based on the at least one of a kinetic index and a metabolic index, and
   wherein determining if the patient's heart rate is commensurate with the at least one of a kinetic index and a metabolic index of the patient comprises determining if the heart rate is commensurate with the at least one of an activity level or an activity type.

102. The method of numbered paragraph 101, wherein determining if the patient's heart rate is commensurate with the at least one of a kinetic index and a metabolic index comprises determining if the patient's heart rate is above or below a rate that is commensurate with the one or more of a kinetic index and a metabolic index.

103. A method of treating a patient having epilepsy comprising
   sensing at least one body signal of the patient;
   determining whether or not the patient is having or has had an epileptic seizure based on the at least one body signal;
   sensing a cardiac signal of the patient;
   determining whether or not the seizure is associated with a change in the patient's cardiac signal;
   applying a first therapy to a vagus nerve of the patient based on a determination that the patient is having or has had an epileptic seizure that is not associated with a change in the patient's cardiac signal, wherein the first therapy is selected from an electrical, chemical, mechanical, or thermal signal; and
   applying a second therapy to a vagus nerve of the patient based on a determination that the patient is having or has had an epileptic seizure associated with a change in the patient's cardiac signal, wherein the second therapy is selected from an electrical, chemical, mechanical (e.g., pressure) or thermal signal.

104. The method of numbered paragraph 103, further comprising
   applying a third therapy to a vagus nerve of the patient based a determination that the patient is not having or has not had an epileptic seizure, wherein the third therapy is selected from an electrical, chemical, mechanical or thermal signal.

105. A method of treating a patient having epilepsy comprising:
   coupling a first set of electrodes to a main trunk of the left vagus nerve of the patient;
   coupling a second set of electrodes to a main trunk of the right vagus nerve of the patient;
   providing an electrical signal generator coupled to the first electrode set and the second electrode set;
   receiving at least one body data stream;
   analyzing the at least one body data stream using a seizure detection algorithm to determine whether or not the patient is having and/or has had an epileptic seizure;
   applying a first electrical signal from the electrical signal generator to the main trunk of the left vagus nerve, based on a determination that the patient is having and/or has had an epileptic seizure without a heart rate change; and
   applying a second electrical signal from the electrical signal generator to the main trunk of the right vagus nerve, based on a determination that the patient is having or has had an epileptic seizure with a heart rate change.

106. A method of treating a patient having epilepsy comprising:
   receiving at least one body data stream;
   analyzing the at least one body data stream using a seizure detection algorithm to detect whether or not the patient has had an epileptic seizure;
   receiving a cardiac signal of the patient;
   analyzing the cardiac signal to determine a first cardiac feature;
   applying a first electrical signal to a vagus nerve of the patient, based on a determination that the patient has not had an epileptic seizure characterized by a change in the first cardiac feature, wherein the first electrical signal is not a vagus nerve conduction blocking electrical signal; and
   applying a second electrical signal to a vagus nerve of the patient, based on a determination that the patient has had an epileptic seizure characterized by a change in the cardiac feature, wherein the second electrical signal is a pulsed electrical signal that blocks action potential conduction in the vagus nerve.

107. A method of treating a patient having epilepsy comprising:
   receiving at least one body data stream;
   analyzing the at least one body data stream using a seizure detection algorithm to detect whether or not the patient has had an epileptic seizure;
   receiving a cardiac signal of the patient;
   analyzing the cardiac signal to determine a first cardiac feature;
   applying a first electrical signal to a vagus nerve of the patient, based on a determination that the patient has not had an epileptic seizure characterized by a change in the first cardiac feature, wherein the first electrical signal is a pulsed electrical signal that blocks action potential conduction in the vagus nerve; and applying a second electrical signal to a vagus nerve of the patient, based on a determination that the patient has had an epileptic seizure characterized by a change in the cardiac feature, wherein the second electrical signal is not a vagus nerve conduction blocking electrical signal.

Figure 11:
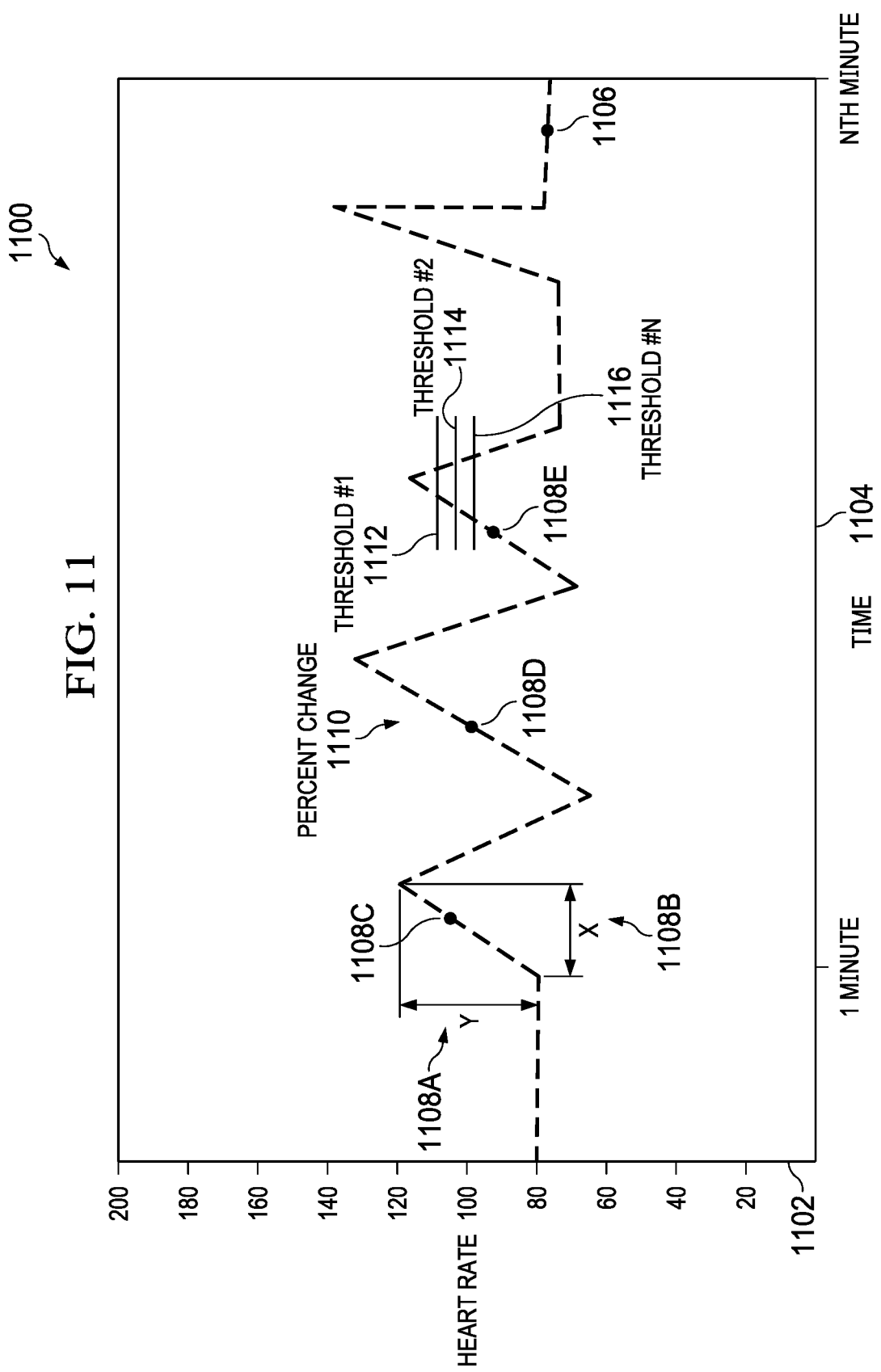
FIG. 11 is a graph of heart rate versus time, according to one embodiment.

In FIG. 11, a graph of heart rate versus time is shown, according to one embodiment. A first graph 1100 includes a y-axis 1102 which represents heart rate where the heart rate goes from a zero value to an Nth value (e.g., 200 heart beats, etc.). Further, the first graph 1100 includes an x-axis 1104 which represents time from 1 minute to Nth minutes (and/or 0.001 seconds to Nth seconds). In this example, a first heart rate versus time line 1106 for the patient is shown. In this example, the patient's heart rate goes from 80 heart beats per minute to 118 heart beats per minute with a first rise 1108A and a first run 1108B during a first event 1108C. In addition, the patient's heart rate goes from 70 heart beats per minute to 122 heart beats per minute during a second event 1108D which has a first percentage change 1110 associated with the second event 1108D. Further, the patient's heart rate goes from 70 beats per minute to 113 beats per minute during an nth event 1108E which surpasses a first threshold amount 1112, and/or a second threshold amount 1114, and/or an Nth threshold amount 1116. In one example, only the Nth threshold amount 1116 needs to be reached to trigger a therapy and/or an alert. In another example, only the second threshold amount 1114 needs to be reached to trigger a therapy and/or an alert. In another example, only the first threshold 1112 needs to be reached to trigger a therapy and/or an alert. In another example, both the Nth threshold 1116 and the second threshold 1114 need to reached to trigger a therapy and/or an alert. In another example, all of the Nth threshold 1116, the second threshold 1114 and the first threshold 1112 need to reached to trigger a therapy and/or an alert. In one example, only the Nth threshold amount 1116 needs to be reached during a specific time period to trigger a therapy and/or an alert. In another example, only the second threshold amount 1114 needs to be reached during a specific time period to trigger a therapy and/or an alert. In another example, only the first threshold 1112 needs to be reached during a specific time period to trigger a therapy and/or an alert. In another example, both the Nth threshold 1116 and the second threshold 1114 need to reached during a specific time period to trigger a therapy and/or an alert. In another example, all of the Nth threshold 1116, the second threshold 1114 and the first threshold 1112 need to reached during a specific time period to trigger a therapy and/or an alert. In these examples, one or more triggering events may occur based on a determination of the rise and run of a change in heart rate, a percentage change in heart rate, a threshold amount being reached or exceeded (or within any percentage of the threshold), and/or any combination thereof. A triggering event may initiate one or more actions to increase and/or decrease the patient's heart rate. For example, if the patient's heart rate is increasing which determines the triggering event, then the system, device, and/or method may initiate one or more actions to decrease the heart rate of the patient to help reduce, dampen, eliminate, and/or buffer the increase in the patient's heart rate. Further, the system, device, and/or method may oscillate between decreasing the patient's heart rate and increasing the patient's heart rate depending on any changes to the patient's heart rate. For example, the system, device, and/or method may initiate one or more actions to decrease a patient's heart rate based on the patient's heart rate going from 80 heart beats per minute to 130 heart beats per minute which results in the patient's heart rate falling from 130 heart beats per minute to 65 heart beats per minute in a first time period. Based on the change in the heart rate from 130 heart beats per minute to 65 heart beats per minute in the first time period, the system, device, and/or method may initiate one or more actions to increase the patient's heart rate and/or stabilize the patient's heart rate. In another example, the system, method, and/or device may stop and/or modify any initiated action based on one or more feedback signals. In addition, one or more warnings may be transmitted to the patient, a caregiver, a doctor, a medical professional, and/or logged.

Figure 12:
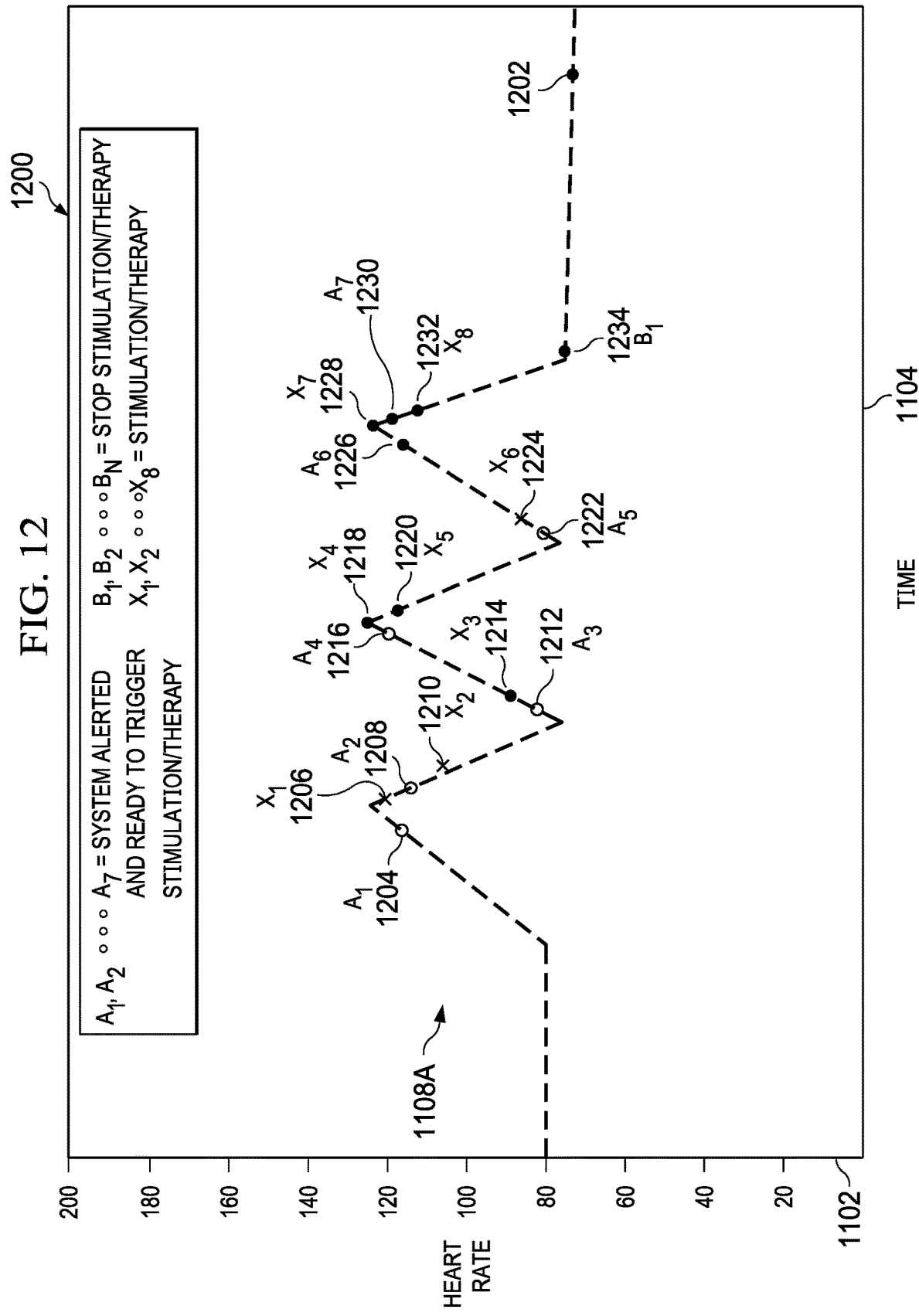
FIG. 12 is another graph of heart rate versus time, according to one embodiment.

In FIG. 12, another graph of heart rate versus time is shown, according to one embodiment. A second graph 1200 illustrating a second heart rate versus time line 1202 for the patient is shown. In this example, the patient's heart rate goes from 80 heart beats per minute to 120 heart beats per minute which creates a first system alert event 1204 (e.g., A1). Further, the system, device, and/or method initiates a first therapy 1206 (e.g., X1) based on the first system alert event 1204. In addition, a second system alert event 1208 (e.g., A2) occurs and a second therapy 1210 (e.g., X2) is initiated based on the second system alert event 1208. In addition, a third system alert event 1212 (e.g., A3) occurs and a third therapy (e.g., X3) 1214 is initiated based on the third system alert event 1212 (e.g., A3). In addition, a fourth system alert event 1216 (e.g., A4) occurs and a fourth therapy 1218 (e.g., X4) is initiated based on the fourth system alert event 1216 (e.g., A3). Further, a fifth therapy 1220 (e.g., X5) is initiated based on the effects of the fourth therapy 1218 (e.g., X4). In addition, a fifth system alert event 1222 (e.g., A5) occurs and a sixth therapy (e.g., X6) 1224 is initiated based on the fifth system alert event 1222 (e.g., A5). In addition, a sixth system alert event 1226 (e.g., A6) occurs and a seventh therapy (e.g., X7) 1228 is initiated based on the sixth system alert event 1226 (e.g., A6). In addition, a seventh system alert event 1230 (e.g., A7) occurs and an eighth therapy (e.g., X8) 1232 is initiated based on the seventh system alert event 1230 (e.g., A7). In addition, a first stop stimulation event 1234 (e.g., B1) occurs which turns off all therapies and/or system alerts may occur when the heart rate returns to the approximate starting heart rate and/or a target value. In these examples shown with FIG. 12, a rise over run heart rate calculation was completed to determine the one or more system alerts. However, it should be noted that any calculation (e.g., % increase, % decrease, etc. can be utilized). Further, all systems alerts and/or therapies may occur as independent events and/or examples. For example, the seventh system alert may be the first system alert in a specific example. In other words, no other events and/or therapies occurred before the seventh system alert. Therefore, the seventh system alert becomes the first system alert. In addition, one or more warnings may be transmitted to the patient, a caregiver, a doctor, a medical professional, and/or logged. In addition, there may be up to an Nth alerts, an Nth stop stimulation (and/or therapy) event, and an Nth therapy in any of the examples disclosed in this document.

Figure 13:
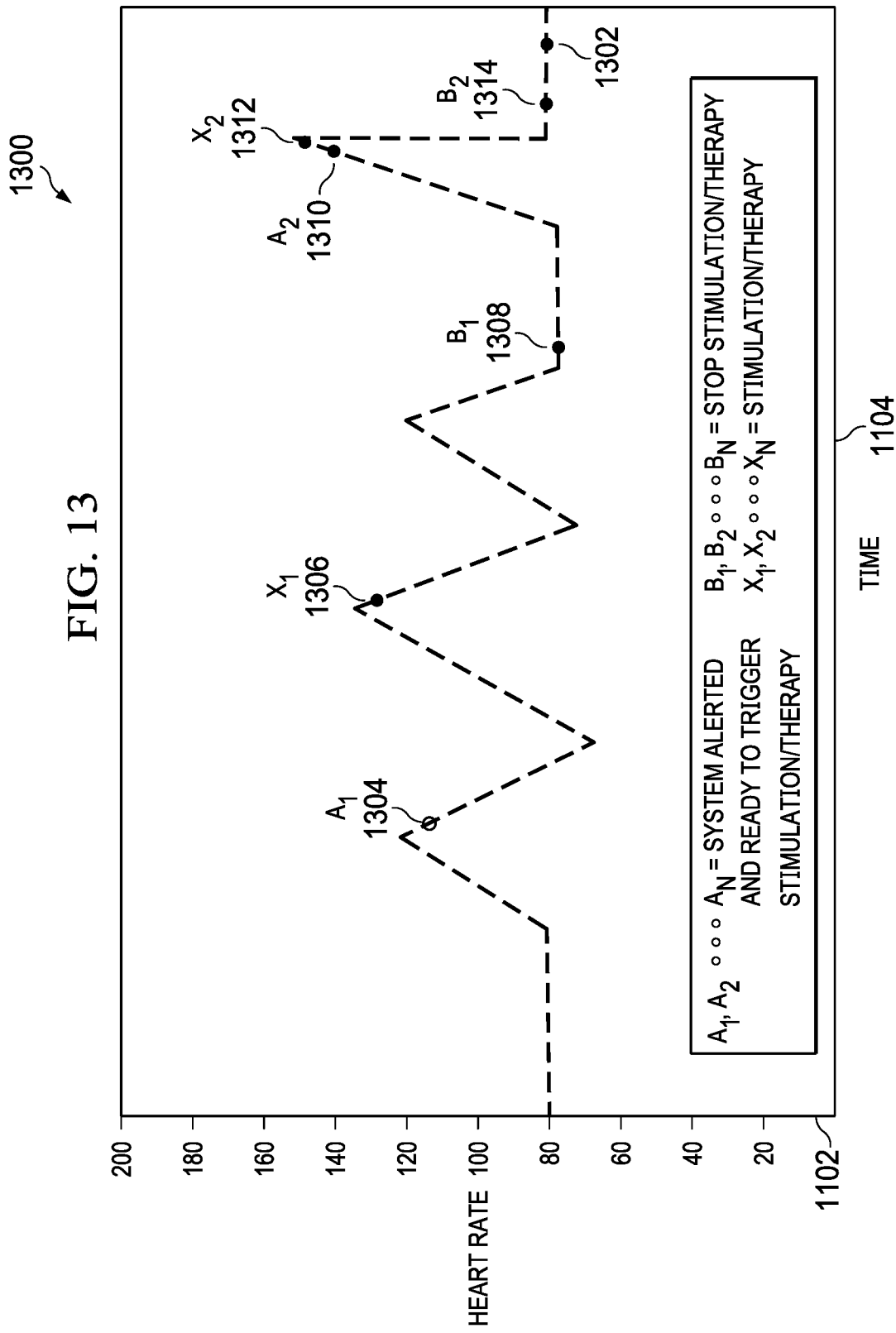
FIG. 13 is another graph of heart rate versus time, according to one embodiment.

In FIG. 13, another graph of heart rate versus time is shown, according to one embodiment. A third graph 1300 illustrating a third heart rate versus time line 1302 for the patient is shown. In this example, the patient's heart rate goes from 80 heart beats per minute to 116 heart beats per minute which creates a first system alert event 1304 (e.g., A1). Further, the system, device, and/or method initiates a first therapy 1306 (e.g., X1) based on the first system alert event 1304. In addition, a first stop stimulation event 1308 (e.g., B1) occurs which turns off all therapies and/or system alerts occurs when the heart rate returns to the approximate starting heart rate and/or a target value. Further, the patient's heart rate goes from 80 heart beats per minute to 123 heart beats per minute which creates a second system alert event 1310 (e.g., A2). Further, the system, device, and/or method initiates a second therapy 1312 (e.g., X2) based on the second system alert event 1310. In addition, a second stop stimulation event 1314 (e.g., B2) occurs which turns off all therapies and/or system alerts occurs when the heart rate returns to the approximate starting heart rate and/or a target value. In these examples shown with FIG. 13, a percentage change in heart rate calculation was completed to determine the one or more system alerts. However, it should be noted that any calculation (e.g., rise over run, etc. can be utilized). Further, all systems alerts and/or therapies may occur as independent events and/or examples. For example, the second system alert may be the first system alert in a specific example. In other words, no other events and/or therapies occurred before the second system alert. Therefore, the second system alert becomes the first system alert. In addition, one or more warnings may be transmitted to the patient, a caregiver, a doctor, a medical professional, and/or logged.

Figure 14:
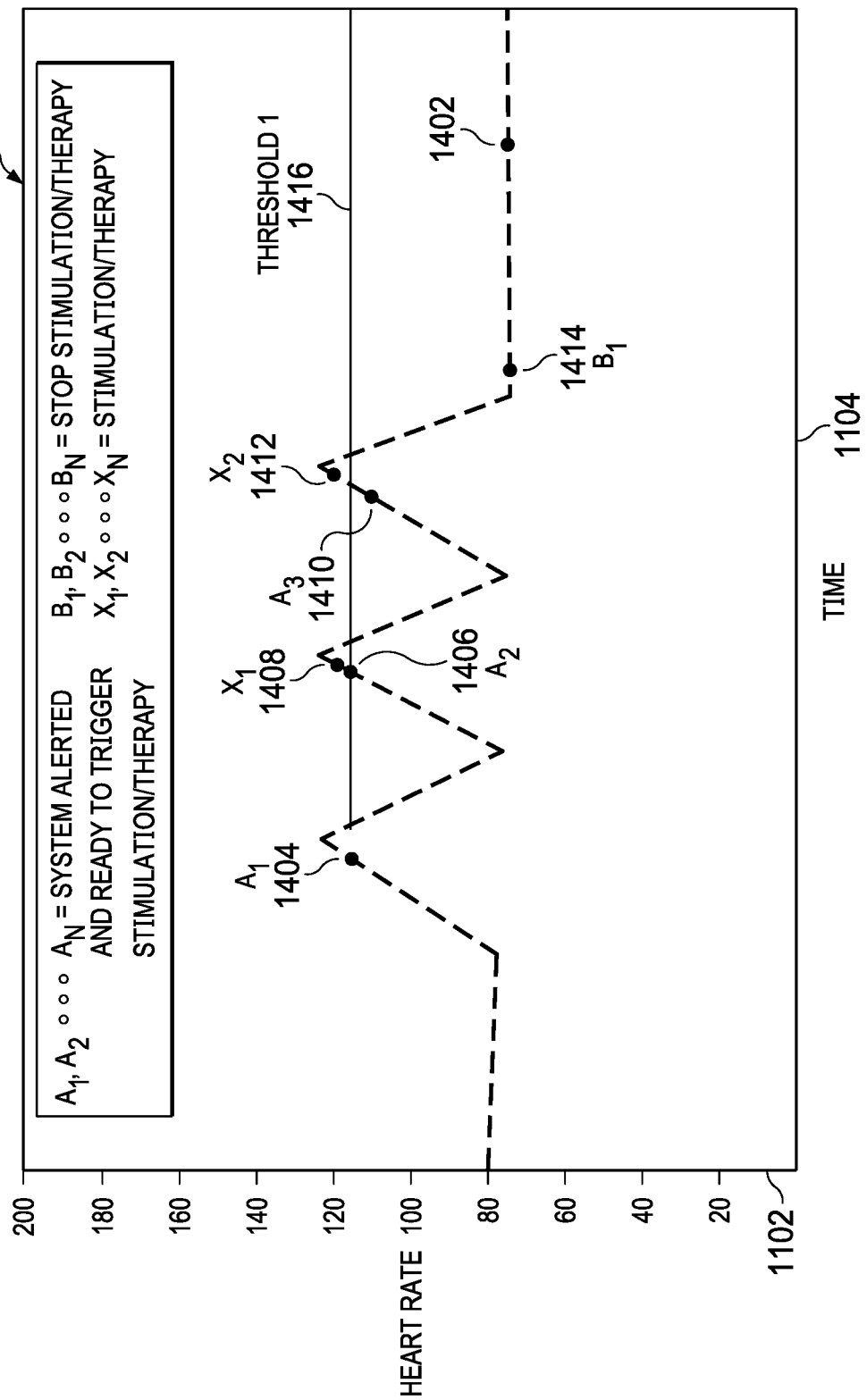
FIG. 14 is another graph of heart rate versus time, according to one embodiment.

In FIG. 14, another graph of heart rate versus time is shown, according to one embodiment. A fourth graph 1400 illustrating a fourth heart rate versus time line 1402 for the patient is shown. In this example, the patient's heart rate goes from 80 heart beats per minute to 120 heart beats per minute which creates a first system alert event 1404 (e.g., A1) because the 120 heart beats per minutes meets or exceeds a first threshold value 1416 (e.g., 115 heart beats per minute). In this example, a second system alert event 1406 (e.g., A2) is created because the heart beats of the patient meets or exceeds the first threshold value 1416 (e.g., 115 heart beats per minute). Further, the system, device, and/or method initiates a first therapy 1408 (e.g., X1) based on the first system alert event 1404 and the second system alert event 1406 occurring. The first system alert event 1404 and the second system alert event 1406 may be time dependent. For example, the first system alert event 1404 and the second system alert event 1406 may have to occur within a first time period for the initiation of the first therapy 1408. In another example, the first system alert event 1404 and the second system alert event 1406 may not be time dependent. Further, a third system alert event 1410 (e.g., A3) is created because the heart beats of the patient meets or exceeds (and/or within a specific rate of the threshold—in this example within 5 percent—heart rate is 110) the first threshold value 1416 (e.g., 115 heart beats per minute). Further, the system, device, and/or method initiates a second therapy 1412 (e.g., X2) based on the first system alert event 1404, the second system alert event 1406, and/or the third system event occurring. It should be noted that the second therapy 1412 has a time delay factor utilized with the second therapy 1412. In another example, no time delay is utilized. In addition, one or more time delays can be used with any therapy, any warning, and/or any alert in this document. The first system alert event 1404, the second system alert event 1406, and the third system alert event 1410 may be time dependent. For example, the first system alert event 1404, the second system alert event 1406, and the third system alert event 1410 may have to occur within a first time period for the initiation of the second therapy 1412. In another example, the first system alert event 1404, the second system alert event 1406, and the third system alert event 1410 may not be time dependent. Further, a first stop stimulation event 1414 (e.g., B1) occurs which turns off all therapies and/or system alerts occurs when the heart rate returns to the approximate starting heart rate and/or a target value. Further, all systems alerts and/or therapies may occur as independent events and/or examples. For example, the third system alert may be the first system alert in a specific example. In other words, no other events and/or therapies occurred before the third system alert. Therefore, the third system alert becomes the first system alert. In addition, one or more warnings may be transmitted to the patient, a caregiver, a doctor, a medical professional, and/or logged.

Figure 15:
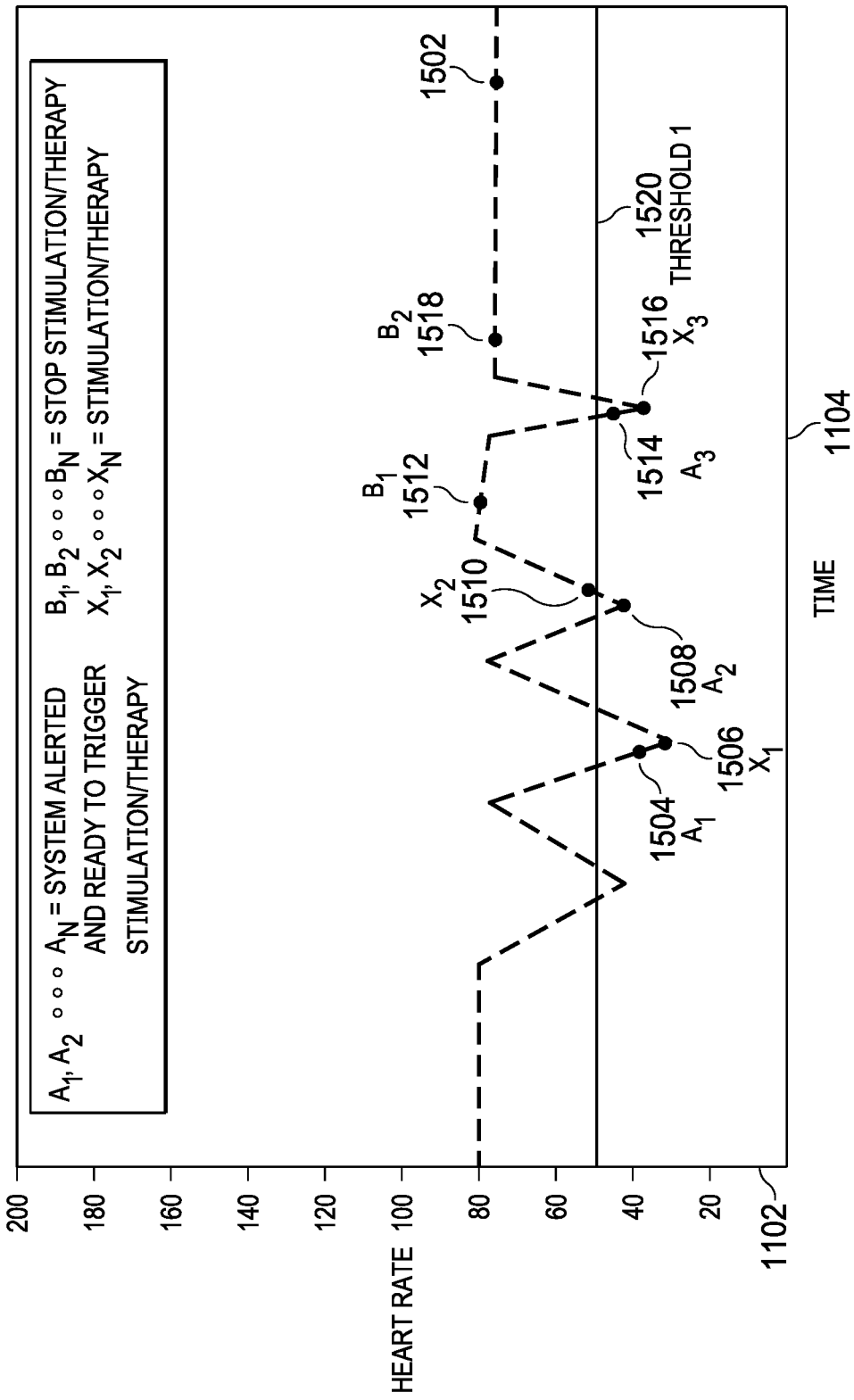
FIG. 15 is another graph of heart rate versus time, according to one embodiment.

In FIG. 15, another graph of heart rate versus time is shown, according to one embodiment. A fifth graph 1500 illustrating a fifth heart rate versus time line 1502 for the patient is shown. In this example, the patient's heart rate goes from 80 heart beats per minute to 40 heart beats per minute which creates a first system alert event 1504 (e.g., A1) because the 40 heart beats per minutes meets or exceeds a first threshold value 1520 (e.g., 50 heart beats per minute). It should be noted that no alert was generated when the heart rate fell to 52 heart beats per minute because 52 heart beats per minute is above the threshold value of 50 heart beats per minute. Further, the system, device, and/or method initiates a first therapy 1506 (e.g., X1) based on the first system alert event 1504 occurring. Further, the patient's heart rate goes from 80 heart beats per minute to 50 heart beats per minute which creates a second system alert event 1508 (e.g., A2) because the 50 heart beats per minutes meets or exceeds the first threshold value 1520 (e.g., 50 heart beats per minute). Further, the system, device, and/or method initiates a second therapy 1510 (e.g., X2) based on the second system alert event 1508 occurring. Further, a first stop stimulation event 1512 (e.g., B1) occurs which turns off all therapies and/or system alerts occurs when the heart rate returns to the approximate starting heart rate and/or a target value. In addition, the patient's heart rate goes from 80 heart beats per minute to 45 heart beats per minute which creates an nth system alert event 1514 (e.g., A3) because the 45 heart beats per minutes meets or exceeds the first threshold value 1520 (e.g., 50 heart beats per minute). Further, the system, device, and/or method initiates an Nth therapy 1516 (e.g., X3) based on the nth system alert event 1514 occurring. Further, an nth stop stimulation event 1518 (e.g., B2) occurs which turns off all therapies and/or system alerts occurs when the heart rate returns to the approximate starting heart rate and/or a target value. Further, all systems alerts and/or therapies may occur as independent events and/or examples. For example, nth system alert event 1514 alert may be the first system alert in a specific example. In other words, no other events and/or therapies occurred before nth system alert event 1514. Therefore, nth system alert event 1514 becomes the first system alert. In addition, one or more warnings may be transmitted to the patient, a caregiver, a doctor, a medical professional, and/or logged.

In regards to FIGS. 11-15 as related to this disclosure, the systems, devices, and/or methods may use a base line heart rate for the patient (e.g., a specific patient Bob, a general patient John Doe with a first health condition, a first age, etc.) over a first time period (e.g. one week, one month, one year, etc.), 50 percentile of all measured heart rates, an average of all heart rates, and/or any other method of determine a baseline heart rate. Further, the threshold level may be determined based on being the 40 percentile of the baseline, 39 percentile of the baseline, 38 percentile of the baseline, . . . , 10 percentile of the baseline, . . . , etc. In addition, the threshold level may be determined based on being the 75 percentile of the baseline, 76 percentile of the baseline, 77 percentile of the baseline, . . . , 90 percentile of the baseline, . . . , 99 percentile of the baseline, . . . , etc. In one example, the threshold value may be the 75 percentile of every recorded heart rate data. In another example, the oscillation does not matter whether the heart rate change is in an increasing direction or a decreasing direction. In various examples, the systems, devices, and/or method may reduce an amplitude of change (e.g., damping the change in heart rate) to enhance system performance and/or to reduce side effects. In addition, the determination of one or more side effects may initiate a reduction in therapy, a stoppage of therapy, a modification of therapy (e.g., changing a therapy that reduces heart rate to another therapy that increases heart rate), one or more warnings, and/or one or more logging of data.

Figure 16:
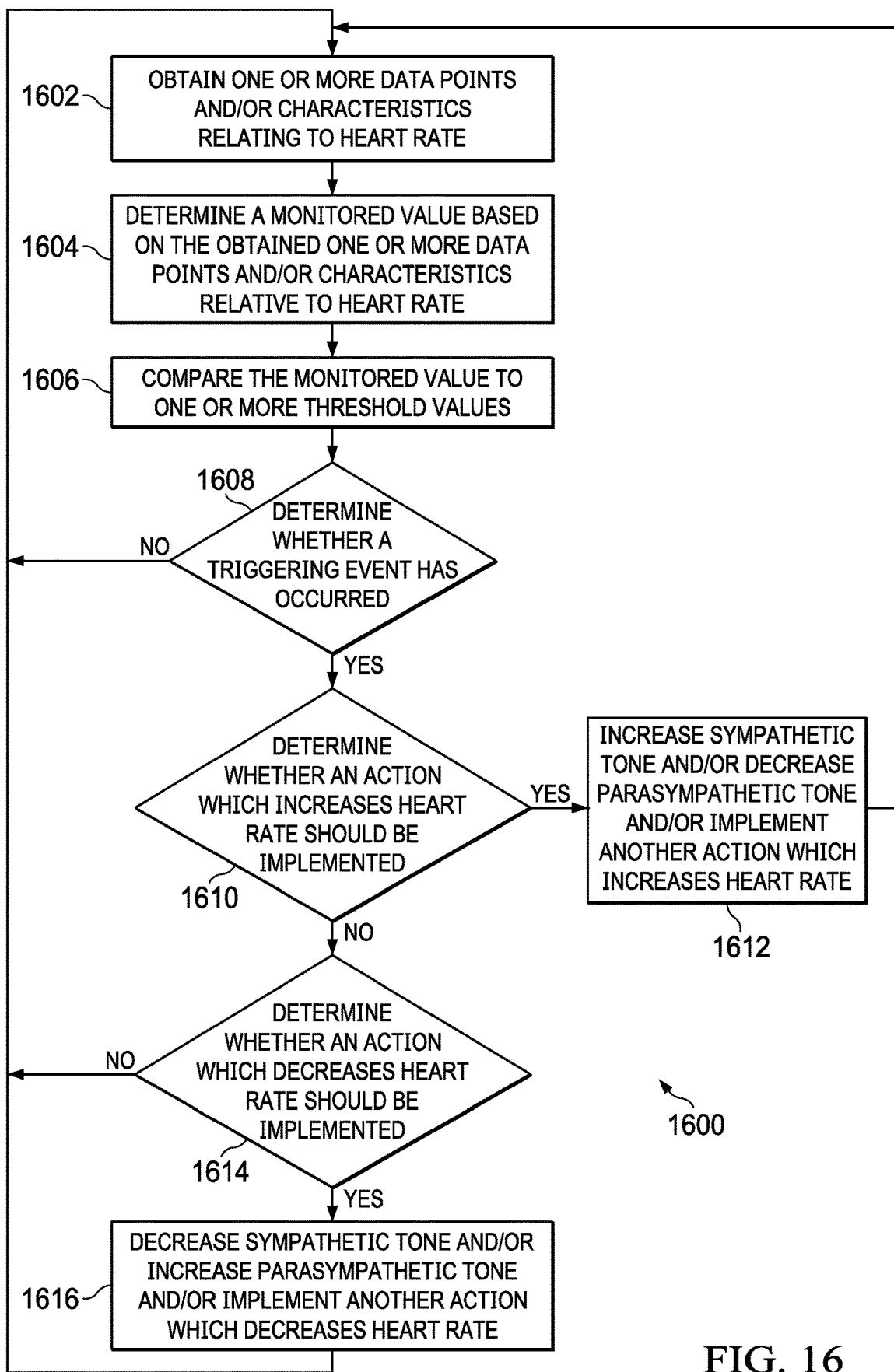
FIG. 16 is a flowchart of a therapy procedure, according to one embodiment.

In FIG. 16, a flowchart of a therapy procedure is shown, according to one embodiment. A method 1600 includes obtaining one or more data points and/or characteristics relating to heart rate of a patient (step 1602). The method 1600 may also include determining a monitored value based one the obtained one or more data points and/or characteristics relating to the heart rate (step 1604). The method 1600 may further compare the monitored value to one or more threshold values (step 1606). The method 1600 may via one or more processors (of a medical device(s) and/or medical device system) determine whether a triggering event has occurred (step 1608). If no triggering event has occurred, then the method 1600 moves back to step 1602. If a triggering event has occurred, then the method 1600 may determine via one or more processors (of a medical device(s) and/or medical device system) whether an action which increases heart rate should be implemented (step 1610). If an action which increases heart rate should be implemented, then the method 1600 may increase a sympathetic tone via one or more actions and/or decrease a parasympathetic tone via one or more actions and/or implement another action which increases heart rate (step 1612). After the implements of one or more actions, the method 1600 returns to step 1602. If an action which increases heart rate should not be implemented, then the method 1600 may determine via one or more processors (of a medical device(s) and/or medical device system) whether an action which decreases heart rate should be implemented (step 1614). If an action which decreases heart rate should be implemented, then the method 1600 may decrease a sympathetic tone via one or more actions and/or increase a parasympathetic tone via one or more actions and/or implement another action which decreases heart rate (step 1616). After the implements of one or more actions, the method 1600 returns to step 1602.

In one embodiment, a system for treating a medical condition in a patient includes: a sensor for sensing at least one body data stream; a heart rate unit capable of determining a heart rate of the patient based on the at least one body data stream; and a logic unit configured via one or more processors to compare a monitored value which is determined based on one or more data points relating to the heart rate to one or more threshold values, the logic unit further configured to determine a triggering event based on the comparison. Further, the one or more processors may initiate one or more actions to change the heart rate of the patient based on the determination of the triggering event.

In another example, the system includes at least one electrode coupled to a vagus nerve of the patient and a programmable electrical signal generator. In another example, the one or more processors may increase a sympathetic tone to increase the heart rate of the patient. In another example, the one or more processors may decrease a parasympathetic tone to increase the heart rate of the patient. In another example, the one or more processors may decrease a sympathetic tone to decrease the heart rate of the patient. In another example, the one or more processors may increase a parasympathetic tone to decrease the heart rate of the patient. In another example, the system includes a seizure detection unit which analyzes the at least one body data stream to determine an epileptic seizure status. In another example, the system includes at least one electrode coupled to a vagus nerve of the patient and a programmable electrical signal generator. Further, the one or more processors may apply an electrical signal to the vagus nerve of the patient based on a determination that a seizure is characterized by a decrease in the heart rate of the patient where the electrical signal is applied to block action potential conduction on the vagus nerve.

In another embodiment, a system for treating a medical condition in a patient, includes: a sensor for sensing at least one body data stream; at least one electrode coupled to a vagus nerve of the patient; a programmable electrical signal generator; a heart rate unit capable of determining a heart rate of the patient based on the at least one body data stream; and a logic unit configured via one or more processors to compare a monitored value which is determined based on one or more data points relating to the heart rate to one or more threshold values, the logic unit further configured to determine a triggering event based on the comparison. Further, the one or more processors may initiate one or more actions to change the heart rate of the patient based on the determination of the triggering event.

In another example, the one or more processors may increase a sympathetic tone to increase the heart rate of the patient based on a first triggering event. Further, the one or more processors may decrease a sympathetic tone to decrease the heart rate of the patient based on a second triggering event. Further, the one or more processors may decrease a parasympathetic tone to increase the heart rate of the patient based on a third triggering event. Further, the one or more processors may increase a parasympathetic tone to decrease the heart rate of the patient based on a fourth triggering event.

In another example, the one or more processors may increase the sympathetic tone to increase the heart rate of the patient based on a second triggering event. Further, the one or more processors may increase the sympathetic tone to increase the heart rate of the patient based on a third triggering event. Further, the one or more processors increase the sympathetic tone to increase the heart rate of the patient based on an nth triggering event.

In another example, the one or more processors decrease a sympathetic tone to decrease the heart rate of the patient based on a first triggering event. Further, the one or more processors decrease the sympathetic tone to decrease the heart rate of the patient based on a second triggering event. Further, the one or more processors may decrease the sympathetic tone to decrease the heart rate of the patient based on a third triggering event. In addition, the one or more processors decrease the sympathetic tone to decrease the heart rate of the patient based on an nth triggering event.

Cardio-protection in epilepsy is a rapidly growing field of vital importance. In this disclosure, systems, devices, and/or method of protecting the heart from standstill or fatal arhythmias are disclosed. Further in this disclosure, systems, devices, and/or methods of automated detections, warnings, reportings, treatments, controls and/or any combination thereof of ictal and peri-ictal chronotropic instability are shown.

Figure 17:
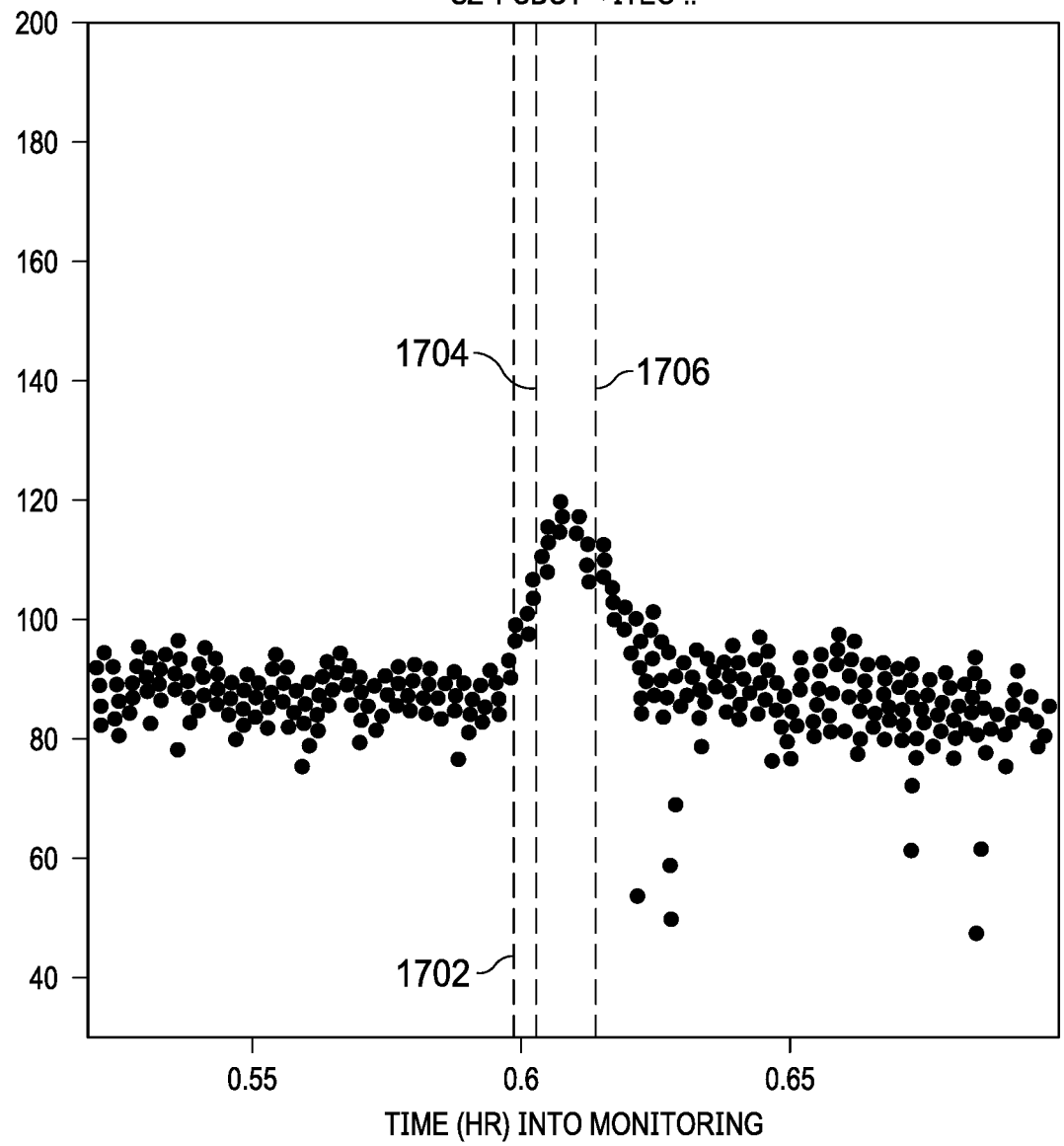
FIG. 17 is a graph relating to the automated detection and control of ictal and peri-ictal chronotropic instability, according to one embodiment.
Figure 18:
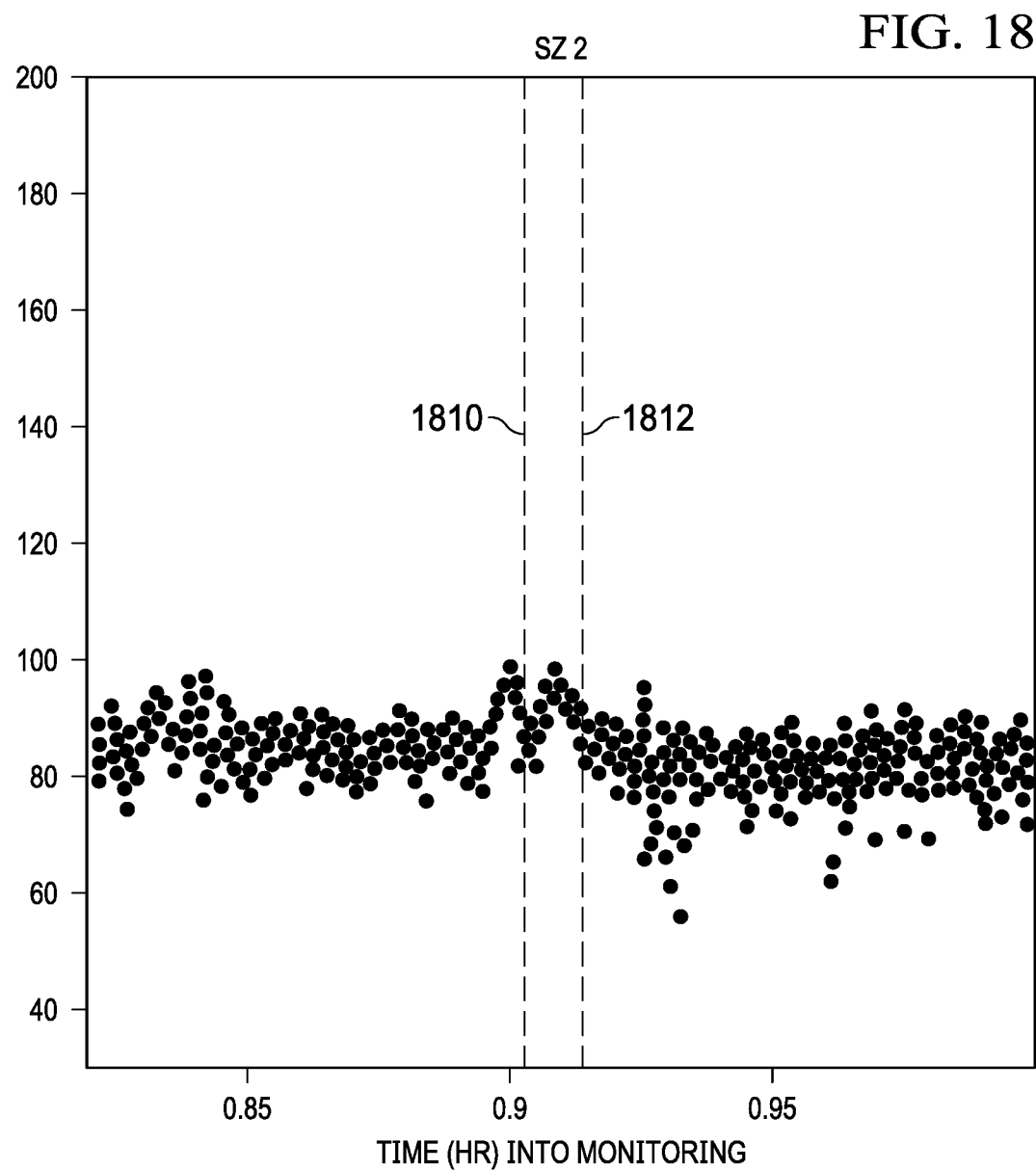
FIG. 18 is a graph relating to the automated detection and control of ictal and peri-ictal chronotropic instability, according to one embodiment.

In FIG. 17, a graph shows monotonic increase and decrease in heart rate. In FIG. 17, a first triggering event, a first warning event, and/or a first therapy event 1702 are shown. Further, a second triggering event 1704, a second warning event, and/or a second therapy event 1704 are shown. In addition, an Nth triggering event, an Nth warning event, and/or an Nth therapy event 1706 are shown. In FIG. 18, the heart rate of the patient increases which is followed by a decrease in heart rate, then an increase heart rate and a final decrease in heart rate. In this example, the first drop in heart rate crossed downwardly the detection threshold which would have temporarily disabled the warning system and the delivery of the therapy. While the first peak was not temporally correlated with paroxysmal activity on any of the intra-cranial electrodes used in this patient, it is likely that the first increase in heart rate was caused by epileptic discharges from a brain site that was not being investigated. In this example, the x-axis is time in hours and the y-axis is heart beats per minute. In this example, an electrographic onset in the brain 1810 is shown and an electrographic termination in the brain 1812 is shown.

Figure 19:
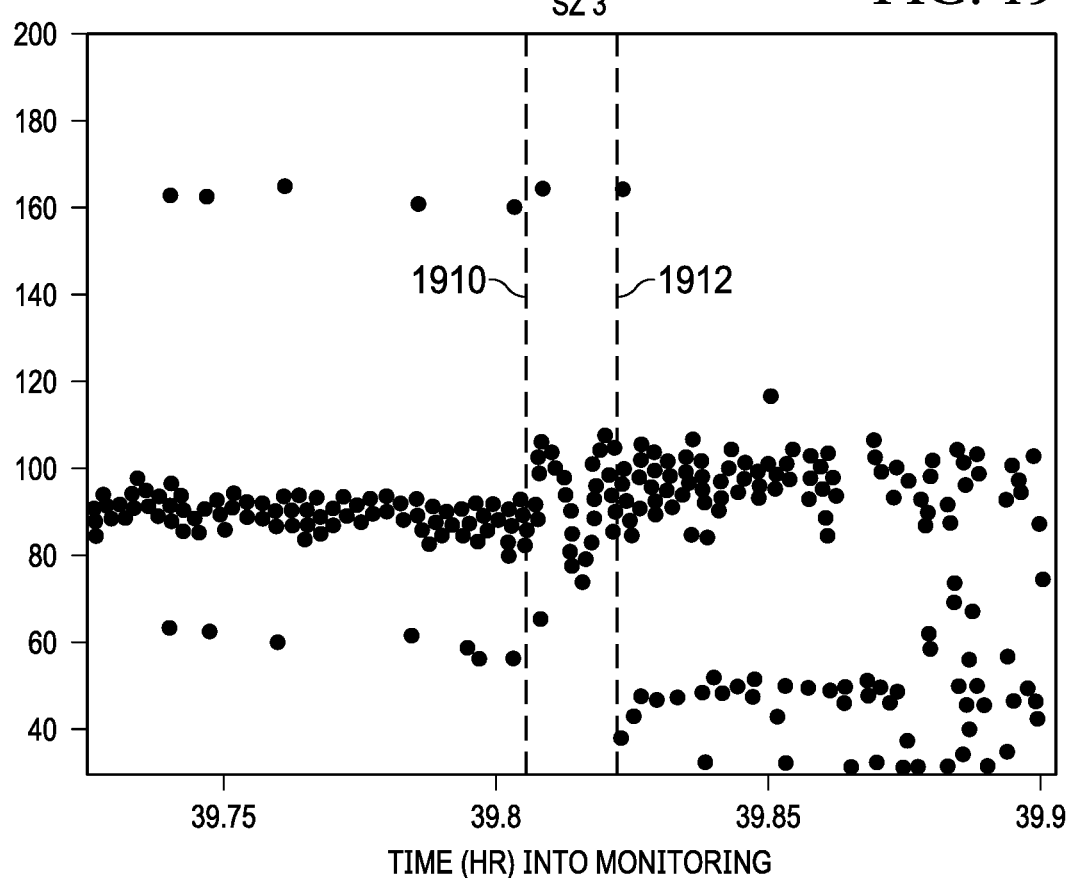
FIG. 19 is a graph relating to the automated detection and control of ictal and peri-ictal chronotropic instability, according to one embodiment.

In FIG. 19, a change in ictal heart rate is shown. In this example, the drop in heart rate during the seizure, is even more prominent that the one depicted in FIGS. 17-18, as it is below the inter-ictal baseline. It should be noted that the oscillations in heart rate during the post-ictal period are indicative of cardiac instability. In this example, a seizure onset point 1910 and a seizure termination point 1912 are shown.

In FIG. 20, large amplitude tachycardia cycles occurring quasi-periodically after termination of paroxysmal activity recorded with intra-cranial electrodes. While the mechanisms responsible for these oscillations are unknown, the probability that they are epileptic in nature cannot be excluded, since electrographic and imaging data used to guide intra-cranial electrode placement pointed to the existence of only one epileptogenic site.

In FIG. 21, small amplitude continuous quasi-periodic oscillations preceding and following a seizure recorded with intra-cranial electrodes (same patient as FIG. 20). In various embodiments, ictal and peri-ictal cardiac instability are shown. The mechanisms leading to SUDEP have not been elucidated, in part due to the inability to record data during the critical events that culminate in cardiac fibrillation or in standstill (or in respiratory arrest). In this example, a first triggering event, a first warning event, and/or a first therapy event 2102 are shown. Further, an Nth triggering event, an Nth warning event, and/or an Nth therapy event 2104 are shown.

The data obtained in intractable epileptics undergoing epilepsy surgery evaluation not only supports a cardiac mechanism (of course, not at the exclusion of catastrophic respiratory failure) but more specifically points to chronotropic instability as backdrop against which, lethal arrhythmias or cardiac standstill may ensue. Moreover, the instability is not restricted to the ictal period but, in certain cases, precedes and/or follows it for several minutes. FIGS. 17-21 illustrate the spectrum of instability in intractable epileptics. This phenomenon is referred herein to as Ictal and Pre-Ictal Chronotropic Instability.

The challenges that for accurate quantification and delivery of efficacious therapies, ictal chronotropic instability poses, were addressed and strategies to manage them are outlined. Here, the attention is focused on Ictal and Pre-Ictal Chronotropic Instability, a more prolonged and serious pathological phenomenon in intractable epileptics and on the vital issues of cardio-protection.

The aim of this disclosure is to contingently and adaptively dampen based on the slope, amplitude, duration and "direction" (positive or negative chronotropic and its magnitude relative to an adaptive baseline/reference heart rate) the heart oscillations present before, during or after epileptic seizures.

While several embodiments may be envisioned, on embodiment (for efficacy, practicality and cost-effectiveness) is to electrically stimulate/activate the trunk or a branch of the right vagus nerve in the case of elevations in heart (to reduce the heart rate, when there are more than 2 consecutive oscillations/cycles or 1 that is large and prolonged. The intensity and duration of stimulation as well as other parameters are determined by the slope, amplitude and duration of the oscillations, while ensuring adequate blood perfusion to all organs. In the case of negative chronotropic effects (decreases in heart rate) the trunk or a branch of the right vagus nerve may be "blocked" using certain electrical stimulation techniques or through cooling; the effect of this intervention is to increase heart rate.

In one embodiment, the "height" of the oscillation is the only feature considered. While obviously important, this embodiment does not take into consideration a possibly more important feature: the rate at which the oscillation occurs: the consequences of waiting to intervene until an oscillation reaches a certain height (e.g., 120 bpm) are different if it takes, 30 seconds for the heart rate to reach the value than if it takes 2 seconds to reach the value. Estimating the rate of change of the heart rate, provides life-saving information. Another aspect is the inter-maxima or inter-minima interval between oscillations. Having heart rate oscillation occur every 2-3 seconds is much more serious than every 1-2 hours. In one example, one benefit may be that the window to act is lengthen which can save lives. In one embodiment, a system for treating a medical condition in a patient includes: a sensor for sensing at least one body data stream; a heart rate unit which determines a heart rate and a heart rate oscillation of the patient based on the at least one body data stream; and a logic unit which compares via one or more processors a monitored value which is determined based on one or more data points relating to the heart rate and to the heart rate oscillation to a threshold value, the logic unit determines a triggering event based on the comparison where the one or more processors initiate one or more actions to change the heart rate of the patient based on the determination of the triggering event.

In another example, the system includes at least one electrode coupled to a vagus nerve of the patient and a programmable electrical signal generator. Further, the one or more processors may increase a sympathetic tone to increase the heart rate of the patient. In another example, the one or more processors may decrease a parasympathetic tone to increase the heart rate of the patient. In another example, the one or more processors may decrease a sympathetic tone to decrease the heart rate of the patient. Further, the one or more processors may increase a parasympathetic tone to decrease the heart rate of the patient. In addition, the system may include a seizure detection unit which analyzes the at least one body data stream to determine an epileptic seizure status. The system may include at least one electrode coupled to a vagus nerve of the patient and a programmable electrical signal generator where the one or more processors apply an electrical signal to the vagus nerve of the patient based on a determination that a seizure is characterized by a decrease in the heart rate of the patient and where the electrical signal is applied to block action potential conduction on the vagus nerve. In addition, the heart unit may determine an inter-maxima interval and an inter-minima interval between a first oscillation and a second oscillation. Further, the logic unit may compare the inter-maxima interval and the inter-minima interval to an interval threshold. In addition, the one or more processors may initiate one or more actions based on the interval threshold being reached.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below. In addition, all examples, embodiments, and/or elements may be combined in any manner that are disclosed in this document. In other words, an element from a first example (FIG. 1A) can be combined with any other element, such as, a second element from an Nth example (FIG. 10). For brevity, all these examples are not written out but are part of this document.

In another example, this disclosure relates generally to medical device systems and, more particularly, to medical device systems capable of testing the responsiveness of a patient having brain state changes. Testing of responsiveness of a patient may be used to determine a time at which loss of function for the patient occurs. Therapies using electrical currents or fields to provide a therapy to a patient (electrotherapy) are beneficial for certain neurological disorders, such as epilepsy. Implantable medical devices have been effectively used to deliver therapeutic electrical stimulation to various portions of the human body (e.g., the vagus nerve) for treating various medical conditions, including epilepsy. As used herein, "stimulation," "neurostimulation," "stimulation signal," or "neurostimulation signal" refers to the application of an electrical, mechanical, magnetic, electromagnetic, photonic, acoustic, physiological, cognitive, and/or chemical signal to a neural structure in the patient's body. The signal is an exogenous signal that is distinct from the endogenous electro-chemical activity inherent to the patient's body and the environment. In other words, the stimulation signal (whether electrical, mechanical, magnetic, electro-magnetic, photonic, acoustic or chemical in nature) applied to a cranial nerve or to other nervous tissue structure in the present disclosure is a signal applied from a medical device, e.g., a neurostimulator.

A "therapeutic signal" refers to a stimulation signal delivered to a patient's body with the intent of treating a medical condition through a suppressing (blocking) or modulating effect to neural tissue. The effect of a stimulation signal on neuronal activity may be inhibitory (suppressing) or excitatory (expressing); additionally, the effect may be immediate ("all or none") or the result of spatio-temporal summation of stimuli (modulation or biasing), a process that lacks the immediacy associated with "all or none" responses. However, for simplicity, the terms "stimulation" and "modulation," and variants thereof, are used interchangeably herein. In general, however, the delivery of an exogenous signal itself refers to "stimulation" of the neural structure, while the effects of that signal, if any, on the electrical activity of the neural structure are properly referred to as "modulation," which may manifest as either inhibition (suppression) or excitation (expression). Furthermore, depending upon myriad factors such as the history (recent and distant) of the nervous system, stimulation parameters and time of day, to name a few, the effects of stimulation (with the same parameters) upon the neural tissue may be excitatory or inhibitory, facilitatory or disfacilitatory and may suppress, enhance or leave unaltered, the neuronal activity it intends to control. In spite of these vagaries, there is evidence of a suppressing effect of a stimulation signal on abnormal neural tissue activity, specifically of epileptic seizures (see Osorio et al., Ann Neurol 2005; Osorio & Frei IJNS 2009) Suppression of abnormal neural activity is a threshold or suprathreshold process and the temporal scale over which it occurs is usually in the order of a few milliseconds to hundreds of milliseconds. Modulation of abnormal or undesirable neural activity, unlike suppression is a "sub-threshold" process in the spatio-temporal domain that may summate and result under certain conditions, in threshold or suprathreshold neural events. The temporal scale of modulation is much longer than that associated with "all or none" responses. Wave annihilation or reduction through collision with identical, similar or dissimilar waves, or by "pushing" them (the waves) into their "null space" or "black hole" (Winfree; Osorio & Frei 2009) are techniques that rely on stimulation but for which concepts of inhibition or excitation as conventionally used in electrophysiology may not apply. These forms of annihilation (via collision and phase resetting) fall within the purview of wave mechanics and topology. Those skilled in the art realize that there are multiple approaches (and mechanisms) for controlling undesirable oscillations via stimulation (see Osorio et al, Ann Neurol 2005; Kalitzin et al.; Sunderam et al)

In some embodiments, electrotherapy may be provided by implanting an electrical device, i.e., an implantable medical device (IMD), inside a patient's body stimulation of a nervous tissue, such as a cranial nerve. Generally, electrotherapy signals that perform neuromodulation are delivered by the IMD via one or more leads or wirelessly. When applicable, the leads generally terminate at their distal ends in one or more electrodes, and the electrodes, in turn, are coupled to tissue in the patient's body. For example, a number of electrodes may be attached to various points of a nerve or other tissue inside a human body for delivery of a neurostimulation signal.

While contingent (also referred to as "closed-loop," "active," or "feedback" stimulation (i.e., electrotherapy applied in response to sensed information, such as heart rate) stimulation schemes have been proposed, conventional vagus nerve stimulation (VNS) is non-contingent, programmed periodic stimulation. Specifically, conventional vagus nerve stimulation usually involves a series of grouped electrical pulses defined by an "on-time" (such as 30 sec) and an "off-time" (such as 5 min). This type of stimulation is also referred to as "open-loop," "passive," or "non-feedback" stimulation. Each sequence of pulses during an on-time may be referred to as a "pulse burst." The burst is followed by the off-time period in which no signals are applied to the nerve. During the on-time, electrical pulses of a defined electrical current (e.g., 0.5-3.5 milliamps) and pulse width (e.g., 0.25-1.0 milliseconds) are delivered at a defined frequency (e.g., 20-30 Hz) for a certain duration (e.g., 10-60 seconds). The on-time and off-time parameters together define a duty cycle, which is the ratio of the on-time to the combination of the on-time and off-time, and which describes the percentage of time that the electrical signal is applied to the nerve.

In conventional VNS, the on-time and off-time may be programmed to define an intermittent pattern in which a repeating series of electrical pulse bursts are generated and applied to a cranial nerve such as the vagus nerve. The off-time is provided to minimize adverse effects and conserve power. If the off-time is set at zero, the electrical signal in conventional VNS may provide continuous stimulation to the vagus nerve. Alternatively, the off time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in conventional VNS may be programmed over a range of values. The pulse width for the pulses in a pulse burst of conventional VNS may be set to a value not greater than about 1 msec, such as about 250-500 usec, and the number of pulses in a pulse burst is typically set by programming a frequency in a range of about 20-150 Hz (i.e., 20 pulses per second to 150 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Of the approximately 60 million people worldwide affected with epilepsy, roughly 23 million people suffer from epilepsy resistant to multiple medications (Kwan et al. 2000). In the USA alone, the annual cost of epilepsy care is USD 12 billion (in 1995 dollars), most of which is attributable to subjects with pharmaco-resistant seizures (Begley et al. 2000). Pharmaco-resistant seizures are associated with an increase in mortality and morbidity (compared to the general population and to epileptics whose seizures are controlled by medications) and with markedly degraded quality of life for patients. Seizures may impair motor control, responsiveness to a wide class of stimuli, and other cognitive functions. The sudden onset of a patient's impairment of motor control, responsiveness, and other cognitive functions precludes the performance of necessary and even simple daily life tasks such as driving a vehicle, cooking, or operating machinery, as well as more complex tasks such as acquiring knowledge and socializing.

The deleterious impacts of epilepsy on patients' health and well-being are compounded by the inability to gather, among others, accurate information about event frequency and severity. Event diaries (generated by the patient and/or caregivers) are utterly inadequate (Blum, 1996; Elger 2007) in that event counts/frequencies are grossly underestimated and severity is not measurable due to: a) lack of useful, representative metrics and b) the inability of even experts in the field (epileptologists) to precisely and objectively quantify them based on visual observation. Automated means for quantification of event frequency and severity would allow the stratification of patients by severity, estimation of risks injury and death, formulation of prognosis, tracking the progression of the disorder, and objective assessment of therapeutic efficacy, without which advances are in this field are unlikely to occur or are meager. However, to our knowledge, no practical automated means for quantification of event frequency and severity using signals different from brain electrical signals are publicly available as of this writing, let alone any suitable for rigorous and valid assessment of therapeutic efficacy.

In one aspect of the present disclosure, a method for determining responsiveness of a patient having brain state changes is provided. The method comprises receiving an indication of the occurrence of a triggering event; administering to the patient, in response to the indication, a test of responsiveness; and determining, based upon a result of the test, at least one responsiveness parameter selected from the group consisting of (i) a time of occurrence of a change in the patient's responsiveness, (ii) a duration of a change in the patient's responsiveness; (iii) a magnitude of a change in the patient's responsiveness, (iv) a time interval from the indication of event occurrence to a change in the patient's responsiveness, (v) a type of change in the patient's responsiveness, (vi) an estimation of a seizure severity; (vii) a classification of a seizure into clinical or subclinical; (viii) a classification of a clinical seizure into simple partial, complex partial, or generalized; (ix) an assessment of efficacy of a therapy for the patient's medical condition; (x) an assessment of the state of the disease and formulation of a prognosis for the patient; (xi) an estimation of a risk of injury or death for the patient; and (xii) two or more thereof.

In another aspect of the present disclosure, a computer readable program storage unit encoded with instructions that, when executed by a computer, perform the method discussed above.

In another aspect of the present disclosure, a medical device system for determining a responsiveness of a patient having brain state changes, comprising a receiving unit adapted to receive an indication of a triggering event; a responsiveness testing unit adapted to administer a test of responsiveness to a patient in response to the indication; a determination unit adapted to receive a result of the test of responsiveness from the responsiveness testing unit and to make at least one determination selected from the group consisting of (i) a time of occurrence of a change in the patient's responsiveness, (ii) a duration of a change in the patient's responsiveness; (iii) a magnitude of a change in the patient's responsiveness, (iv) a time interval from the indication of event occurrence to a change in the patient's responsiveness, (v) a type of change in the patient's responsiveness, (vi) an estimation of a seizure severity; (vii) a classification of a seizure into clinical or subclinical; (viii) a classification of a clinical seizure into simple partial, complex partial, or generalized; (ix) an assessment of efficacy of a therapy for the patient's medical condition; (x) an assessment of the state of the disease and formulation of a prognosis for the patient; (xi) an estimation of a risk of injury or death for the patient; and (xii) two or more thereof.

The impairment of motor function or of responsiveness that characterizes certain types of events, are associated with high risk for serious injuries, even death, and of inappropriate behavior that further isolates the patient socially. However, since in certain types of events these impairments lag behind the onset of abnormal electrical brain activity, a "natural" window exists during which intervention would minimize these risks. Automated warning of impending impairment of motor function or of responsiveness would minimize risk of injury and social embarrassment, particularly in the case of certain complex partial and secondarily generalized events, as well as allow patients to safely perform certain activities precluded by this disorder.

Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, traumatic brain injury, coma, migraine headache, obesity, eating disorders, sleep disorders, cardiovascular disorders (such as congestive heart failure and atrial fibrillation), hypertension, endocrine disorders (such as diabetes and hypoglycemia), and pain (including neuropathic pain and fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; 5,330,515; 6,961,618; 7,457,665; and 7,630,757; among others. Despite the numerous disorders for which cranial nerve stimulation has been proposed or suggested as a treatment option, the mechanisms of action of stimulation for many (if not all) cranial nerves remain relatively poorly understood.

There is a wide range of medical disorders for which VNS may be prescribed. Among these, those manifesting with events characterized by sudden loss of consciousness (and inevitably of postural tone) or of responsiveness/awareness (without loss of consciousness and of postural tone) are particularly hazardous and disabling to those who suffer from them. Loss of consciousness results invariably in falls to the ground which may be associated with serious bodily and brain injuries; loss of responsiveness (during which patients remain awake but lack discernment) are often the cause of serious vehicular and household accidents (such as fires, burns). Sudden loss of consciousness may be cardiovascular/autonomic or neurological in nature; loss of awareness is almost always neurological in nature. Among the neurological causes of loss of consciousness (with or without abnormal motor activity) epileptic seizures rank second to cardiovascular/autonomic dysfunction; for loss of responsiveness, epileptic seizures rank highest. Epileptic seizures are characterized by sudden, transient increases (above the normal level) in neuronal membrane voltages, commonly associated with changes in autonomic function. Seizures may affect all bodily functions under autonomic control, most notably cardio-respiratory and also temperature (Sunderam & Osorio), pupillary, skin resistance control, sphincter tone, peristalsis, etc. By identifying which bodily functions are affected by an epileptic sicure, changes in the signals or indices associated with the affected function(s) may be used to detect seizures automatically. Specifically seizures may be detected via: a) brain electrical signals recorded from the scalp (electroencephalogram; EEG) or directly from the brain (electrocorticogram; ECoG); b) autonomic signals or indices such as changes in heart and respiratory activity rate, pupillary size. For example, increases in heart rates (tachycardia) and respiratory rates (tachypnea or hyperventilation) often occur in patients with partial seizures while they are motionless. The occurrence of autonomic changes during seizures is consistent with the fact that autonomic functions are under the control of the brain (central nervous system) (Brodal) which is the site of epileptogenesis and ictiogenesis. Autonomic or neurologic index or indices is/are used herein to refer to any detectable state or change of state reflective of the function of one or more aspects of the autonomic nervous system of the patient.

Figure 22A:
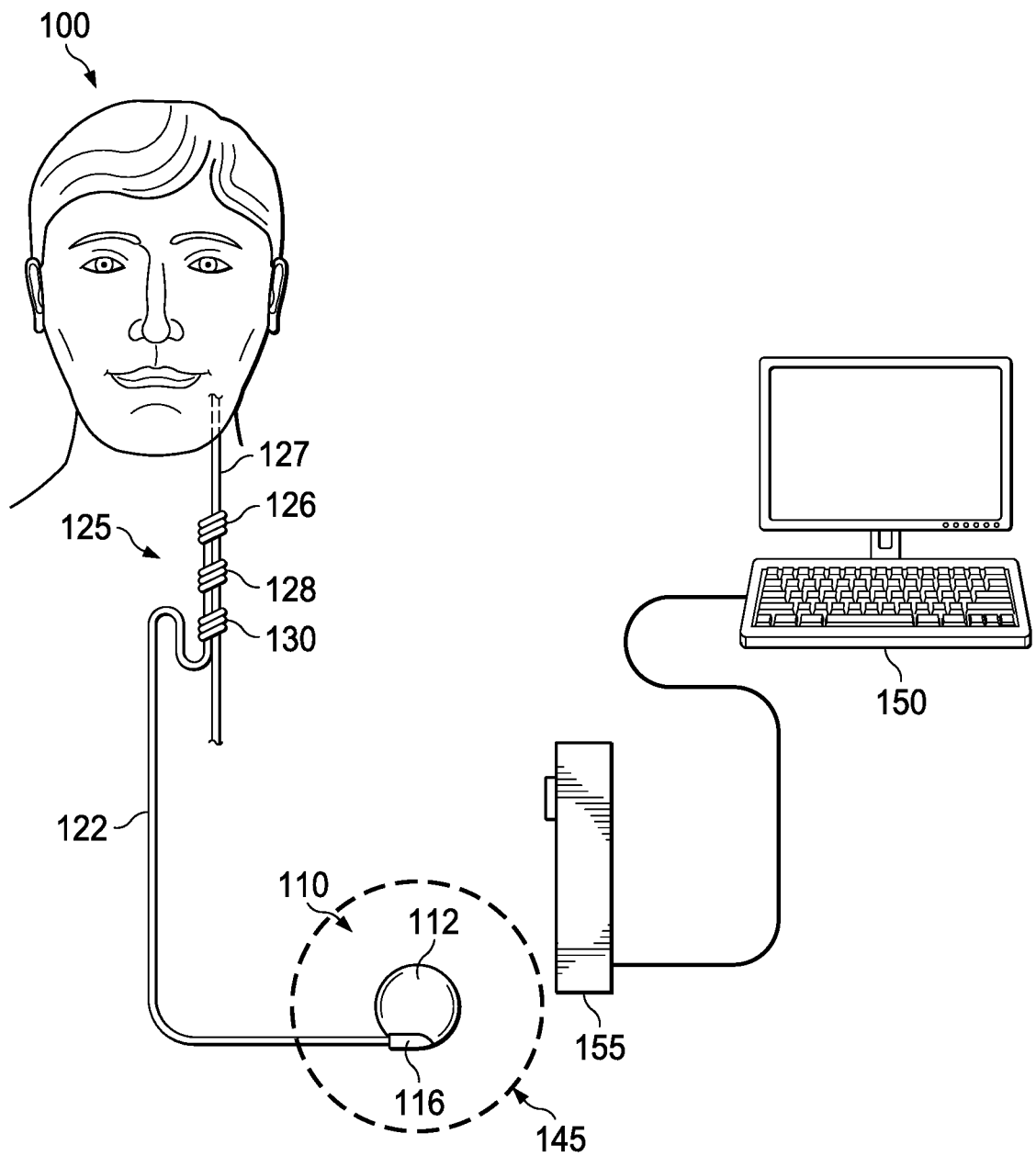
FIG. 22A provides a stylized diagram of an implantable medical device implanted into a patient's body for providing a therapeutic electrical signal to a neural structure of the patient's body, in accordance with one illustrative embodiment of the present disclosure.

Although not so limited, a system capable of implementing embodiments of the present disclosure is described below. FIG. 22A depicts the implantable medical system (IMD) 100 for implementing one or more embodiments of the present disclosure. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a cardiac pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Texas, USA as the Model 302 electrode assembly. However, persons of skill in the art will appreciate that many electrode designs could be used in the present disclosure. In one embodiment, the two electrodes are wrapped about the vagus nerve, and the electrode assembly 125 may be secured to the vagus nerve 127 by a spiral anchoring tether 130 such as that disclosed in U.S. Pat. No. 4,979,511 issued Dec. 25, 1990 to Reese S. Terry, Jr. and assigned to the same assignee as the instant application. Lead assembly 122 may be secured, while retaining the ability to flex with movement of the chest and neck, by a suture connection to nearby tissue (not shown).

In some embodiments, the electrode assembly 125 may comprise temperature sensing elements and/or heart beat sensor elements for detection of electrical, mechanical or acoustic activity. Other sensors for other autonomic indices may also be employed. Both closed-loop and open-loop stimulation may be combined or delivered by a single IMD according to the present disclosure. Either or both modes may be appropriate to treat a specific patient under observation.

The electrical pulse generator 110 may be programmed with an external device (ED) such as computer 150 using programming software known in the art. A programming wand 155 may be coupled to the computer 150 as part of the ED to facilitate wireless radio frequency (RF) communication between the computer 150 and the implanted pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

Figure 22B:
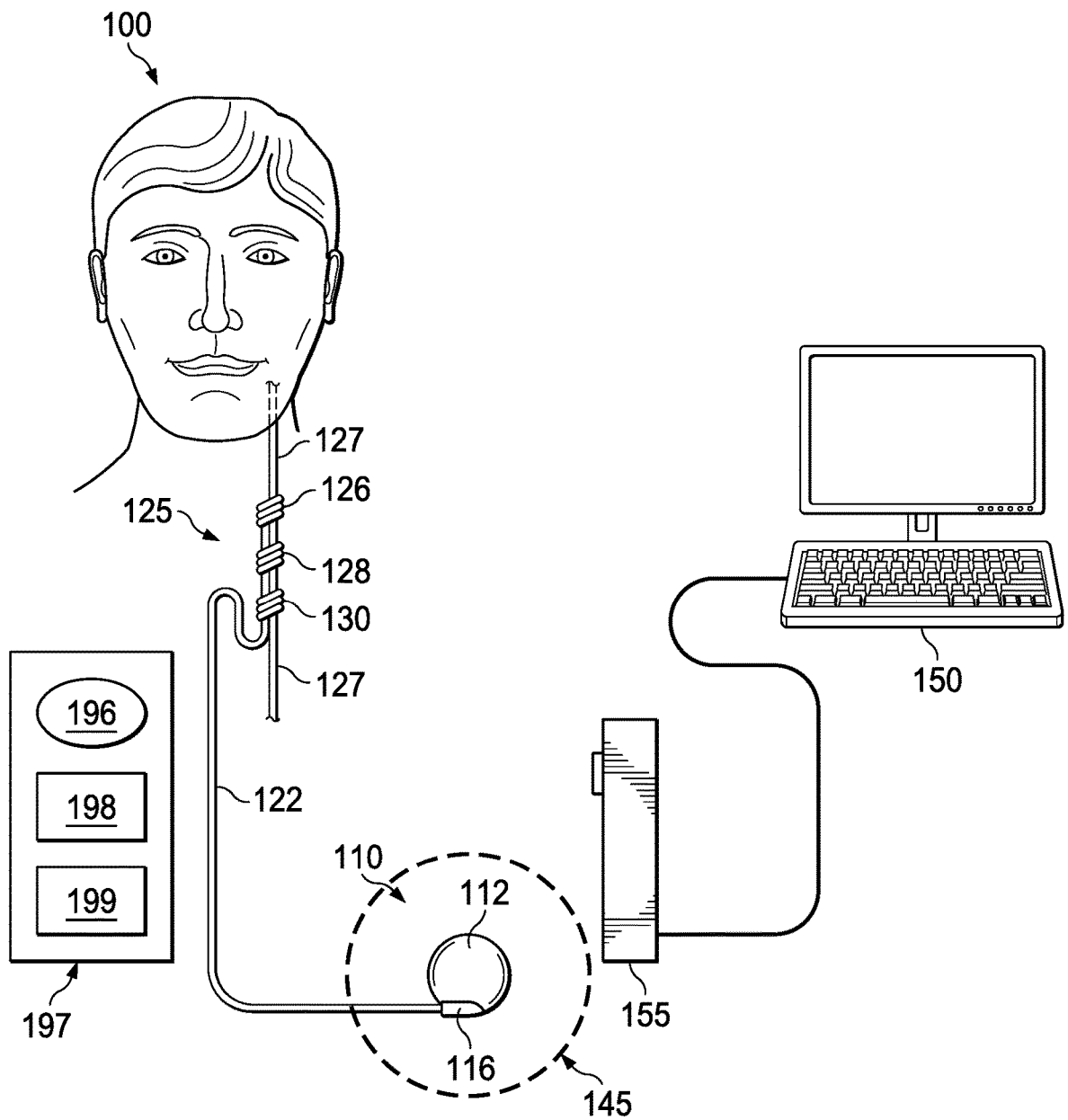
FIG. 22B provides a stylized diagram of a medical device system comprising an implantable medical device implanted into a patient's body for providing a therapeutic electrical signal to a neural structure of the patient's body, and an external device for administering a responsiveness test to a patient, in accordance with another illustrative embodiment of the present disclosure.

Turning now to FIG. 22B, the depicted embodiment shows, in addition to the IMD 100, a responsiveness testing input/output (I/O) unit 197 for implementing one or more embodiments of the present disclosure. The responsiveness testing I/O unit 197 contains an input device 199, an output device 198, and a control and communication unit 196.

The output device 198 is configured to present an output to the patient when it receives instructions and/or commands to do so from the control and communication unit 196. By "output" is meant a visual, auditory, tactile, olfactory or gustatory stimulus or signal perceptible by one or more of the senses of a patient. Exemplary output devices 198 include, but are not limited to, visual devices, such as LCD, LED, or other displays, which may output a light, graphics, text, animation, or video, among others, or two or more thereof; audio devices, such as speakers, which may output sound, synthesized speech, recorded speech, or live speech, among others, or two or more thereof; and tactile devices, which may output Braille text, vibration, heat, or cold, among others, or two or more thereof. The output device 198 may also comprise two or more of the devices described above, among others; for example, the output device 198 may comprise a visual device and an audio device, for example, an LCD screen and a speaker, among others. In various embodiments, the output device 198 may be housed in the medical device 2300 or an external unit 2370.

The input device 199 is configured to receive an input from the patient when it receives instructions to do so from the control and communication unit 196. By "input" is meant any state or change in state of the device effected by one or more actions of the patient. Exemplary input devices 199 include, but are not limited to, touchscreens, buttons, switches, microphones, and cameras, among others, or two or more thereof. In various embodiments, the input device 199 may be housed in the medical device 2300 or an external unit 2370.

The control and communication unit 196, as mentioned, provides instructions to the output device 198 to present an output and to the input device 199 to receive an input. It also provides instructions for the functions of a triggering event indication receiving unit (2365, FIG. 23B), a responsiveness testing unit (2385, FIG. 23B), a responsiveness determination unit (2387, FIG. 23B), and a responsiveness parameter unit (2388, FIG. 23B), which functions each involve the receipt of, transmission of, and internal handling of, data, as will be discussed in more detail with reference to FIG. 23B, below.

The responsiveness testing I/O unit 197 is shown as a single discrete unit in FIG. 1B, but other embodiments are possible. The responsiveness testing I/O unit 197 may be external to the patient's body, and in a further embodiment, may be configured to be held in the hand. As should be apparent, in other embodiments, the responsiveness testing I/O unit 197 may not be configured to be held in the hand, but may instead be placed elsewhere on the patient's body (e.g., on the wrist, among other locations), on a table, desk, nightstand, floor, or on, in, or otherwise sited with reference to a feature of the patient's environment. The hardware, the software, or both of the responsiveness testing I/O unit 197 may be especially designed for responsiveness testing, but need not be; for example, in one embodiment, the responsiveness testing I/O unit 197 is embodied as software in a cellular telephone, a smartphone (e.g., an Apple iPhone® or a smartphone sold by BlackBerry, Palm, Motorola, HTC, or the like), a personal digital assistant (PDA), or another programmable handheld electronic device (e.g., an Apple iPod®). In another embodiment, the responsiveness testing I/O unit 197 is embodied as software on a netbook, notebook, or desktop computer, such as one running an operating system such as Microsoft Windows, Apple Macintosh OS X, or Linux, among others. In some embodiments, the patient may be provided with a plurality of responsiveness testing I/O units 197, networked together in a system capable of receiving inputs and providing outputs to any of the units 197 comprising the network. For certain applications the responsiveness testing I/O unit 197 may be implanted into the patient's body.

Also, in various embodiments, portions of the responsiveness testing I/O unit 197 may be housed in separate units. For example, the output device 198 may be a monitor or a speaker of a computer, and the input device 199 may be a touchscreen, button, switch, microphone, or camera embodied in a handheld device. For another example, the output device 198 may be a monitor or a speaker of a handheld device, and the input device 199 may be a keyboard, mouse, microphone, or camera of a computer. For still another example, the output device 198 may be a monitor or a speaker of a handheld device, and the input device 199 may be a magnetic swipe sensor or a tap sensor of the IMD 100.

Also, although FIG. 22B shows the responsiveness testing I/O unit 197 in proximity to the IMD 100, as should be apparent, the responsiveness testing I/O unit 197 may be used entirely separately from the IMD 100. For example, a patient having brain state changes may use the responsiveness testing I/O unit 197 without having the IMD 100 implanted within his or her body. In such embodiments, the disclosure may lack any implanted component. Thus, IMD 100 may be absent and the disclosure may comprise responsiveness testing I/O unit 197 alone or with an external medical device.

Figure 23A:
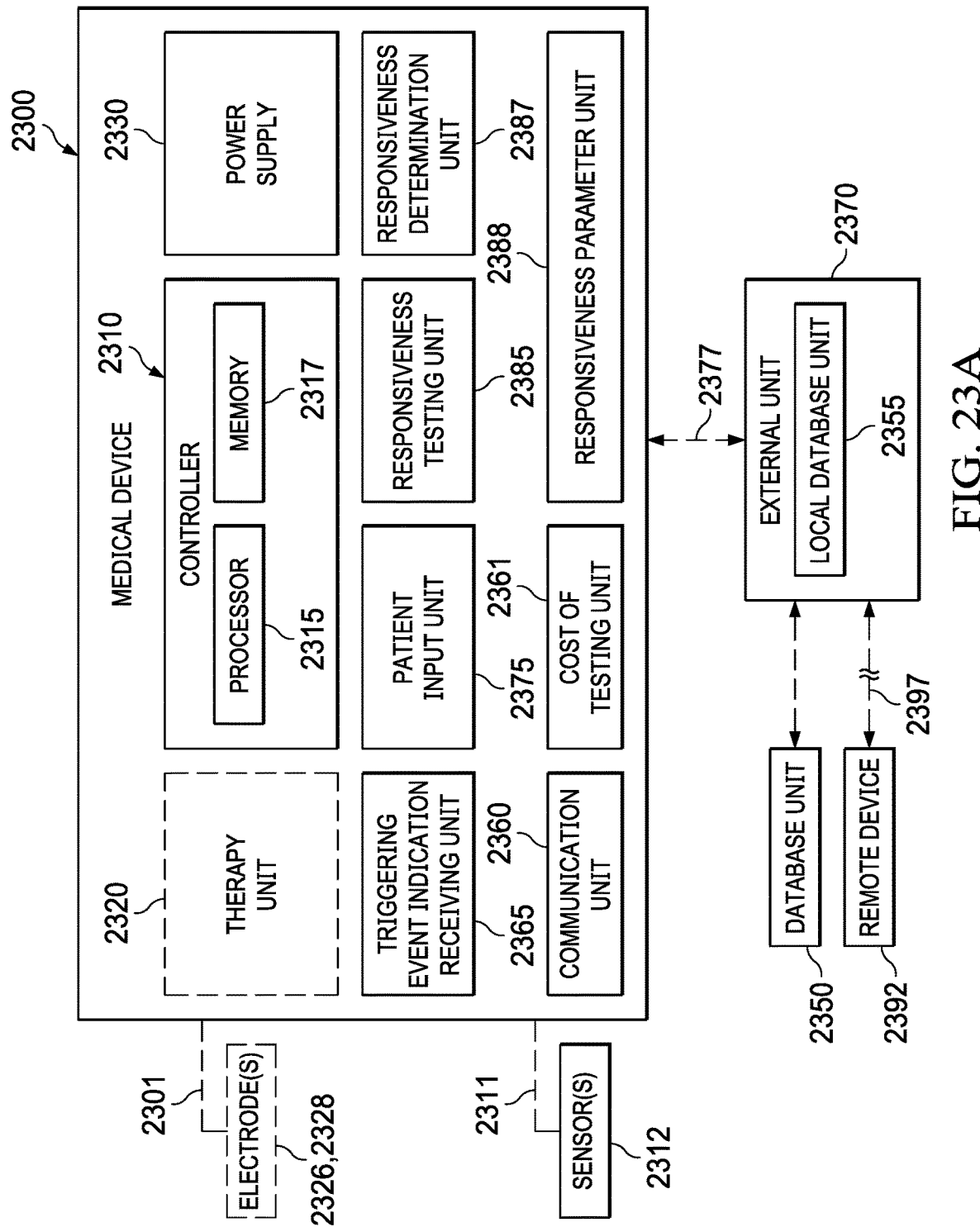
FIG. 23A is a block diagram of a medical device system that includes a medical device, in accordance with one illustrative embodiment of the present disclosure.

Turning now to FIG. 23A, a block diagram depiction of the medical device (MD) 2300 is provided, in accordance with one illustrative embodiment of the present disclosure. The MD 2300 (such as implantable generator 110 from FIG. 22A) may comprise a controller 2310 capable of controlling various aspects of the operation of the MD 2300. In some embodiments, the controller 2310 is capable of receiving data and causing a therapy unit 2320 to generate and deliver a therapy, such as an electrical signal to target tissues of the patient's body for treating a medical condition using, for example, electrodes 2326, 2328. Therapy unit 2320 is optional, as indicated by the dotted line. In some embodiments, therapy unit 2320 is absent. For example, the controller 2310 may receive instructions from another device, or may cause the electrical signal to be generated and delivered based on calculations and programming internal to MD 2300. The controller 2310 is capable of affecting substantially all functions of the MD 2300. The MD 2300 may be an external device, or in an alternative embodiment, an implantable medical device.

The controller 2310 may comprise various components, such as a processor 2315, a memory 2317, etc. The processor 2315 may comprise one or more microcontrollers, microprocessors, etc., capable of performing various executions of software components. The memory 2317 may comprise various memory portions where a number of types of data (e.g., internal data, external data instructions, software codes, status data, diagnostic data, etc.) may be stored. The memory 2317 may comprise one or more of random access memory (RAM), dynamic random access memory (DRAM), electrically erasable programmable read-only memory (EEPROM), flash memory, volatile memory, non-volatile memory, etc.

In one embodiment, MD 2300 may be an implantable medical device, and coupling 2301 may comprise a lead assembly such as lead assembly 122 (FIG. 22A). In another embodiment, MD 2300 may be external to the patient's body, and may be coupled to an implanted lead via a wireless or inductive coupling, such as an RF inductive coupling. In a still further embodiment, MD 2300 may be external to the patient's body and electrodes 2326, 2328 may also be external to the patient's body. Whether MD 2300 is an implantable or external unit, a therapeutic electrical signal may be delivered to the electrodes 2326, 2328 by the therapy unit 2320 based upon instructions from the controller 2310. The therapy unit 2320 may comprise various circuitry, such as electrical signal generators, impedance control circuitry to control the impedance "seen" by the leads, and other circuitry that receives instructions relating to the delivery of the electrical signal to tissue. Therapy unit 2320 may be configured to deliver biphasic, charge balanced pulses, multiphasic pulses, or monophasic pulses. Therapy unit 2320 may deliver constant current or constant voltage. Further, therapy unit 2320 may be configured to deliver magnetic currents, or to operate as a drug administration and/or thermal control unit.

In other embodiments, coupling 2301 is operatively coupled to an electrode, wherein the electrode is adapted to be coupled to at least one of a portion of a brain structure of the patient, a cranial nerve of a patient, an organ for special senses of a patient, the spinal cord of a patient, a spinal cord root of a patient, a sympathetic nerve structure of the patient, a peripheral nerve of the patient, the skin of the patient, or a muscle of the patient.

In some embodiments, therapy unit 2320 as well as coupling 2301 and electrodes 2326, 2328 may be omitted. In other words, the responsiveness testing described herein can be performed by MD 2300 whether or not a therapy for the patient's medical is provided.

The MD 2300 may also comprise a power supply 2330. The power supply 2330 may comprise a battery, voltage regulators, capacitors, etc., to provide power for the operation of the MD 2300, including delivering the therapeutic electrical signal. The power supply 2330 comprises a power source that in some embodiments may be rechargeable. In other embodiments, a non-rechargeable power source may be used. The power supply 2330 provides power for the operation of the MD 2300, including electronic operations and the electrical signal generation and delivery functions. The power supply 2330 may comprise a lithium/thionyl chloride cell or a lithium/carbon monofluoride (LiCFx) cell for implantable embodiments, and more common watch batteries or 9 volt batteries for non-implantable embodiments. Other battery types known in the art of implantable medical devices may also be used. Where MD 2300 is external to the patient's body, for example, power supply 2380 may comprise a photo-voltaic or solar cell.

The MD 2300 may also comprise a communication unit 2360 capable of facilitating communications between the MD 2300 and various devices. In particular, the communication unit 2360 is capable of providing transmission and reception of electronic signals to and from an external unit 2370, such as computer 150 and a wand 155 that can communicate with the MD 2300 remotely (FIG. 22A). The communication unit 2360 may include hardware, software, firmware, or any combination thereof.

It should be noted that any of the connections 2301, 2311, 2377, 2397, or that between external unit 2370 and database unit 2350 may be wired or wireless, as a matter of routine skill for the person of ordinary skill in the art having the benefit of the present disclosure.

Also, the MD 2300 may comprise a cost of testing unit 2361 capable of determining at least some of the costs associated with responsiveness testing of the patient. For example, the cost of testing unit 2361 may calculate power consumption by the various units associated with testing that are described herein, consumption of computational resources by the various units associated with testing, or the like. This information may be useful to the clinician in order to allow him or her to adjust the number, difficulty, or other parameters of the responsiveness tests administered to the patient.

The MD 2300 may also comprise one or more sensor(s) 2312 coupled via sensor coupling 2311 (which may comprise a lead or an inductive coupling) to the MD 2300. The sensor(s) 2312 are capable of receiving signals related to a body parameter, such as an autonomic or neurologic index, and delivering the signals to the MD 2300. In a particular embodiment, the sensor(s) 2312 deliver the signals to the controller 2310, where they may be processed by the processor 2315 and/or stored in the memory 2317, and/or routed to the triggering event indication receiving unit 2365, as discussed below.

Exemplary sensor(s) 2312 include electrocardiogramaevices, accelerometers, inclinometers, pupillometers, face or body temperature monitors, skin resistance monitors, and/or sound and pressure sensors, among others.

In one embodiment, the sensor(s) 2312 may be the same as stimulating electrode(s) 2326, 2328. In other embodiments, the sensor(s) 2312 are separate structures that may be placed in, on, or near a particular organ, tissue, nerve, or blood vessel of the patient, or outside the patient's body, such as on the patient's skin or in the patient's environment.

In one embodiment, the MD 2300 may comprise a triggering event indication receiving unit 2365 that is capable of receiving signals related to a triggering event. The triggering event indication receiving unit 2365 may be capable of performing any necessary or suitable amplifying, filtering, and performing analog-to-digital (A/D) conversions on the received signals to determine whether a triggering event has occurred. The triggering event indication receiving unit 2365, in one embodiment, may comprise software module(s) that are capable of performing various interface functions, filtering functions, etc., to determine whether a triggering event has occurred. In another embodiment the triggering event indication receiving unit 2365 may comprise hardware circuitry that is capable of performing these functions. In yet another embodiment, the triggering event indication receiving unit 2365 may comprise hardware, firmware, software and/or any combination thereof.

The triggering event indication receiving unit 2365 may determine whether a triggering event occurred, wherein the triggering event is selected from the group consisting of a) an indication from a medical event detection algorithm that a medical event is occurring or is imminent; b) a manual signal to administer the responsiveness test to the patient; or c) a command to administer a responsiveness test to the patient in the absence of an indication from a medical event detection algorithm that a medical event is occurring or imminent.

The triggering event for testing responsiveness may include one or more of a) an indication from a medical event detection algorithm, based upon one or more body parameters of the patient, that a medical event relevant to the patient's condition is occurring or is imminent (e.g., detection of a future, imminent, or on-going epileptic seizure or other medical event using heart or other autonomic indices or brain activity of the patient, which may also be described as a positive or affirmative output of a medical event detection algorithm (POMEDA)), b) a manual signal from a patient, caregiver or physician to administer the responsiveness test to the patient, or c) a command to administer a responsiveness test to the patient in the absence of an indication from a medical event detection algorithm that a medical event is occurring or imminent (e.g., a command to administer a responsiveness test to the patient during a negative output of a medical event detection algorithm (NOMEDA)). The command provided in the absence of a medical event detection event may be based upon circadian or ultradian rhythms of the patient, past medical event history of the patient (e.g. times of day, week, or month when medical event probability exceeded a specified value), expiration of a random or pseudorandom timer or similar events. Elapse of a periodic, random, or pseudorandom time period may be used to present a responsiveness test to the patient in response to a NOMEDA so as to: a) establish a representative baseline (e.g., non-seizure) performance for comparison (statistical) with that associated with medical events, including a post-medical events period during which performance or responsiveness may remain impaired for some time; b) avoid anxiety or conditioning of the patient to expect a medical events whenever a test is administered, and c) to minimize biasing test responses.

The end of a time period may be determined either by comparing the current absolute time with a time previously determined to indicate the end of the time period, or by incrementing a counter of time units until a value previously determined to indicate the end of the time period is reached. For example, the time period may be programmed to have a predefined or random duration with a specified range, e.g., from 15 minutes to 24 hours, or may be programmed as a specific number of random timepoints within a 24 hour period or weekly period. Tests in response to a NOMEDA can be administered while the patient is awake to establish a representative baseline performance, since response times and other measures of cognitive performance vary as a function of circadian rhythms. For statistical purposes, it may also be desirable to administer tests at about the same time of day on consecutive days; and/or at about the same time of a day as a medical event that occurred on a previous day; among other possibilities. To ensure statistical validity, in one embodiment the logic associated with administering the test in response to what is believed to be a NOMEDA may verify that the output of any medical event detection algorithm is, in fact, negative (i.e., that no medical event is occurring or imminent, as contrasted with the simple expiration of a timer) before the test is applied and logged as having occurred in response to a NOMEDA.

The previously determined time (for testing purposes) may be set at any point prior to the end of the time period, and may be programmed or reprogrammed by the manufacturer or the practitioner. For example, the ratio of "non-algorithm-triggered" (i.e., manual or NOMEDA) to "algorithm-triggered" (i.e., POMEDA) events can be programmed, e.g., about equal POMEDA and NOMEDA testing, 50% more (or less) NOMEDA testing than POMEDA, or increased testing (both POMEDA and NOMEDA triggered) as a function of when (e.g., time of day, time of week, etc.) the patient historically has an increased probability of medically relevant events.

For POMEDA-triggered testing, a change in an autonomic or neurologic index may be determined by receiving a value related to an autonomic or neurologic index and comparing it with a previously determined value. The autonomic or neurologic index value may be determined by analyzing at least one set of signals received from the patient and selected from the group consisting of cardiovascular signals, breathing signals, pupillary signals, skin signals, blood pressure, among others. Additionally or alternatively, neurological signals, such as those generated by the brain or cranial nerves or body kinetic signals (e.g., signals generated by motion of the patient's body as determined by an accelerometer or inclinometer) may be used for detecting medically relevant events, such as epileptic seizures.

For example, the autonomic or neurologic index value(s) used to determine whether a medical event has occurred may be the heart rate, a change in the heart rate, or the rate of change in heart rate, and the triggering event may be a heart rate above a first previously determined value, a heart rate below a second previously determined value, or a rate of change of heart rate above a third previously determined value, a heart rate variability above or below a fourth or fifth previously determined value, among others. Other cardiovascular indices values include, but are not limited to, blood pressure, heart sounds, heart rhythm, heartbeat wave morphology, heartbeat complex morphology, or the shape of the deflection of the thoracic wall as the heart apex beats against it, among others. Such cardiovascular index values can be detected by electrocardiogramaod pressure monitors, a microphone, or apexcardiography, among others.

For another example, the autonomic or neurologic index value(s) used to determine whether a medical event has occurred may be related to the respiration (breath) rate, and the triggering event may be a respiration rate above a first previously determined value, a respiration rate below a second previously determined value, or a rate of change of respiration rate above a third previously determined value, among others. Other respiratory index values include, but are not limited to, respiration pattern, airflow velocity, respiration amplitude (tidal volume), oxygen saturation, arterial gas concentrations, and blood pH, among others. Such respiratory index values can be detected by techniques and apparatus known to the person of ordinary skill in the art.

For still another example, the autonomic or neurologic index value(s) used to determine whether a medical event has occurred may be related to one or more skin signals, such as a change in the skin resistivity of the patient.

For another example, the autonomic or neurologic index value(s) used to determine whether a medical event has occurred may be related to one or more temperature signals, such as a change in the skin temperature of a part of the patient's face (e.g., face) (see Sunderam & Osorio) or a change in the core temperature of the patient.

For still another example, brain signals, such as those determinable by an EEG or ECoG may be used to determine whether a medical event has occurred, and the triggering criterion may be a value of one or more of the brain signals above a first previously determined value or below a second previously determined value.

For another example, the detection criterion may be related to one or more body kinetic signals. The body kinetic signal may be determinable by electromyography, an accelerometer, and/or an inclinometer, and the triggering criterion may be a value of the body kinetic signal indicative of the body's (or of a portion thereof such as an arm or a leg) acceleration, direction, position, amplitude or force of movements.

For yet another example, the index value(s) used to determine whether a medical event has occurred may be related to one or more cranial nerve signals.

For yet another example, the index value(s) used to determine whether a medical event has occurred may be related to one or more autonomic nerve or ganglia signals.

For still a further example, a plurality of autonomic and/or neurologic (e.g., brain, cranial nerve, or kinetic) index value(s) may be used to determine whether a medical event has occurred. For example, the triggering event may be a finding that the patient's heart rate is above a threshold value at a time when a body kinetic signal shows the patient's body orientation is reclined or when it indicates the patient stopped moving.

For POMEDA-triggered testing, the algorithm used may be one that determines a probability of a medical event and yields a positive output if the probability of the medical event exceeds a threshold. For example, one or more autonomic or neurologic indices may be assigned a weight, such as in the range 0 to 1, based on its history of sensitivity and/or specificity regarding the patient's medical condition; the time of day, time of week, time or month, time of year, the patient's wake/sleep status, the patient's physical activity level, the patient's current or recent food intake; or the like. The index value(s) may be analyzed to produce an output value, e.g., a probability, p. If the probability exceeds a threshold, a positive output may be yielded by the algorithm.

Whether a seizure occurred may be determined by analyzing a change in an autonomic or neurologic index value, temporal or other patterns, or morphologies, such as those discussed above; by receiving an input from a medical event detection algorithm; or by receiving an input from a clinician or knowledgeable layperson who observes an electroencephalographic or clinical onset of a seizure. Such analysis is known, for example, from work by the present inventors, such as U.S. Pat. Nos. 7,457,665; 6,961,618; and 6,549,804, hereby incorporated by reference herein.

The triggering event indication receiving unit 2365 is capable of receiving an indication of a triggering event and communicating such receipt to the controller 2310. Based upon the indication received by the triggering event indication receiving unit 2365, a responsiveness testing unit 2385 may administer a test of responsiveness to the patient.

"Responsiveness" is used herein to refer to any response made by a patient upon exposure to a stimulus.

"Motor function" is used herein to refer to a function actuated by the contraction of at least one muscle of the patient.

In one embodiment, responsiveness is part of a cognitive function. "Cognitive function" is used herein to refer to an action that indicates to an observing adult of at least average intelligence and mental health that the patient is purposefully implementing a behavior in pursuit of an objective. Examples of cognitive functions include, but are not limited to, attention, short-term memory, long-term memory, language fluency, visuospatial awareness, abstract reasoning, or two or more thereof.

In another embodiment, the test of responsiveness can test the patient's reflex function.

In a system as complex as the human body, the person of ordinary skill in the art would understand that for a cognitive function to be observed and/or measured, the cognitive function implements a motor function.

In certain embodiments, a positive test of motor function may reveal purposive behavior was performed by the patient to yield that positive test, i.e., a positive test of motor function in these embodiments may be further taken as a positive test of cognitive function. The converse is not necessarily true. In other words, a negative test of cognitive function may be coincident with various motor functions, such as non-purposive movement of limbs, non-purposive vocalization, etc. For example, a patient with cognitive impairment may experience certain reflex motions or "automatisms" that are not to be confused as positive evidence of cognitive function.

In certain embodiments, a test of responsiveness may distinguish between alertness (ability to orient to new stimuli) and attentiveness (ability to engage and decode stimuli).

A "test of responsiveness" is any combination of one or more outputs to the patient (such as one or more outputs provided by output device 198) and one or more responsiveness inputs received from the patient (such as one or more inputs provided by input device 199 or patient input unit 2375). Typically, it will take some length of time for the human brain to decode a stimulus and encode a response, whether correct or incorrect.

In the embodiment shown in FIG. 23A, the function of the input device 199 (FIG. 22B) is performed by patient input unit 2375. The patient input unit 2375 may include a magnetic signal input sensor (such as, for example, a Reed switch) or a tap input sensor, among others. In one embodiment, the patient input unit 2375 may also be used to allow the patient to request of the medical device 2300 alterations in a therapy regimen, such as to relieve an acute symptom of the patient's disease, to intervene with the intent of forestalling a medical event, or to minimize adverse effects of the therapy at particular times.

Results of the test of responsiveness include, but are not limited to, the correctness of an input and the time required by the patient to provide the input after receiving the output. From the various results of the test, one or more measures of the patient's responsiveness may be calculated, as will be discussed in more detail below.

In certain embodiments, one or more autonomic and/or neurologic indices may give information relating to the patient's attention and/or effort given to the test. For example, pupillary information, such as blink frequency, blink duration, fixation frequency, dwell time, saccadic extent, and mean pupil diameter, any or all of which may be normalized for ambient lighting or other environmental factors, and/or to a baseline, can be used by the person of ordinary skill in the art to determine whether the patient is paying attention to the test. For another example, electromyography (EMG) may give information about the patient's facial muscle tone, which can be used by the person of ordinary skill in the art to gauge the patient's effort given to the test.

In one embodiment, the test comprises the serial and simultaneous presentation of a pair of visual "stimuli" (such as the letter "A" and a square "☐") on a output device 198 (FIG. 1B). The position of the letter on either half of the screen (i.e., left "A ☐", or right "☐ A") may be randomly chosen for each presentation and the patient instructed to immediately make an input according to which side of the screen (left or right) on which the letter A appears. In one embodiment, the input comprises pressing one of two buttons, one button representing left and the other representing right. A correct press may then correspond to pressing the button ipsilateral to the side of the screen where the letter A was displayed. Test complexity may be increased (as needed) by displaying the stimuli in the vertical plane and alternating this (randomly) with the horizontal display or by randomly switching between stimuli during a test. For example, the patient may be instructed to press the button ipsilateral to the letter, except when the square is filled with a solid color (other than the background color), in which case the button ipsilateral to the side where the filled square appears should be pressed. This test may be triggered by a POMEDA or in response to a NOMEDA to allow comparison and quantification of changes in performance during algorithm-triggered and non-algorithm-triggered periods.

During the test, as soon as the subject presses either button, or after a maximal presentation time (e.g., 1 s) had elapsed, in case of no response, each stimulus presentation is removed (resulting in a blank screen) until the next stimuli. At the end of each presentation, a random timer (with appropriate upper and lower limits) can be set, the expiration of which triggers the next presentation. A fixed number of stimuli, such as 36, may be presented in each testing session, or the number of stimuli may be made a function of event duration and/or severity as derived from an autonomic or neurologic index value, or the number of stimuli may be made a function of results of one or more previous stimuli (e.g., if the patient's results show substantially full cognitive function for one or more trials of an seizure test, the number of further stimuli may be increases to better assess cognitive performance). Inter-trial presentation time intervals may, in one embodiment, be randomly chosen from a finite set of time intervals, such as from the set {0.5 s, 1.0 s, 1.5 s, 2.0 s}, to minimize adaptation and better assess performance.

Although a single test may be administered to the patient, such as during a medical event, such as a seizure, in other embodiments, multiple identical or different tests may be administered. In one embodiment, when the patient's medical condition is epilepsy, tests can be administered at a plurality of times, wherein at least one of the plurality of times is ictal (i.e., during an epileptic medical event) and at least one of the plurality of times is nonictal (i.e., at a time not during an epileptic medical event). A test administered at a nonictal time may be referred to herein as a "baseline" test. In embodiments wherein the patient's medical condition is not epilepsy, tests may similarly be administered during a medical event, not during a medical event, and/or during other times.

The baseline test or the difficulty thereof may be adjusted by the clinician in view of the patient's general condition, e.g., a pediatric patient, a geriatric patient, or a mentally challenged patient may require a simpler baseline test, if the patient has difficulty completing a more complicated baseline test in a short period of time.

The test may also be administered to patients suffering from neurological or psychiatric disorders and/or to subjects free from such disorders.

The patient's responsiveness may be determined by responsiveness determination unit 2387. The responsiveness may be determined from one or more values extractable from results of the test, such as the correctness of an input (such as a fraction or percentage of correct inputs), or the time required by the patient to provide the input after receiving the output, among others.

In one embodiment, multiple separate tests may be administered having various difficulty levels or the level of difficulty of a single test may be increased gradually or suddenly or different levels of difficulty may alternate randomly. For example, in one embodiment, a first test of responsiveness having a first difficulty level is selected and administered, and, based on the results of the first test, a second test of responsiveness having a second difficulty level is selected and administered. For comparison purposes, these tests could be administered to patients during POMEDA periods and NOMEDA periods (e.g., for epilepsy patients, during seizure and non-seizure conditions), and comparisons could be performed between tests of equivalent difficulty.

In one embodiment, the difficulty and duration of the degree of responsiveness test may be optimized according to the cost of detection or the clinician's desired balance of sensitivity (low false negative rate) and specificity (low false positive rate), and/or to account for changes in event severity over time. Doing so may require co-analysis of the degree of responsiveness test results with another indicator of a medical event, such as can be read from an autonomic (e.g., heart rate) or neurologic, (e.g., EEG) of the patient, or some other indicator that may exist or be developed.

In one embodiment specific to epilepsy patients, at the termination of a degree of responsiveness test, whether triggered by a POMEDA or not, the patient may be asked if he or she just had a seizure. This is a way to classify seizures as clinical or subclinical and an indirect way to validate detections; the patient's time-stamped response will be routed to the local database unit 2355 and/or the memory 2317, where it will be cross-referenced with an autonomic or neurologic index value if one indicative of a seizure exists at about the time the patient's response was recorded. If the patient indicates a seizure has occurred and an index indicative of a seizure exists about the time of the response (i.e., the test was triggered by a POMEDA) it is classified as clinical. If the patient responds in the negative and the index value is indicative of a seizure, it is classified as subclinical. If the patient responds that a seizure has occurred and none of the indices supports it (i.e., the test was triggered by a NOMEDA), a false negative detection is recorded. This provides quantitative information about the status of the patient's condition and about therapeutic and/or diagnostic efficacy that is not currently available and complements that provided by seizure frequency measures. It may also allow qualitative validation of other seizure severity measures. Additionally, interrogating the patient after a test has been administered, may help blind the patient to whether the test was triggered by a POMEDA, and thus whether a seizure is occurring or imminent. Asking the patient if a seizure occurred after administration of a test may be programmed to take place after each test until a sample sufficiently large to support statistical analyses has been collected, and updated based on the status of the patient's condition and the response to therapy and/or diagnosis.

In one embodiment, the responsiveness determination unit 2387 can perform a quantification of one or more measures relating to the test results and/or the patient's responsiveness. For example, if the test of responsiveness encompasses tracking the response time of the patient to deliver a correct answer to a stimulus (viz., speed of response), the response time of a plurality of trials can be tracked and quantified, such as by use of measures of central tendency. The percent of correct responses may be also quantified and used alone or in conjunction with the speed of response to mark the time of onset of lack of responsiveness, and its duration.

More specifically, based on the patient's responsiveness, the responsiveness parameter unit 2388 may determine a time of occurrence of a change in the patient's responsiveness, a duration of a change in the patient's responsiveness; a magnitude of a change in the patient's responsiveness, a time interval from the indication of triggering event occurrence to a change in the patient's responsiveness; a type (e.g., motor, cognitive, or both) of change in the patient's responsiveness, a determination of medical event severity for the patient; a formulation of a prognosis for the patient; an estimation of a risk of injury or death for the patient; and an assessment of efficacy of a therapy for the patient's medical condition, or some other parameter. The determination may require acquisition of an adequate sample or samples of patient results of responsiveness tests. For example, the responsiveness parameter unit 2388 may compare the patient's responsiveness at a first time to a database of time-ordered prior measures of responsiveness (which may be patient-specific or data from a plurality of patients), which may be stored in local database unit 2355 or database unit 2350, and then review the set of measures in the database taken from time points after each appearance in the database of a measure reflective of the patient's responsiveness at the first time to determine whether the patient is having a medical event, the patient's baseline responsiveness, the patient's long-term prognosis, or the like.

Strictly speaking, in embodiments where the medical condition is epilepsy, the seizure severity calculated here relates to loss of function, not a seizure as an electroencephalographic event. However, the duration, severity, or both of a loss of function may be used as reasonable approximations and/or indicators of the duration and severity of at least some types of seizure.

For example, if a plurality of trials of a responsiveness test are triggered by a POMEDA, the medical event duration may be approximated as the time between the first iteration of the test in which the patient responded incorrectly or failed to respond to three consecutively presented stimuli and the next subsequent iteration of the test in which the patient responded correctly. Another relevant measure of severity—the latency from seizure detection to loss of function—may be determined by the time between an indication of event occurrence (e.g., a POMEDA) to the first iteration of the test in which the patient responded incorrectly. Changes in the latency from seizure detection to loss of function over time may be used to determine whether the patient's disease state is improving, worsening, or remains about the same.

For example, if the speed of response, the correctness of the response, and/or the difficulty of response are logged for each of a plurality of iterations of the test, the sum of response times for iterations above the baseline (optionally weighted by the correctness and/or difficulty) and the times at which those iterations were administered can be used to calculate an area under the curve, from which a medical event severity can be, in full or in part, approximated.

Figure 23B:
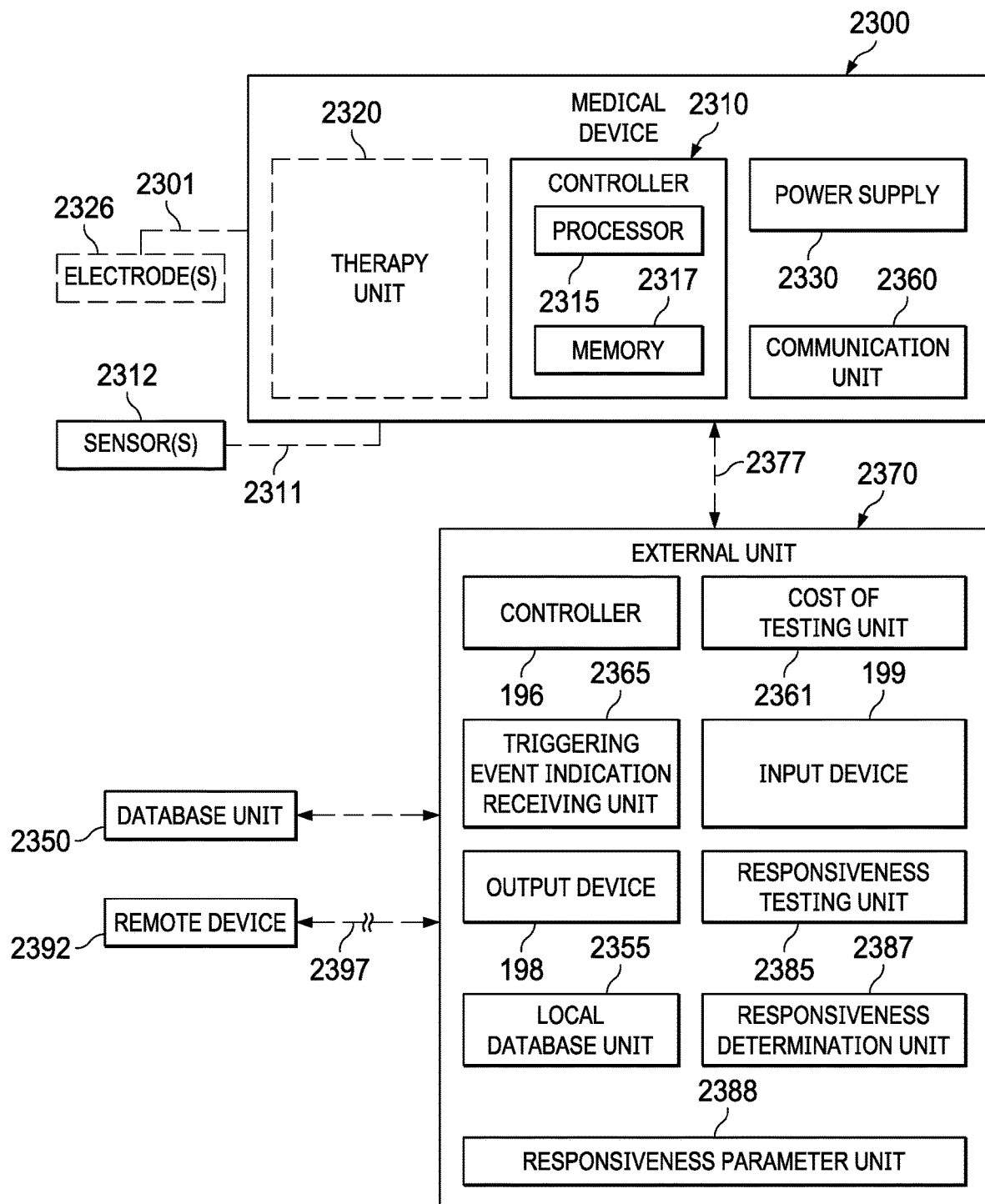
FIG. 23B is a block diagram of a medical device system that includes a medical device and a responsiveness test unit, in accordance with one illustrative embodiment of the present disclosure.

In various embodiments, one or more of the units or modules described above may be located in an external unit 2370 or a remote device 2392, with communications between that unit or module and communication unit 2360 in the MD 2300 taking place via a link 2377, which may comprise a lead, an inductive RF or similar wireless coupling, a Bluetooth or other wireless data transfer coupling, etc. For example, in one embodiment, as shown in FIG. 23B, a triggering event indication receiving unit 2365, a responsiveness testing unit 2385, a responsiveness determination unit 2387, and a responsiveness parameter unit 2388 may be located in an external unit. In embodiments in which no therapy unit 2320 or stimulation electrodes 2326, 2328 are provided, all of the functional modules may be provided in an external unit.

In one embodiment, the external unit 2370 may comprise a local database unit 2355. Optionally or alternatively, the external unit 2370 may also be coupled to a database unit 2350, which may be separate from external unit 2370 (e.g., a centralized database wirelessly linked to external unit 2370). The database unit 2350 and/or the local database unit 2355 are capable of storing various patient data. In certain embodiments, the memory 2317 is also capable of storing various patient data. These data may comprise time stamped: a) patient responsiveness data, including test results and measures of responsiveness, b) number of detections (i.e., POMEDAs) and their severity expressed numerically as the product of peak index value and the time (in sec or min) which the index value spends above a baseline; c) medical event classification (e.g., whether a seizure is clinical or subclinical, and if clinical, if it is simple partial, complex partial, or generalized); d) therapy parameter data; e) disease status as assessed with autonomic and neurological indices; f) injury risk; h) event button presses or patient input, all data being updated as its flow rate demands (as will be discussed in more detail below). The time stamp may have any particular desired granularity, such as to the hundredth of a second. The database unit 2350 and/or the local database unit 2355 may comprise data for a plurality of patients, and may be organized and stored in a variety of manners, such as in date format, severity of disease format, latency (time difference) between a detection event (i.e., a POMEDA) and a loss of responsiveness as indicated by the failure of the patient to respond to one or more test stimuli, etc. The database unit 2350 and/or the local database unit 2355 may be relational databases in one embodiment. The database unit 2350 and/or the local database unit 2355 may store various patient data.

In one embodiment, the database unit 2350 and/or the local database unit 2355 allow the patient, a caregiver, a medical practitioner, or another interested person to follow the patient's responsiveness under various changing conditions, such as under various disease conditions (e.g., for epilepsy patients, during preictal, ictal, and/or postictal times), various times of day, month, and/or year, various therapy parameters, etc.

Figure 24A:
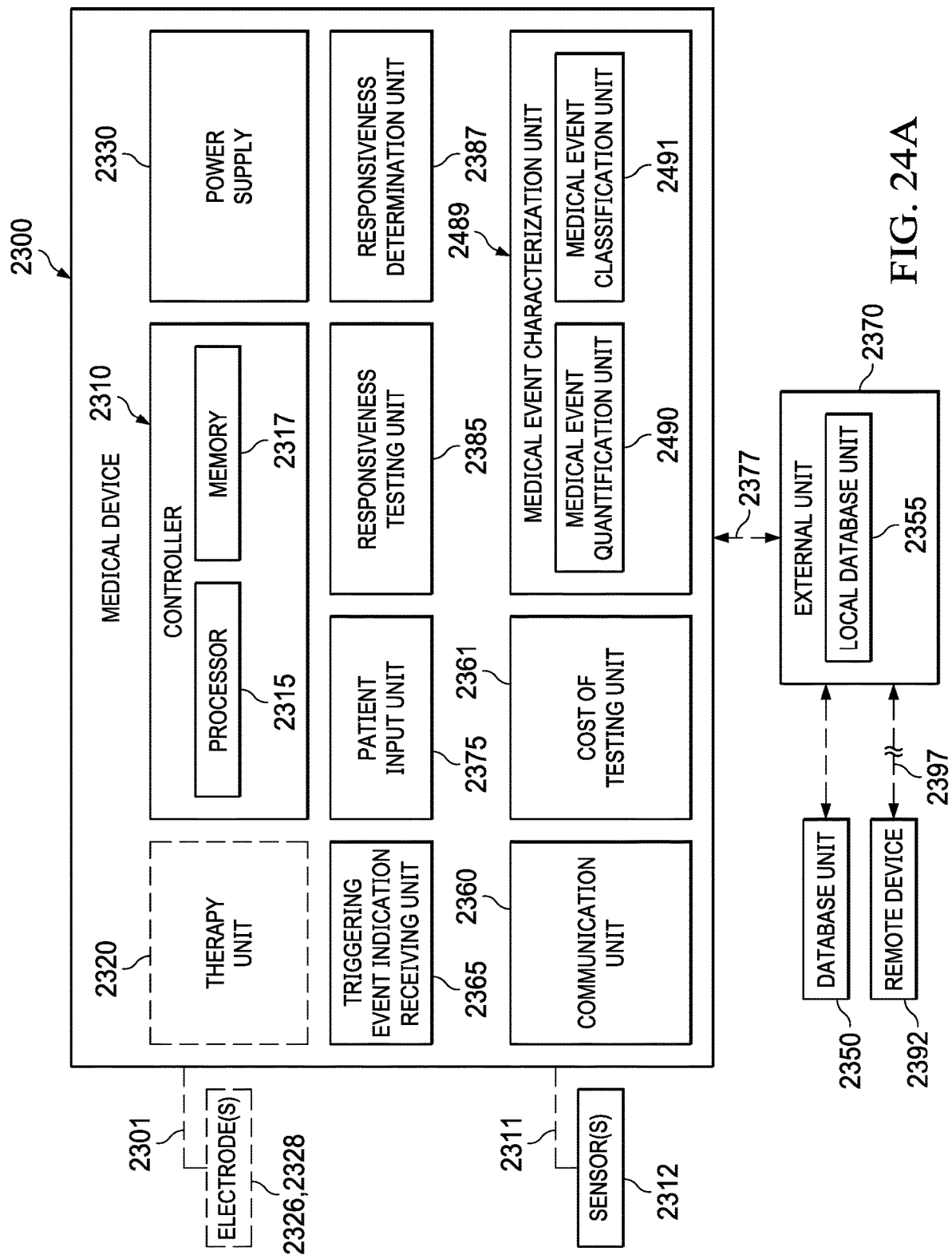
FIG. 24A is a block diagram of a medical device system that includes a medical device, in accordance with one illustrative embodiment of the present disclosure.
Figure 24B:
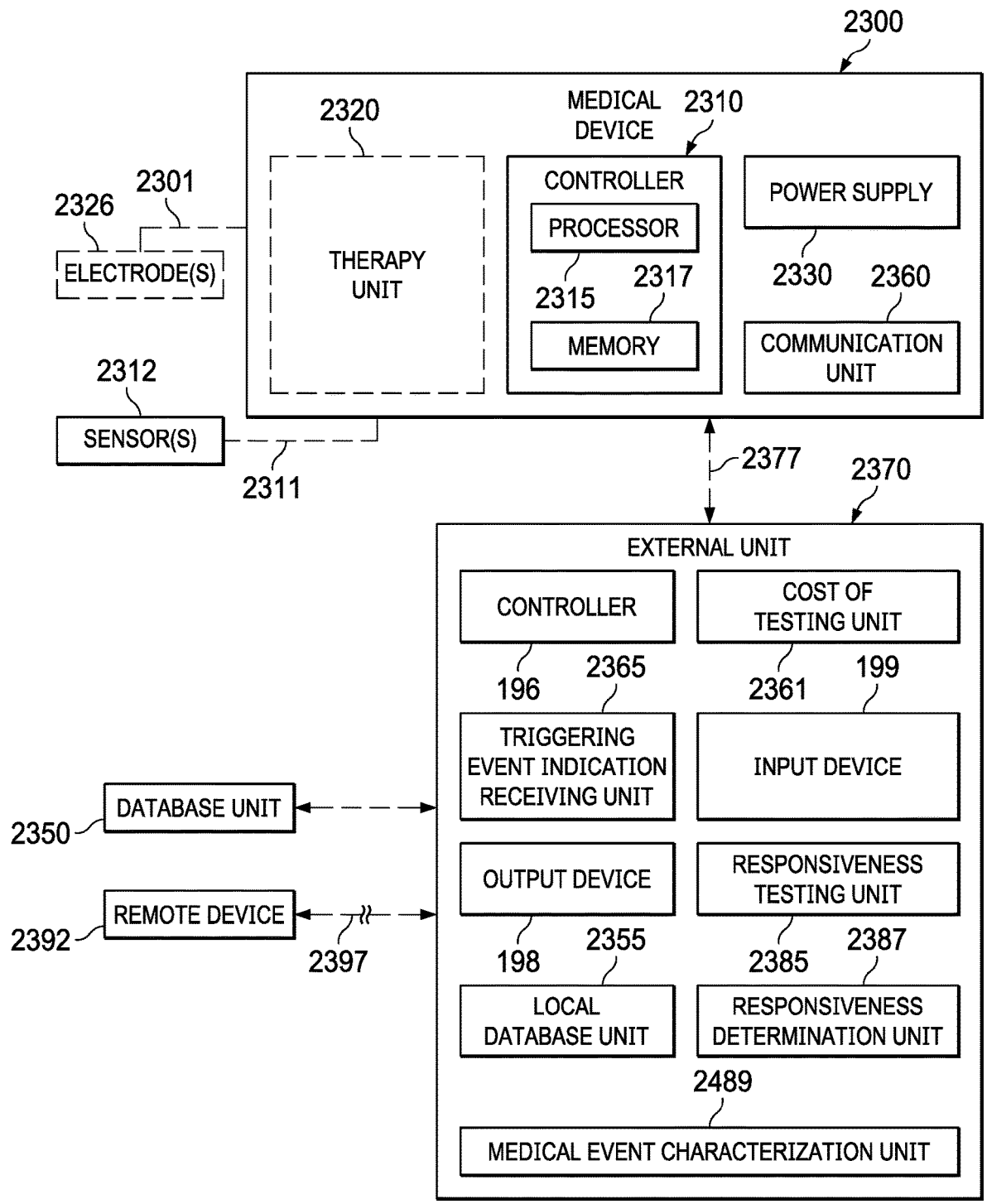
FIG. 24B is a block diagram of a medical device system that includes a medical device and a responsiveness test unit, in accordance with one illustrative embodiment of the present disclosure.

FIGS. 24A-24B contain many like elements to FIGS. 23A-23B, and those like elements will not be described further. FIGS. 24A-24B contain a medical event characterization unit 2489, comprising a medical event quantification unit 2490 and a medical event classification unit 2491. Based on either or both of the patient's responsiveness and one or more other indicators of a medical event (e.g., a POMEDA from an algorithm based on the patient's heart rate or heart rate variability, among others), the medical event quantification unit 2490 may determine a duration or a severity of a medical event and/or the medical event classification unit 2491 may classify the medical event by duration, severity, and/or estimated type (e.g., for seizures, partial or generalized, simple or complex, etc.). For example, the medical event characterization unit 2489 may determine a series of measures in a database of time-ordered values, which may be stored in local database unit 2355 or database unit 2350, in which many or all of the measures reflected a medical event, and determine the duration of a medical event by comparing time-stamps of the first and last values in the series comparable to a measure of the patient's baseline responses. A severity of a medical event may, for example, be calculated from the sum, average, median, mean, nth percentile, or area under the curve of one or more measured values in the series.

Figure 25A:
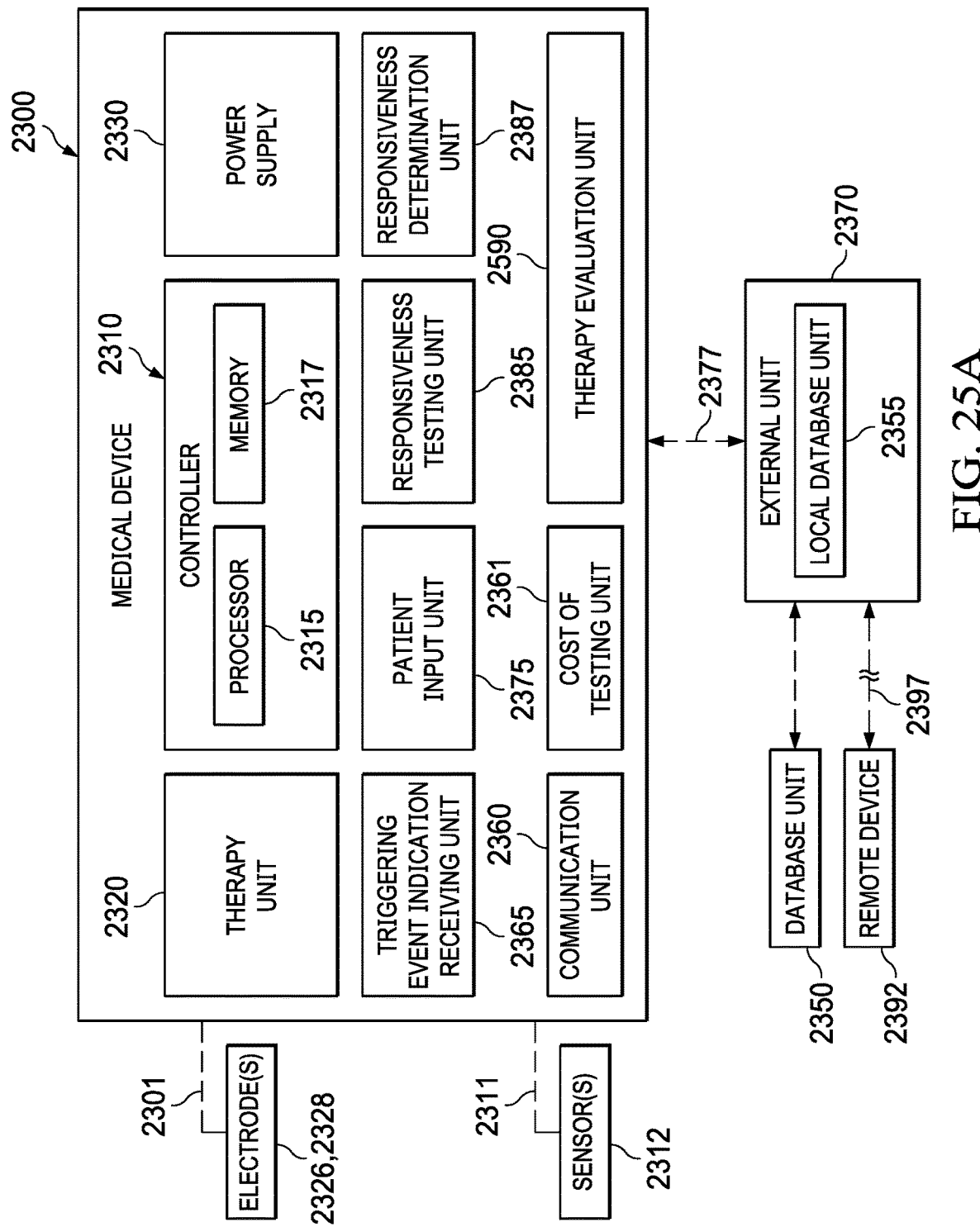
FIG. 25A is a block diagram of a medical device system that includes a medical device, in accordance with one illustrative embodiment of the present disclosure.
Figure 25B:
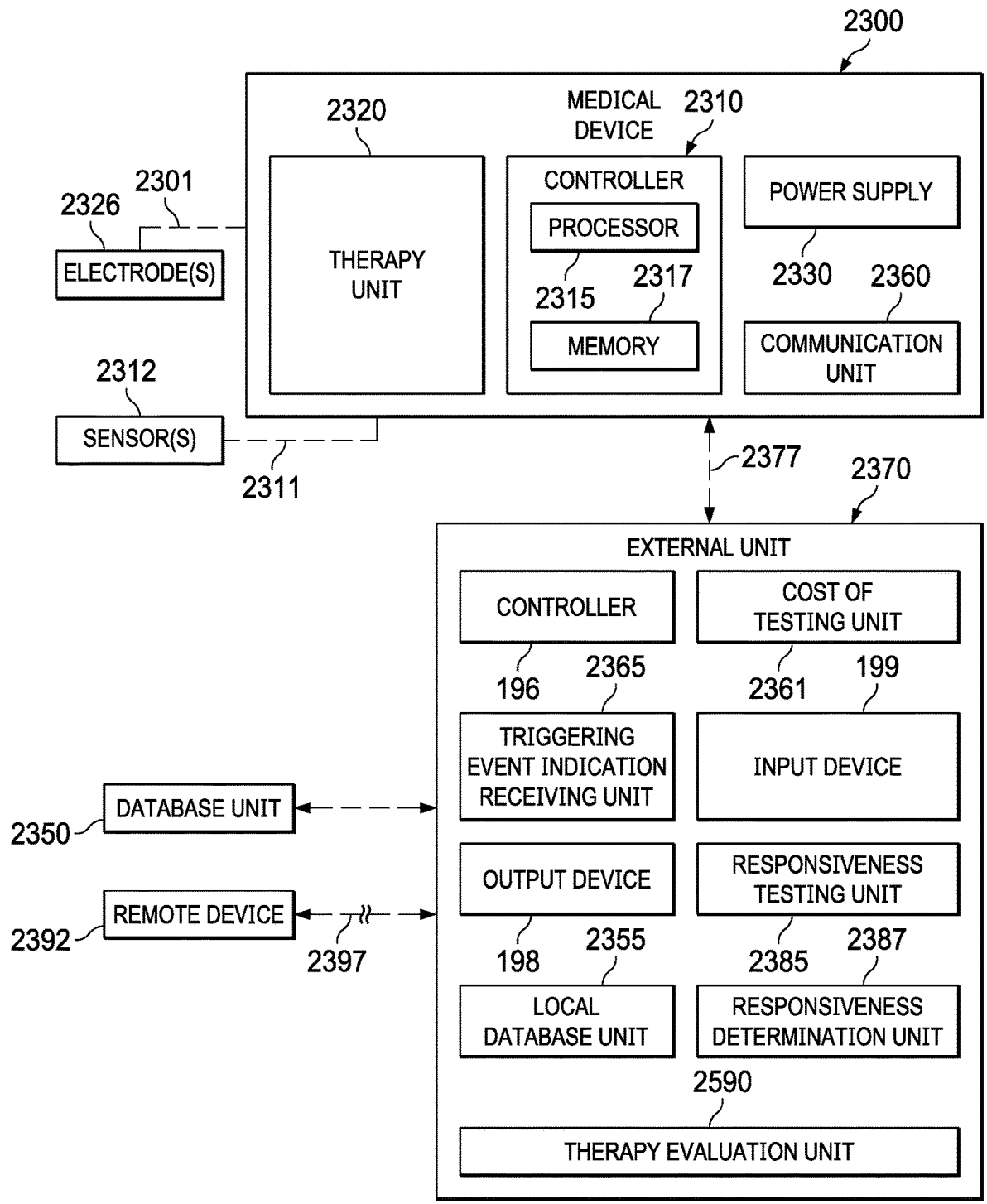
FIG. 25B is a block diagram of a medical device system that includes a medical device and a responsiveness test unit, in accordance with one illustrative embodiment of the present disclosure.

FIGS. 25A-25B contain many like elements to FIGS. 23A-23B or FIGS. 24A-24B, and those like elements will not be described further. FIGS. 25A-25B illustrate an embodiment of the disclosure having a therapy evaluation unit 2590. Therapeutic efficacy of a therapy provided by a therapy unit 2320 can be assessed by determining if there is a decrease in the severity or duration of the patient's loss of responsiveness over time. Decreases in value of any of the autonomic or neurologic indices—including electrical activity recorded directly from the brain—do not provide direct or reliable information about the state of a patient's responsiveness. Based on the patient's responsiveness, the therapy evaluation unit 2590 may determine an efficacy of a therapy for a patient's medical condition. For example, the therapy evaluation unit 2590 may compare a measure of the patient's responsiveness when a therapy is administered by a therapy unit 2320 compared to when therapy was not administered. Alternatively, the therapy may be administered by other than a therapy unit 2320, e.g., by the patient's oral ingestion of a medication, or the like. These comparisons are performed by the therapy evaluation unit 2590 using measures in a database of time-ordered values, which may be stored in local database unit 2355 or database unit 2350. For example, the measure may be a correct response time to a test, optionally weighted by difficulty of the test, and optionally smoothed as the mean, median, or the like of a series of values. If the correct response time(s) for administrations of the test is/are lower when a therapy is administered than when it is not, the therapy's efficacy may be quantified, for example, as the percent reduction of the duration and/or severity of the patient's loss of responsiveness. Efficacy may also be quantified as the change in the latency time from medical event detection (as determined by, e.g., a POMEDA) to loss of function (e.g., the first iteration of the test in which the patient responded incorrectly) over the course of a desired time interval such as weeks, months, or years.

A therapy evaluation unit 2590 may be desirable for inclusion in a medical device system wherein the medical device system delivers a therapy for a seizure event to the patient. In one embodiment, the therapy for the seizure event is selected from the group consisting of electrical stimulation of a cranial nerve of the patient, thermal manipulation of the cranial nerve of the patient, electrical stimulation of the brain of the patient, thermal manipulation of the brain of the patient, delivery of a chemical agent to the patient via the bloodstream, the cerebrospinal fluid or directly to brain tissue, performance of a motor task, performance of a perceptual task, performance of a cognitive task, and two or more thereof.

In one embodiment, the therapy evaluation unit 2590 may be incorporated into the medical device 2300 (see, for example, FIG. 25A).

Though not shown, the person of ordinary skill in the art will understand a medical device system according to the present disclosure may comprise any two or all three of a responsiveness parameter unit 2388, a medical event characterization unit 2489, and a therapy evaluation unit 2590. For example, the medical device system may comprise both the medical event characterization unit 2489 and the therapy evaluation unit 2590, and the therapy evaluation unit 2590 may incorporate in its therapy evaluation event duration and/or event severity values reported by the medical event characterization unit 2489.

One or more of the blocks illustrated in the block diagram of the MD 2300 in FIGS. 23-25 may comprise hardware units, software units, firmware units, or any combination thereof. Additionally, one or more blocks illustrated in FIGS. 23-25 may be combined with other blocks, which may represent circuit hardware units, software algorithms, etc. Additionally, any number of the circuitry or software units associated with the various blocks illustrated in FIGS. 23-25 may be combined into a programmable device, such as a field programmable gate array, an ASIC device, etc.

The medical device system of one embodiment of the present disclosure provides for software module(s) that are capable of acquiring, storing, and processing various forms of data, such as patient data/parameters (e.g., demographic data, physiological data such as autonomic and neurologic index values, such as heart rate or EKG morphology changes or breathing rate or pattern changes, among others, disease status (progression, regression, or stabilization), quality of life data, etc.). In one embodiment, the software modules(s) are further capable of acquiring, storing, and processing therapy parameter data. Therapy parameters may include, but are not limited to, electrical signal parameters that define therapeutic electrical signals delivered by the device, medication parameters, and/or any other therapeutic treatment parameter. In an alternative embodiment, the term "therapy parameters" may refer to electrical signal parameters defining the therapeutic electrical signals delivered by the IMD. Therapy parameters for a therapeutic electrical signal may also include, but are not limited to, a current amplitude, a pulse width, a pulse shape, a degree of charge balancing, a frequency, a pulse train pattern, an on-time, an off-time, etc.

In one embodiment, the present disclosure may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode may be coupled to either or both vagus nerves or a branch of either or both vagus nerves. The term "operatively" coupled may include direct or indirect coupling. Each of the nerves in this embodiment or others involving two or more cranial nerves may be stimulated according to particular activation modalities that may be independent between the two nerves.

In one embodiment, the communication unit 2360 is capable, based on the patient's responsiveness, of instructing an external device to change an operating state thereof. For example, the external device may be an automobile or other vehicle which the patient is driving, and the change in the operating state thereof may be stopping, putting the transmission into neutral, applying a parking brake, etc., or two or more thereof. For another example, the device may be a power tool, such as a circular saw, table saw, jigsaw, chain saw, power sander, lawn mower, weed trimmer, tiller, cultivator, etc., and the change in the operating state thereof may be stopping its motor or disengaging its cutting or grinding parts from the motor or a drive coupled to the motor. For another example, the device may be an oven, stove, toaster, microwave oven, or other kitchen applicants. For an additional example, the device may be a faucet, a drain, or a gate restricting access to a stairwell, balcony, swimming pool, or other location where a non-responsive person would be at risk of bodily harm or death.

Figure 26:
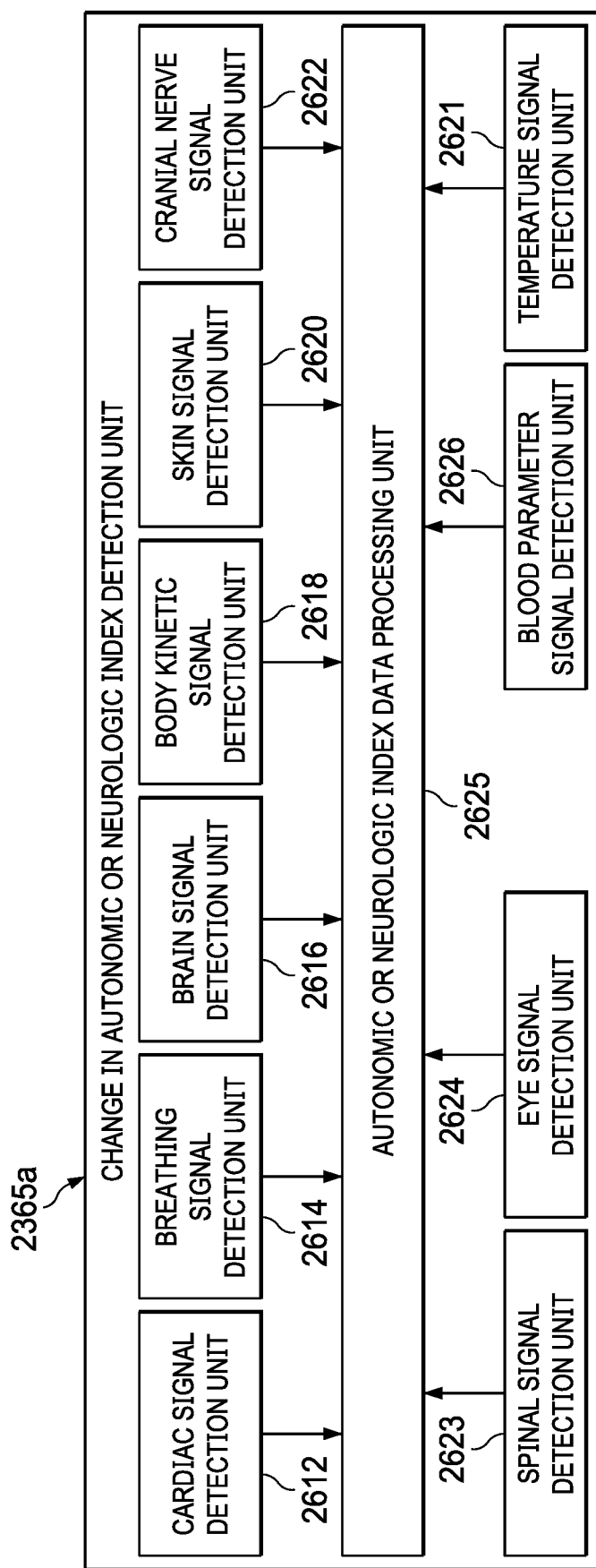
FIG. 26 illustrates a block diagram of a change in autonomic or neurologic index detection unit of the medical device system, in accordance with one illustrative embodiment of the present disclosure.

Turning now to FIG. 26, a change in autonomic or neurologic index detection unit 2365*a* is shown. In certain embodiments, autonomic or neurologic index detection unit 2365*a* can trigger an administration of the test by providing an appropriate instruction to triggering event indication receiving unit 2365 (FIGS. 23A-25B). The change in autonomic or neurologic index detection unit 2365*a* may comprise one or more signal detection units, such as a cardiovascular signal detection unit 2612, a breathing signal detection unit 2614, a brain signal detection unit 2616, a motor or kinetic signal detection unit 2618, a skin signal detection unit 2620, a temperature signal detection unit 2621, a spinal signal detection unit 2623, a cranial or peripheral nerve signal detection unit 2622, an eye (pupil or eyelid) signal detection unit 2624, and/or a blood parameter signal detection unit 2626. The cardiovascular signal detection unit 2612 is capable of detecting one or more of various cardiovascular-related signals, including but not limited to electrocardiogram (ECG) signals, heart rate (HR) signals, and heart rate variability (HRV) signals. The breathing signal detection unit 2614 is capable of detecting one or more of various breathing/respiratory signals of a patient, including, but not limited to, breath rate (BR) signals, air flow signals, and tidal volume signals. The breathing/respiratory parameters sensed by the unit 514 may include, but is not limited to, air flow measurements, volume measurements, transthoracic inductance, impedance plethysmogrphs, thoracic circumference, and pneumatic respiration, among others. Some embodiments of the unit 2614 may include at least one of a spirometer, a nasal thermocoupler measurement device, a strain gauge, a pneumatic respiration transducer, an impedance measurement device, and/or other devices capable of detecting respiratory signals.

The brain signal detection unit 2616 is capable of detecting one or more of various brain signals, including, but not limited to, EEG signals, field potentials or multiunit activity; fast neuronal oscillations (>100 Hz); near DC or DC potentials, event-related potentials, neurotranmitter concentrations, ionic concentrations, pH, glucose concentrations, free radicals and/or other brain signals known to those skilled in the art. The body kinetic signal detection unit 2618 may include an accelerometer, an inclinometer, and/or other kinetic or force measurement devices capable of detecting movement in one or more areas or limbs of the patient's body. The skin signal detection unit 2620 is capable of detecting one or more of various skin parameters, such as impedance or other bioelectrical measurements relating to the skin, sweat amount, sweat chemical composition, etc. The cranial nerve signal detection unit 2622 is capable of detecting one or more of various signals relating to cranial nerves, such as amplitude, rate and direction of action potential traffic, type of fiber (by size and presence or absence of myelinization) activated, polarity, transmembrane voltage parameter, etc. The temperature signal detection unit 2621 is capable of detecting one or more of various types of body temperature parameters, including, but not limited to core temperature changes, organ (e.g., brain) or body part (e.g., facial) temperature, etc. The unit 2621 may include an infrared sensing device, a chemical-reaction based temperature sensing device, a direct temperature measurement device, etc. The spinal signal detection unit 2623 is capable of sensing one or more of various spinal signals, including, but not limited to, motor neuron signals, sensory pathway signals, autonomic signals, etc.

The eye signal detection unit 2624 is capable of detecting one or more of various signals relating to the eye, including autonomic functions including, without limitation, pupil width and dilation, eyelid movement and/or phenomena such as mydriasis, miosis, ptosis and/or hippus. The blood signal detection unit is capable of detecting one or more blood parameters including, without limitation, oxygen saturation, glucose concentration, and/or blood pH.

Each unit 2612-2626 present in the change in autonomic or neurologic index detection unit 2365a is capable of communicating detected signals, or data generated from the detected signals, to an autonomic or neurologic index data processing unit 2625, which is capable of determining a change in an autonomic or neurologic index, which may involve accessing prior autonomic or neurologic index information stored in, e.g., memory 2317, local database unit 2355, and/or database unit 2350.

The autonomic or neurologic index data processing unit 2625 may comprise one or more subunits capable of performing autonomic or neurologic index quantification, autonomic or neurologic index classification, or both. In particular, autonomic or neurologic index data processing unit 2625 may process one or more autonomic or neurologic signals from units 2612-2626 according to one or more event detection algorithms to provide an appropriate instruction (e.g., a POMEDA or a NOMEDA) to triggering event indication receiving unit 2365 (FIGS. 23A-25B) to trigger an administration of the test.

Figure 27A:
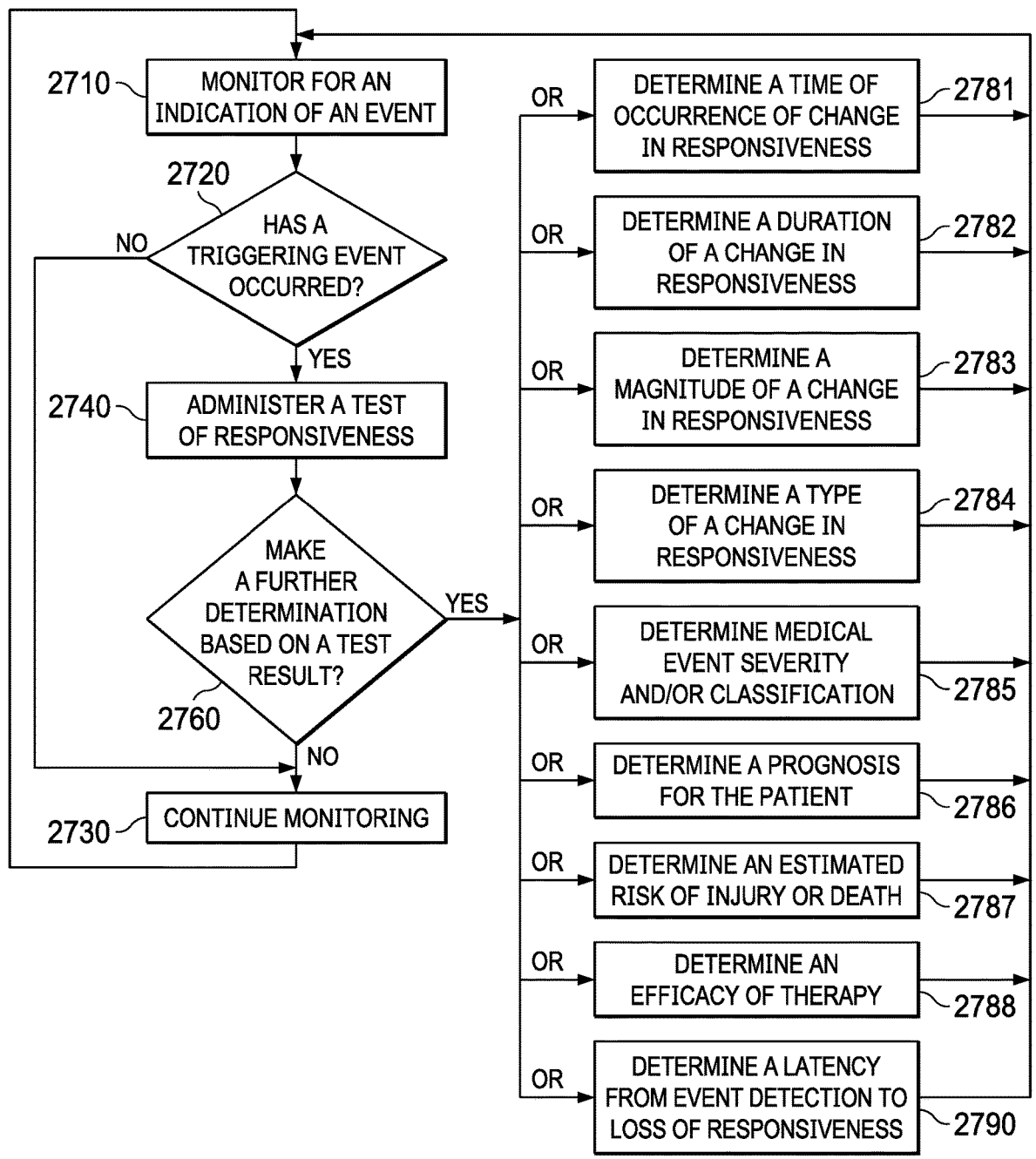
FIG. 27A illustrates a flowchart depiction of determining a responsiveness of a patient, in accordance with one illustrative embodiment of the present disclosure.

Turning now to FIG. 27A, a flowchart depiction of a method of determining a responsiveness of a patient is shown, in accordance with one illustrative embodiment of the present disclosure. Monitoring 2710 for an indication of a triggering event, such as a signal from autonomic or neurologic index detection unit 2365a, is performed. Monitoring 2710 may be performed at any desirable time scale (from milliseconds to years), sampling rate (in Hz), and digital precision (in bits), which may be relatively rapid or relatively slow depending upon the nature of the signal being measured. Rapid sampling may be made for ECoG signals (e.g., about 2 KHz) or ECG signals (200 Hz to 1000 Hz), among others. Much slower sampling rates may be used for other autonomic signals, including rates as slow as once every 1 sec, 5 sec, 10 sec, 15 sec, or longer, including DC recording. Data collection or sampling may be continued or interrupted if one or more steps 2740-2788 are performed. Data can also be conditioned according to techniques known in the art, if desired.

After monitoring 2710 is performed, a determination 2720 is made as to whether a triggering event is occurring or has occurred. The triggering event may be a medical event (such as a medical event indicated by autonomic or neurologic index detection unit 2365a) or a non-medical event, such as a manual signal from a patient or caregiver, or a signal from one or more random timers indicating the need for an administration of a responsiveness test. If no triggering event occurred, monitoring is continued 2730. On the other hand, if a triggering event did occur, a test of responsiveness can be administered 2740. In one embodiment, administration 2740 of the test of responsiveness follows the description of test administration set forth above. After administration 2740, a decision 2760 is made as to whether a further determination should be made based on a test result. The decision parameters may be fixed in manufacture of a device or software implementing the method, reprogrammable by a practitioner during ongoing implementation of the method, and/or automatically adjustable by the device or software during ongoing implementation of the method. In one embodiment, the determination 2760 may function such that a "no" decision in step 2760 indicates a normal or baseline responsiveness of the patient. In this embodiment, following a "no" decision, monitoring may be continued 2730.

The factors considered in the determination 2760 may be adjusted to increase or decrease the specificity, sensitivity, or both of the process.

If a further determination is to be made based on the test result, i.e., upon a "yes" decision in step 2760, one or more determinations 2781-2790 may be made. In the depicted embodiment, these determinations 2781-2790 (listed in no particular order) include (2781) a time of occurrence of a change in the patient's responsiveness, (2782) a duration of a change in the patient's responsiveness; (2783) a magnitude of a change in the patient's responsiveness, (2784) a type (e.g., motor or cognitive) of change in the patient's responsiveness, (2785) a determination of event severity and/or classification for the patient (e.g., a classification of a seizure into clinical or subclinical and/or a classification of a clinical seizure into simple partial, complex partial, or generalized); (2786) a formulation of a prognosis for the patient; (2787) an estimation of a risk of injury or death for the patient; (2788) an assessment of efficacy of a therapy for the patient's medical condition; and (2790) a latency from medical event detection to loss of function. Steps 2781-2790 may be executed in parallel (simultaneously), in the order that maximizes operational efficiency and therapeutic efficacy or in any order as required by the application. If monitoring (step 2710) has been discontinued while any of the other steps (2781-2790) are being performed, step 2710 will resume immediately upon termination of steps 2781-2790.

The determining steps 2781-2790 may be performed in their entirety before returning to monitoring step 2710, but they need not be. In one embodiment, the "yes" decision in step 2750 instructs an appropriate device or software to initiate determining steps 2781-2790, gives the device or software information gathered in steps 2720, 2740, and/or 2760 to allow the determining steps 2781-2790 to be executed and perform calculations using that information, and, if needed, gives the device or software permission to access a database, such as may be stored in, e.g., memory 2317, local database unit 2355, and/or database unit 2350. Thereafter, the device or software may implement determining steps 2781-2790 in parallel or in any desired order with resumed monitoring 2710.

Also, it should be noted that not all medical events, and not even all epileptic seizures, are necessarily associated with impaired or abnormal responsiveness but these (and those associated with impaired responsiveness) may be associated with distinctive feelings, sensations, emotions, illusions, hallucinations, thoughts, or impulses/behaviors. In one embodiment, the approaches and methods described herein allow the classification of epileptic seizures into clinical (subjective or objective phenomenology is present) or subclinical (neither subjective nor objective phenomenology is present) seizures, wherein the clinical seizures may be further classified into simple partial, complex partial, or generalized seizures. The distinction between complex and secondary generalized may be made using other seizure severity measures (e.g., peak heart rate x duration). For simple partial seizures, one or more autonomic and/or neurologic indices and/or features from each signal thereof may be used to distinguish seizures from non-ictal tachycardia.

Figure 27B:
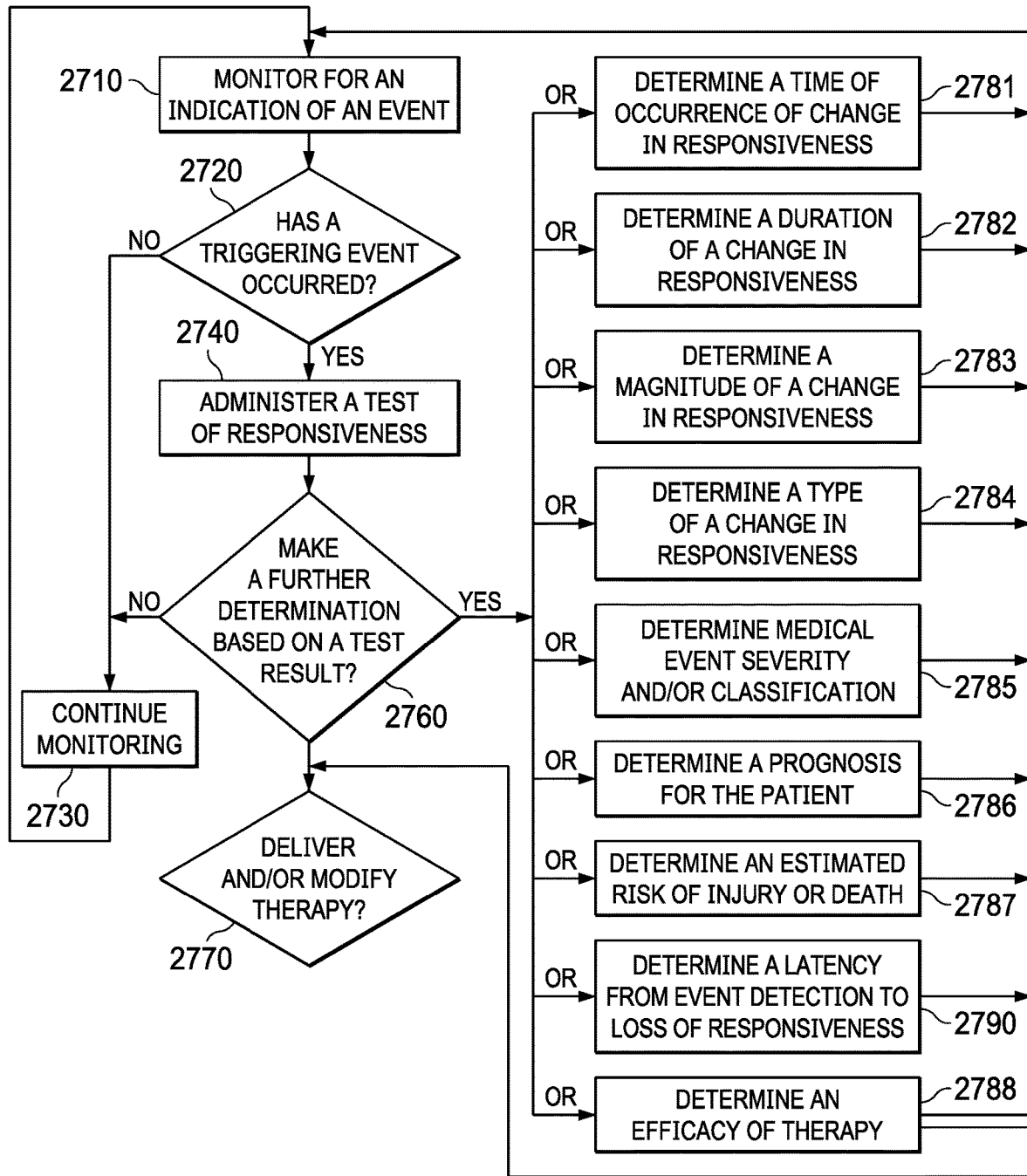
FIG. 27B illustrates a flowchart depiction of determining a responsiveness of a patient in combination with the delivery and/or modification of therapy, in accordance with one illustrative embodiment of the present disclosure.

FIG. 27B contains many elements like to those of FIG. 27A, which will not be separately discussed here. In the embodiment depicted in FIG. 27B, upon a "yes" decision 2760, and/or a determination of a latency 2790, in addition to the determining steps 2781-2790, a decision 2770 is made to deliver and/or modify therapy. For example, the decision 2770 may be to initiate delivery of electrical stimulation to a neural structure, such as a cranial nerve; change one or more parameters defining an electrical signal, such as the pulse width, pulse frequency, on-time/off-time ratio, or other parameters of electrical stimulation to a neural structure, such as a cranial nerve, deliver or change the dosage of a drug administered to the patient; etc.

Figure 27C:
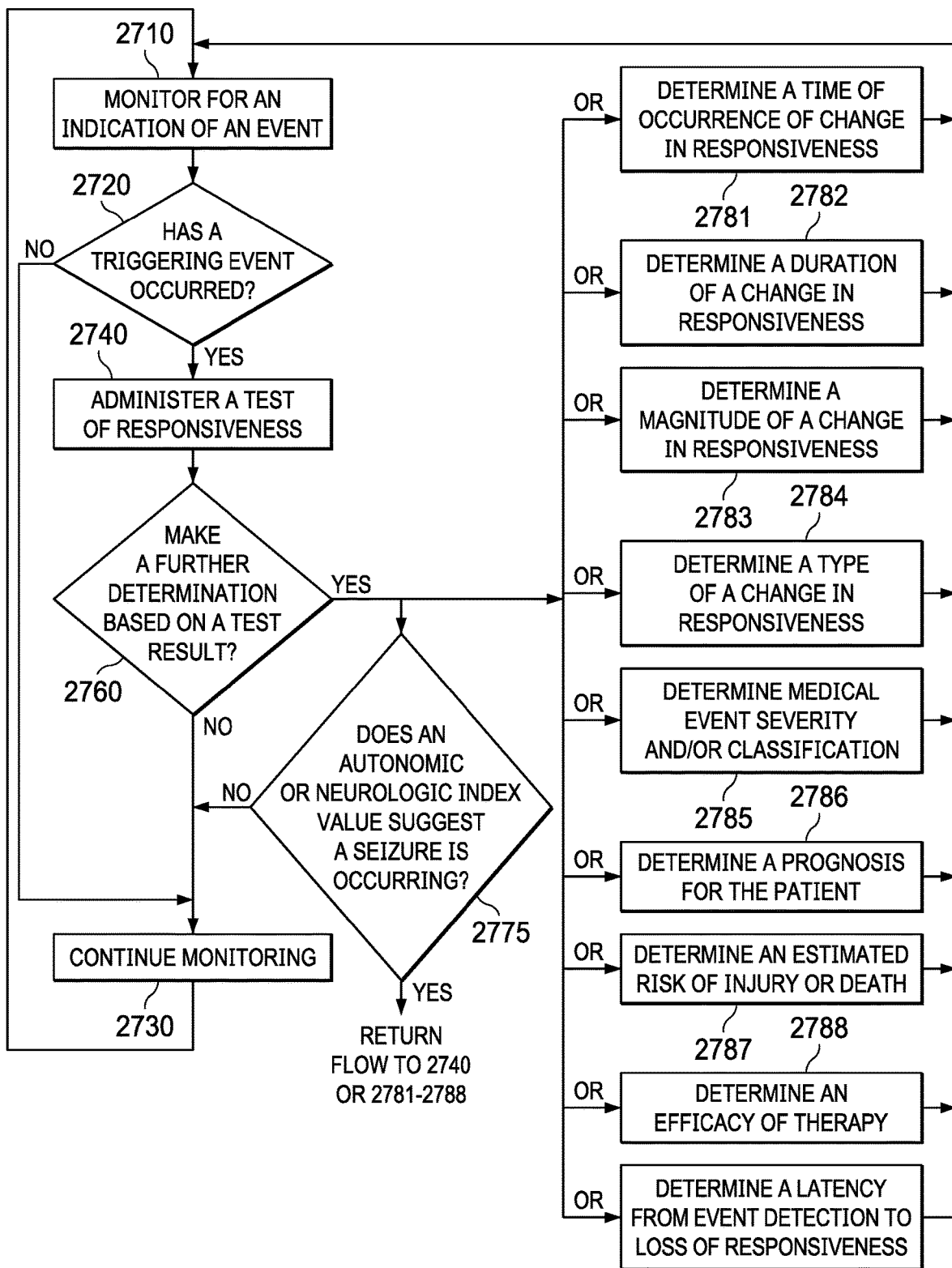
FIG. 27C illustrates a flowchart depiction of determining a responsiveness of a patient in combination with an override based on an autonomic or neurologic index value, in accordance with one illustrative embodiment of the present disclosure.

FIG. 27C contains many elements like to those of FIG. 27A and/or FIG. 27B, which will not be separately discussed here. In the embodiment depicted in FIG. 27C, upon either or both of the "yes" decisions yielded by decision nodes 2720 and 2760, the process flow may be directed to step 2775, wherein at least one autonomic or neurologic index value as described above is considered to suggest whether a medical event is occurring (e.g., whether a POMEDA or a NOMEDA signal is present). For example, the autonomic or neurologic index value may be heart rate, and a heart rate value of at least 100 BPM may be taken as suggestive that an epileptic medical event is occurring. Generally, one or more values of one or more indices can be taken as suggestive that a medical event is occurring. If the autonomic or neurologic index value suggests a medical event is occurring, flow may be returned to the step subsequent to the "yes" decision, e.g., administering 2740 or any one or more of the determining steps 2781-2790. If the autonomic or neurologic index value suggests a medical event is not occurring, flow may be directed to the continue monitoring step 2730.

Figure 27D:
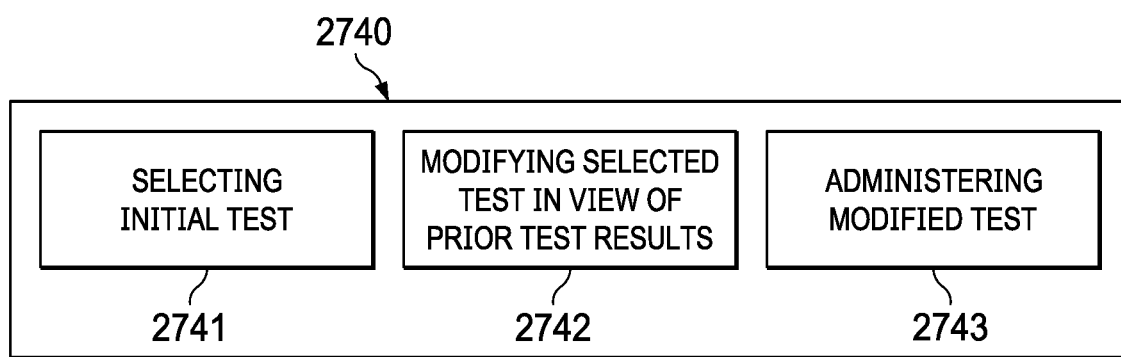
FIG. 27D depicts one particular embodiment of administering a test of the patient's responsiveness, in accordance with one illustrative embodiment of the present disclosure.

FIG. 27D depicts in more detail one particular embodiment of administering 2740. In the embodiment depicted in FIG. 27D, a test is initially selected 2741 based on one or more of the patient's baseline, the time of day, week, month, or year, values of one or more autonomic indices, or two or more thereof, among others.

The initially selected test may be modified 2742 in view of prior test results or based on an ongoing event. "Modified" is used herein to mean the initially selected test may be made more difficult, less difficult, longer, shorter, replaced with a different cognitive test, or two or more thereof. For example, modifying may encompass increasing the volume of an auditory test, switching from a visual to a tactile or auditory test, or switching from a more complex cognitive test to a simpler test, among others.

The prior test results may be one or more of historical results over days, weeks, months, or even longer, or the results of previous iterations of the method administered during the same presumptive event.

The person of ordinary skill in the art will understand that variations in any of the depicted methods may be performed. For example, embodiments shown in FIGS. 27A-27C may be implemented together. For one example, the embodiment of FIG. 27C may be modified such that steps 2710-2760 are used to override a POMEDA determined from an autonomic or neurologic index value. For another example, the embodiments of FIGS. 27A-27C may be implemented at different times as part of the treatment regimen of one patient. For example, at different times of day, of the week, of the month, or of the year, the clinician may find it appropriate to perform different methods depicted in FIGS. 27A-27C.

Figure 27E:
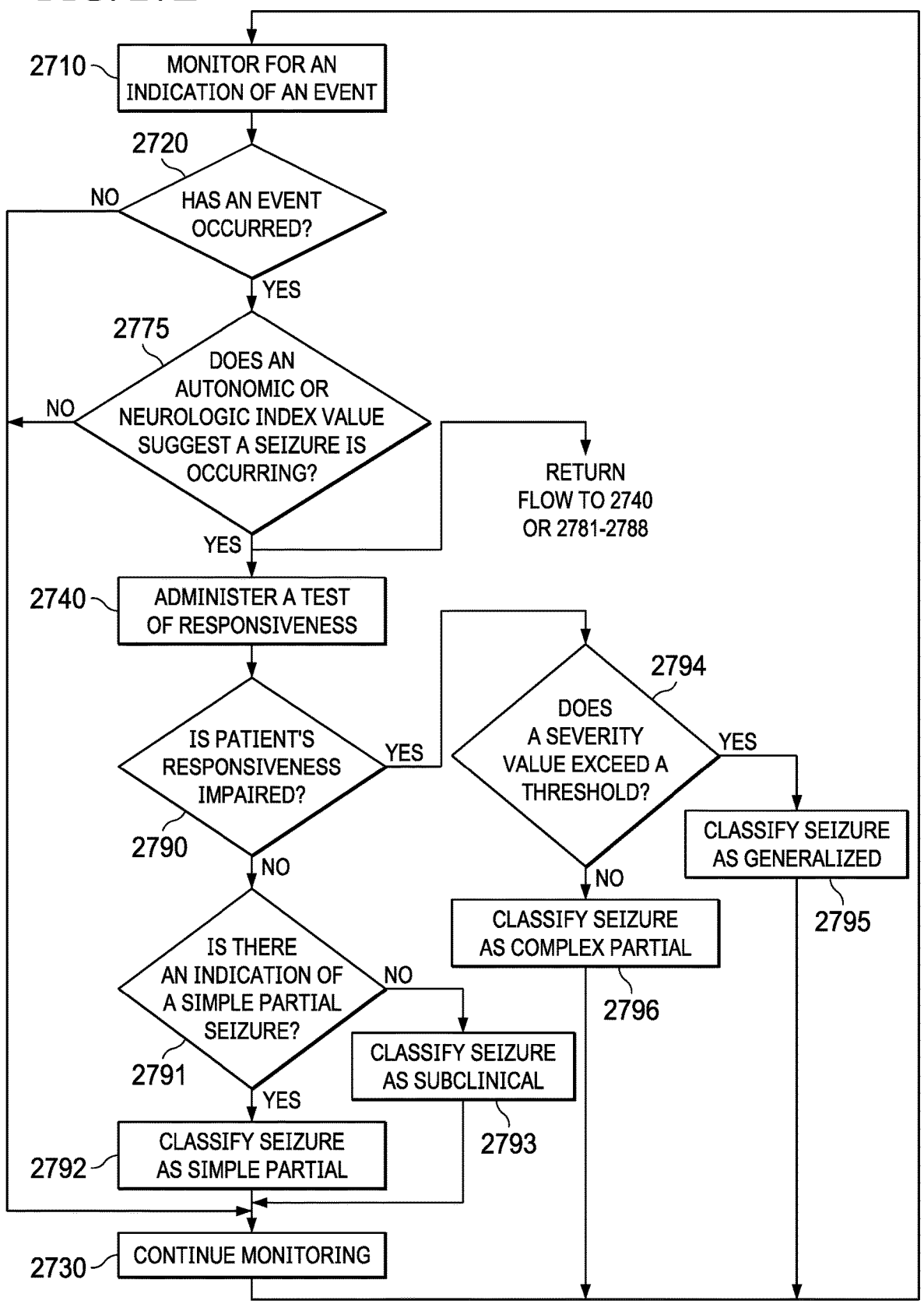
FIG. 27E depicts one particular embodiment of administering a test of the patient's responsiveness, in accordance with one illustrative embodiment of the present disclosure.

In one embodiment, shown in FIG. 27E, the triggering event is a change in an autonomic or neurologic index, such as those discussed above. Upon a "yes" decision in node 2775, flow returns to administering 2740. Thereafter, it is determined at node 2790 whether the patient's responsiveness is or is not impaired. If the patient's responsiveness is not impaired, a determination 2791 is made whether there is an indication of a simple partial seizure. In one embodiment of the determination 2791, the subject or an observer is asked if there is/was a clinical manifestation of a seizure, such as a sensation (typical for the seizure) or a visible manifestation. If yes, the seizure identified by node 2775 is classified 2792 as a simple partial seizure. If no, the seizure identified by node 2775 is classified 2793 as a subclinical seizure.

If the patient's responsiveness is impaired, a determination 2794 is made whether a seizure severity value has exceeded a threshold. If yes, the seizure identified by node 2775 is classified 2795 as a generalized seizure. If no, the seizure identified by node 2775 is classified 2796 as a complex partial seizure.

As should be apparent from the foregoing discussion, the various method steps may be performed by one or more devices, such as a medical device 2300 in concert with an external unit 2370.

EXAMPLE

A study was conducted at a major university medical center in subjects with pharmaco-resistant localization-related epilepsies undergoing surgical evaluation. After signing the consent form, subjects were enrolled into this study in the order of admission. The surgical assessment was conducted in accordance with this institution's protocol which included discontinuation of anti-seizure drugs or reductions in dose.

Inclusion criteria were: 1. Good candidate for invasive epilepsy surgery evaluation (subjects with at least one seizure/month on two or more appropriate medications at therapeutic serum concentrations); 2. Normal motor function; 3. Normal vision with or without correction; and 4. Low average IQ or higher.

Exclusion criteria were: 1. Mental retardation; 2. Status epilepticus during evaluation prior to collection of an adequate sample of test presentations and responses; 2. Use of rescue or psychoactive or CNS depressant drugs prior to collection of an adequate sample of test presentations and responses; 3. Medical or neurological complication prior to collection of an adequate sample of test presentations and responses and 4. Subject voluntary withdrawal prior to collection of an adequate sample of test presentations and responses.

Patient information is shown below in Tables 1-2.

To estimate the latency/time to impairment of complex reaction time responses from the time of electrographic onset recorded using depth or subdural electrodes, this test was administered to each subject under two conditions: a) Randomly and b) During seizures (triggered by automated detection). Complex reaction time tests were chosen in the expectation they would provide more insight into cognitive status than simple reaction time tests, while allowing frequent re-testing (without prominent training effect), as needed for this task, given the short average duration of seizures and of the study. Testing began no earlier than 24 hr after electrode implantation to allow for recovery from anesthesia and immediate postoperative pain/discomfort.

Test Description

Each subject received instructions as to how to take the test and had a training session that had to be successfully completed prior to the start of the trial. The complex reaction time (FIG. 7) consisted of the serial and simultaneous presentation of a pair of visual "stimuli" (the letter "A" and a square "☐"), displayed full screen simultaneously on a 15" monitor positioned at eye level, at a comfortable distance from the subject. The position of the letter on either half of the screen (i.e., left "A ☐", or right "☐ A"), was randomly chosen for each presentation and the subject was instructed to immediately press, upon appearance of each visual stimuli, either the left or right mouse button according to the side of the screen (left or right) on which the letter A appeared. As soon as the subject pressed either button, or after a maximal presentation time (1 s) had elapsed, in case of no response, each stimulus presentation was removed (resulting in a blank screen) until the next stimuli. At the end of each presentation, a random timer was set, the expiration of which would trigger the next presentation. A total of 36 stimuli were presented in each testing session. Inter-trial presentation time intervals were randomly chosen from the set {0.5, 1.0, 1.5, 2.0 s.} to minimize adaptation and better assess performance.

Timing of Complex Reaction Time Tests Administration

The Complex Reaction-time tests were triggered only between 08:00-20:00 daily, throughout the surgical monitoring period by: a) Seizures [via the earlier of real-time automated seizure detection (Osorio et al, 2002) or event button presses] and b) Randomly. The timer that triggered random complex reaction time tests was set for 6 presentations per day, uniformly distributed throughout the 12 hour test period, with the additional constraints that no random test could occur within the 15 minutes period after a seizure or a randomly triggered test. To minimize fatigue, no more than a total of 30 tests (random plus seizure-triggered) could be administered over any 12 hour period.

Whenever a complex reaction time test was triggered, a sound file consisting of a voice saying "Begin Test" was automatically played to summon the subject to take the test. The subject was instructed to, upon hearing the summon, press one of the mouse buttons to activate the test. The "summons" was repeated every 5 s unless the subject began the test, up to a total of 6 times (30 s), with the sound file volume increasing with each repetition. If the subject did not initiate the complex reaction time test after 30 s, this information was logged and the system would go dormant until the next test.

Seizures were detected and quantified (intensity, duration and extent of spread) with a validated algorithm (Osorio et al 2002), whose output was used to trigger the complex reaction time tests; most automated detections occurred within 5 s of electrographic onset as marked visually by independent experts (Osorio et al, 2002). The classification of complex reaction time tests as ictal or random/interictal was validated off-line via expert visual analysis of the ECoG segments associated with each test. Complex reaction time tests triggered by false positive detections and randomly-triggered tests that overlapped in time with true seizures not detected by the algorithm (false negatives) were reclassified accordingly.

Complex Reaction Time Data Recording and Processing

The following were recorded (with millisecond precision) and logged/saved to the computer's memory: a) Test condition (random vs. seizure); b) Summon times corresponding to each prompt to the subject to start the test; c) Latency of responses to summons; d) Stimuli presentation times and side of the screen (left vs. right) where the letter "A" was displayed; and e) Times and sides (left vs. right) of all button presses. These data were processed to derive the following measures for each subject: I. Compliance, defined as the fraction of presented stimuli within each testing session for which the subject pressed the button regardless of correctness (Compliance Score=#responses/#presentations). II. Percentage of correct responses=#correct responses/#presentations, where correct responses are defined as those for which the subject pressed only once the button ipsilateral to the side (left or right) of the screen where the letter "A" appeared. Responses were classified as incorrect if: a) The mouse button contralateral to where the letter "A" was displayed on the screen was pressed; b) The right and left mouse buttons were pressed simultaneously or sequentially; c) The correct button was pressed more than once per stimulus presentation; or d) No button was pressed; III. Time to impaired response (TIR): The time (in seconds) elapsed between each test summon and the last correct response prior to the first test failure as defined below. The mean, range and standard deviation (SD) of time to impaired response (TIR) was computed for three different definitions of test failure, from most to least stringent: A) A correct response but with latency exceeding the 90th percentile of those for random tests (TIR-A); speed of reaction is in certain situations as important as correctness of response; B) Any incorrect response as defined in II. above (TIR-B); C) Three consecutive incorrect responses, regardless of their response latencies (TIR-C), a definition that attempts to account for the fact that subjects make intermittent errors even during random tests when they presumably are not cognitively impaired. If no failure occurred in a test, the interval ends with the time of the correct response to the last stimuli. However, since assessment is limited to the duration (75 sec) of the complex reaction time test, the possibility of impairment after the test's termination cannot be excluded. Using the time to last correct response, not to the time to first failure (as defined above), overestimates time to impaired response (TIR), an approach deemed preferable/"safer" to underestimating it.

Subjects' data were included in the analyses only if: 1. The ECOG tracings were of sufficiently good quality to allow visual ascertainment of the presence or absence of seizures; and 2. There were at least two CRTs taken during random and at least one under seizure conditions.

ECOG Recording Processing and Analysis

ECOG was recorded using commercially available depth (mesial temporal regions) or grid/strip electrodes (cerebral convexities) electrodes (Ad-Tech, Racine, WI). These signals were fed into commercially available systems (Nicolet, Madison, WI), filtered (0.5-70 Hz; digitized (240 Hz, 10 bits of precision, 0.59 µV/bit) and further processed using a validated seizure detection and quantification algorithm (Osorio 1998, Osorio 2002) implemented into a custom bedside system (Peters et al., 2001). The detection algorithm quantified maximal seizure intensity (Si), duration (Sd); site(s) of seizure origin and extent of spread (Sc) were determined through visual review of ECOG. For this study, seizures were defined as any automated detection that reached an intensity threshold, $T=22$, for a minimum duration, $D=0.84$ s. with or without clinical manifestations. These parameters (T and D) were selected (Osorio et al, 98) to optimize sensitivity and specificity of the detection algorithm.

The relation between location and extent of the primary epileptogenic zone(s) and extent of seizure spread (outside the primary epileptogenic zone) and several complex reaction time performance measures (i.e. percent of correct responses; TIR, etc.) was probed. Seizure onset and spread were classified as follows: Focal: Ictal activity restricted to 2 contiguous electrode contacts; Regional: Ictal activity in 3 or more contiguous or non-contiguous contacts, provided the contacts are in the same region (i.e. left amygdala, pes and body of hippocampus); Lobar: Ictal activity in two or more regions within the same lobe (i.e., mesial temporal and neocortical temporal); Intrahemispheric: Ictal activity in two or more regions (in at least 2 different lobes) within the same hemisphere; Interhemispheric: Ictal activity in one or more regions (i.e. right and left mesial temporal regions) and Diffuse: Ictal activity in one or more lobes in each hemisphere.

In order to better understand the impact of seizure intensity (Si), duration (Sd) and extent of spread (Sc) on complex reaction time performance, the percentiles (p) of these three variables were conflated into one: Seizure Severity (SS)= $pSi+pSd+pSc/3$ (Osorio et al 2005) with one modification compared to the original one: using the classification defined above the following arbitrary values were assigned to it: Focal=1; Regional=2; Lobar=4; Intrahemispheric=8 and Interhemispheric=16. A scatter plot of seizure severity vs. percentage of correct response and time to impaired response (TIR) for each subject was generated and reviewed to assess the relationship between seizure severity and time to loss of function.

Data Processing Analyses

The data were analyzed for each as well as for all (pooled) subjects, where appropriate. Compliance, defined as the fraction of complex reaction time tests presented divided by those that were taken, was analyzed individually (as opposed to pooling the data from all subjects) since the data was skewed by one subject who was presented with 20 random tests and took 5 (25%) vs. 134 seizure tests of which 19 were taken (14%).

To provide additional insight and test for differences that might not be encompassed in an analysis of mean and SD alone, we analyzed the distributions of the various measures, comparing differences of random vs. seizure tests with the Kolmogorov-Smirnov test, a goodness of fit non-parametric test (Lindgren 1976). For each subject, the null hypothesis, namely, that the random and seizure tests performance are derived from the same distribution (i.e. they are not significantly ($p=<0.05$) different) was tested.

Since the deleterious impact of complex or secondarily generalized seizures on cognitive performance is cumulative, when closely spaced in time, all automated detections in a 15 minute window prior to each random or seizure test were annotated and taken into account in the interpretation of the complex reaction time test performance.

Results

Twenty subjects (See Table 1 for demographics, type, numbers and sites of electrode implantations and localization of the epileptogenic zone(s) all of which met the inclusion criteria, were enrolled in this study. The data from 6 subjects (4, 6, 7, 9, 12, 13) were excluded from analyses as they did not take the minimum required number of seizure-triggered tests. In 12/14 subjects electrographic onset preceded clinical seizure onset; in subjects 16 & 20 clinical preceded electrographic onset and their data was included in the analyses as control.

A total of 856 tests were administered: 649 (76%) were random with subjects responding to 520 (80%) and 207 (19%) were seizure-triggered (all true positive detections) with subjects responding to 73 (35%). These differences were primarily due to a few subjects who reported "getting tired" of taking large numbers of tests. The mean and SD of the average compliance scores for the 14 subjects included in the analyses were: Random tests: 0.91+/−0.12 vs. Seizure tests: 0.82+/−0.26, differences that were not statistically significant (paired t-test: p~0.14). The mean and SD of the average percentage of correct responses for the 14 subjects were: Random tests: 85+/−14% vs. Seizure tests: 76+/−30%, differences that were not statistically significant (paired t-test: p~0.15).

Mean maximal seizure intensity, duration and spread for each subject are shown in Table 3.

The mean, range and SD of time to failure (as defined above) for all subjects are shown in Table 4. Differences in means between seizure and random tests were significant for TIR-A (p~0.02) and TIR-B (p~0.04), but not for TIR-C (p~0.4).

For 3/14 subjects, the Kolmogorov-Smirnov test identified significant differences in certain distributions: In subject 5, TIR-A was longer (p~0.03) for seizures than for random tests; in subjects 8 & 11, the percentage of correct responses was higher (p~0.04) for seizures than for random tests; in subject 11, the SD of response times for seizures is larger (p~0.04) than for random tests.

The relationship between response delay and correctness of response to instantaneous seizure intensity (regardless of whether tests were triggered by seizure detection or by a random trigger; in the latter case, instantaneous seizure intensity was 0) was analyzed using scatter plots and classified into four groups: 1. As seizure intensity increased, response latency decreased, but without apparent impact on likelihood of correctness [Subject 14]; 2. As seizure intensity increased, response delay appeared unchanged, but with an increase in likelihood of an incorrect choice [Subjects 5, 16, and 20]; 3. As seizure intensity increased, response delay increased along with an increase in likelihood of an incorrect choice [Subjects 10 and 11]; and 4. As seizure intensity increased, there was no apparent change in either response delay or likelihood of an incorrect choice [Subjects 2, 17, and 19]. In the remaining five subjects, there was insufficient data at high intensities to identify any relationship between the variables [Subjects 1, 3, 8, 15, and 18].

Relative Seizure Severity (RSS) showed negative correlations between % correct and TIR-A,B,C with RSS for patients 2 (TIR-A), 3 (TIR-A,B), 4 (TIR-A,B,C), 5 (TIR-A,B), 6 (% corr, TIR-A,B,C), 7. % corr, TIR-A,B,C), 9 (TIR-A,B), 11 (TIR-A,B), 12 (TIR-A,B), and 13 (TIR-B).

DISCUSSION

This study employed automated seizure detection to trigger a complex reaction time test to estimate the length of time following automated seizure detection for which a subjects' performance is indistinguishable from interictal (non-seizure) periods. Reaction time is the time required for perceptual processing, evaluation of a stimulus and enactment of a response. Complex (also known as choice or alternative) reaction time, unlike simple reaction time tests, consists of more than one stimulus, adding complexity that increases with the logarithm of the stimuli number, thus probing thoroughly and in-depth a subject's ability to correctly and in a timely manner process and evaluate stimuli and generate an adaptive response. The process that takes place between the presentation of a stimulus and the response may be broken down into three subprocesses listed in order of occurrence: a) a stimulus registration time; b) a choice reaction time; and c) a time in constructing a decision to respond. This and the ability to re-administer it multiple times make complex reaction time tests suitable for assessing the impact of seizures on responsiveness/awareness.

The period (regardless of duration) after detection of seizure onset during which performance assessed with this complex reaction time test was indistinguishable from that obtained interictally, is referred herein to as Time to impaired response (TIR). It is inferred from these results that before impairment, subjects are able to acquire and correctly process sensory cues and integrate the elements required to generate an adaptive (appropriate) and timely response. The Time to Impaired Response obtained in this study, under adverse conditions (postoperatively and in an ICU environment), show that in subjects with seizures of mesial temporal origin (which are the majority in this cohort), the mean time to impaired response (TIR-A: 56.1 s; TIR-B: 27.1 s, and TIR-C: 42.8 s) was adequate for implementation/execution of certain behaviors, including but not limited to prevention of falls to the ground, other injuries, and even possibly disengagement from the operation of power equipment and of motor vehicles (Green, 2000). These findings justify the issuing of automated warning(s) (in addition to therapy) to decrease the risk of injuries and costs of care (both direct and indirect) and enhance the quality of life of subjects with seizures originating from certain brain regions. Due to the proclivity of seizures originating in the frontal lobe to rapidly evolve into complex or secondarily generalized ones and the susceptibility to dysfunction (even to single epileptiform discharges (Shewmon & Erwin I, II, 1988) of areas subserving vision, subjects with these epilepsies may not benefit from short-term warning.

That administration of the complex reaction time tests may have modified the probability of seizure occurrence, their expression, and severity is worth entertaining in light of two observations: 1. When compared with the 37 other subjects evaluated for epilepsy surgery during the same time period who were not enrolled in this study, those participating required significantly longer monitoring [by 2.2 days, 8.9 days for enrollees vs. 6.7 days for those not enrolled (p~0.04)] to capture 5 typical clinical seizures; 2. In one subject (#2) the intensity of seizures during which tests were administered was significantly lower (p<0.001) than those during which tests were not administered. A small body of literature (Efron 1957; Paulson 1963; Kuhlman 1978; Papini et al 1984; Pritchard et al, 1985; Fenwick 1991) provides examples of seizure abatement, using sensory or other forms of stimulation, and of the increased likelihood of seizures with decreased vigilance and cognitive activity, suggesting that seizures may be amenable to "cognitive" intervention.

As gleaned from these observations, the systematic study of certain aspects of behavior and cognition during the peri-ictus and ictus illuminated heretofore unknown aspects of the mind-seizure interactions, provided means to decrease the burden of epileptics and of their caregivers, and expanded the realm of activities safely open to epileptics.

REFERENCES

Block A, Fisher R S. Can patients perform volitional motor acts at the start of a seizure? J Clin Neurophysiol. 1999 March; 16(2):141-5.

Gotz-Trabert K, Hauck C, Wagner K, Fauser S, Schulze-Bonhage A. Spread of ictal activity in focal epilepsy. Epilepsia. 2008 September; 49(9):1594-601. Epub 2008 Apr. 24.

Quesney L F. Clinical and EEG features of complex partial seizures of temporal lobe origin. Epilepsia. 1986; 27 Suppl 2:S27-45.Links Zajdel R, Nowak D. Simple and complex reaction time measurement. Computers in Biology and Medicine 37 (12); 1724-30 2007

Shewmon D A, Erwin R J. The effect of focal interictal spikes on perception and reaction time. I. General considerations. Electroencephalogr Clin Neurophysiol. 1988 April; 69(4):319-37.

Shewmon D A, Erwin R J. The effect of focal interictal spikes on perception and reaction time. II. Neuroanatomic specificity. Electroencephalogr Clin Neurophysiol. 1988 April; 69(4):338-52.

Stern Y, Mayeux R, Cote L. Reaction time and vigilance in Parkinson's disease. Possible role of altered norepinephrine metabolism. Arch Neurol. 1984 October; 41(10):1086-9.

Arnsten A F, Li B M. Neurobiology of executive functions: catecholamine influences on prefrontal cortical functions. Biol Psychiatry. 2005 Jun. 1; 57(11):1377-84.

Li G Y, Ueki H, Kawashima T, Sugataka K, Muraoka T, Yamada S. Involvement of the noradrenergic system in performance on a continuous task requiring effortful attention. Neuropsychobiology. 2004; 50(4):336-40

Egelman D M, Person C, Montague P R. A computational role for dopamine delivery in human decision-making. J Cogn Neurosci. 1998 September; 10(5):623-30.

Berridge C W, Waterhouse B D. The locus coeruleus-noradrenergic system: modulation of behavioral state and state-dependent cognitive processes. Brain Res Brain Res Rev. 2003 April; 42(1):33-84.

Shouse M N, Staba R J, Ko P Y, Saquib S F, Farber P R. Monoamines and seizures: microdialysis findings in locus ceruleus and amygdala before and during amygdala kindling. Brain Res. 2001 Feb. 16; 892(1):176-92.

Hoshino O. Cognitive enhancement mediated through postsynaptic actions of norepinephrine on ongoing cortical activity. Neural Comput. 2005 August; 17(8):1739-75.

Giorgi F S, Blandini F, Cantafora E, Biagioni F, Armentero M T, Pasquali L, Orzi F, Murri L, Paparelli A, Fornai F. Activation of brain metabolism and fos during limbic seizures: the role of locus coeruleus. Neurobiol Dis. 2008 June; 30(3):388-99. Epub 2008 Mar. 6.

Rammsayer T. Is there a common dopaminergic basis of time perception and reaction time? Neuropsychobiology 1989; 21:37-42

Aston-Jones G, Chiang C, Alexinsky T. Discharge of noradrenergic locus coeruleus neurons in behaving rats and monkeys suggests a role in vigilance. Prog Brain Res. 1991; 88:501-20.

Aston-Jones G, Chiang C, Alexinsky T. Discharge of noradrenergic locus coeruleus neurons in behaving rats and monkeys suggests a role in vigilance. Prog Brain Res. 1991; 88:501-20.

Fenwick P. Evocation and inhibition of seizures. Behavioral treatment. Adv Neurol. 1991; 55:163-83

Kuhlman W N. EEG feedback training of epileptic patients: clinical and electroencephalographic analysis. Electroencephalogr Clin Neurophysiol. 1978 December; 45(6):699-710.

Pritchard P B, Holmstrom V L, Giacinto J. Self-abatement of complex partial seizures. Ann Neurol 1985; 18:265-267.

Papini M, Pasquinelli A, Armellini M, Orlandi D. Alertness and incidence of seizures in patients with Lennox-Gastaut syndrome. Epilepsia 1984; 52:161-167.

Paulson G W. Inhibition of seizures. Dis Nerv Syst 1963; 11:657-664.

Efron R. The conditioned inhibition of uncinate fits. Brain 1957; 80:251-262.

Lindgren B W. Statistical theory. 3rd ed. New York: Macmillan, 1976:494-5.

Peters T E, Bhavaraju N C, Frei M G, Osorio I., J Clin Neurophysiol. 2001 November; 18(6):545-9.

Osorio I, Frei M G, Giftakis J, Peters T, Ingram J, Turnbull M, Herzog M, Rise M T, Schaffner S, Wennberg R A, Walczak T S, Risinger M W, Ajmone-Marsan C. Epilepsia. 2002 December; 43(12):1522-35.

Osorio I, Frei M G, Sunderam S, Giftakis J, Bhavaraju N C, Schaffner S F, Wilkinson S B. Ann Neurol. 2005 February; 57(2):258-68.

Osorio I, Frei M G, Wilkinson S B. Epilepsia. 1998 June; 39(6):615-27.

Green M. How Long Does It Take To Stop?" Methodological Analysis of Driver Perception-Brake Times. Transportation Human Factors, 2000; 2:195-216.Begley, C. E., M. Famulari, J. F. Annegers, D. R. Lairson, T. F. Reynolds, S. Coan, S. Dubinsky, M. E. Newmark, C. Leibson, E. L. So and W. A. Rocca (2000). "The cost of epilepsy in the United States: an estimate from population-based clinical and survey data." Epilepsia 41(3): 342-51.

Kwan, P. and M. J. Brodie (2000). "Early identification of refractory epilepsy." New England Journal of Medicine 342(5): 314-9.

TABLE 1

| Subject | Site(s) of Origin | # of SZs | Spread |
|---|---|---|---|
| 01 | RMT focal | 1 | No |
| 02 | LMT focal | 19 | Regional |
| 03 | RTnC | 2 | Focal |
|  | RTnC regional |  | No |
| 05 | RMT focal | 2 | Regional |
| 08 | LMT focal | 111 | No |
|  | LMT regional | 8 | No |
|  | LMT focal | 2 | Interhemispheric |
| 10 | LMT regional | 7 | No |
| 11 | LMT regional | 2 | Intrahemispheric |
| 14 | Interhemispheric | 10 | No |
| 15 | R frontal regional | 9 | No |
|  | R frontal regional | 1 | Lobar |
| 16 | L frontal focal | 1 | Diffuse |
| 17 | RMT focal | 1 |  |
|  | RMT focal | 1 | Interhemispheric |
|  | RMT focal | 1 | No |
|  | RMT focal | 1 | Regional |
|  | LMT focal | 1 | Interhemispheric |
|  | RTM focal | 1 | No |
| 18 | LMT focal | 4 | Regional |
|  | LMT focal | 1 | No |
| 19 | RTM focal | 1 | No |
|  | RTM focal | 1 | Regional |
| 20 | RTM Regional | 1 | Interhemispheric |

L = Left; R = Right; M = Mesial; T = Temporal; nC = Neocortical

TABLE 2

| Subject No. | Age | Years with epilepsy | Gender | Etiology | Class | Monthly Baseline Frequency | Primary Epileptogenic Zone(s) | Electrode Type(s) & Approach |
|---|---|---|---|---|---|---|---|---|
| 1 | 32 | 27 | F | Cryptogenic | CP | 10 |  | Rt. Amygdala B.D.; Lat. |
| 2 | 30 | 29 | F | Cryptogenic | CP | 4 |  | Lt. Amygdala & Pes Hippocampus B.D.; Lat. |
| 3 | 34 | 22 | M | Infection | Sec. Gral. | 5 |  | Rt. Fronto-Temporal Convexity Grid |
| 4 | 22 | 4 | M | Trauma | Sec. Gral. | 5 |  | Rt. Hippocampus B.D.; Lat. |
| 5 | 11 | 4 | M | Cryptogenic | CP | 16 |  | Rt. Amygdala B.D.; Lat. |
| 6 | 30 | 23 | F | Congenital | CP | 10 |  | Rt. Amygdala & Hippocampus B.D.; Lat. |
| 7 | 42 | 14 | M | Trauma | Sec. Gral. | 7 |  | Rt. Frontal Convexity Grid |
| 8 | 23 | 23 | F | Cryptogenic | CP | N/A |  | Lt. Hippocampus B.D.; Lat. |
| 9 | 35 | 34 | F | Trauma | Sec. Gral. | 4 |  | Lt. Frontal Convexity Grid |
| 10 | 26 | 26 | M | Infection | CP | 15 |  | Left Amygdala & Hippocampus B.D.; Lat. |
| 11 | 48 | 38 | M | Cryptogenic | CP | 75 |  | Rt Amygdala B.D.; Lat. |

TABLE 2-continued

| Subject No. | Age | Years with epilepsy | Gender | Etiology | Class | Monthly Baseline | Frequency Zone(s) | Primary Epileptogenic Electrode Type(s) & Approach |
|---|---|---|---|---|---|---|---|---|
| 12 | 20 | 8 | M | Cryptogenic | CP | 2 | | Rt. Posterior Hippocampus B.D.; Lat. |
| 13 | 28 | 3 | M | Cryptogenic | CP | 45 | | Bi-occipital polar B.D. |
| 14 | 34 | 22 | F | Cryptogenic | CP | 3 | | Lt. Hippocampus; Rt. Amygdala B.D.; Lat. |
| 15 | 32 | 19 | M | Trauma | Sec. Gral. | 3 | | Rt. Frontal Convexity Grid |
| 16 | 22 | 21 | F | Cryptogenic | Sec. Gral. | 2 | | Rt. Post. Hippocampus; Lt. Post. Hippocampus; bi-Fronto-Polar B.D.; Strips |
| 17 | 19 | 11 | M | Cryptogenic | CP | 3 | | Lt. Hippocampus; Rt.Amygdala B.D.; Lat. |
| 18 | 21 | 17 | M | Trauma | CP | 4 | | Lt. Hippocampus B.D.; Lat. |
| 19 | 25 | 16 | F | Cryptogenic | Sec. Gral. | N/A | | Lt. Hippocampus B.D.; Lat. |
| 20 | 30 | 11 | M | Cryptogenic | CP | 16 | | Rt. Amygdala & Hippocampus B.D.; Lat. |

CP = Complex Partial; Sec. Gral. = Secondarily Generalized; B.D. = Bilateral Depth electrodes; Lat. = Lateral (Electrodes are inserted through the temporal bone)

TABLE 3

| Subject Seizures | Mean Maximal Intensity | Mean Duration (s) | Mean Spread |
|---|---|---|---|
| 01 | 17.7 | 4.0 | 1.0 |
| 02 | 124.8 | 28.9 | 2.0 |
| 03 | 5.5 | 34.0 | 1.5 |
| 05 | 306.5 | 17.1 | 2.0 |
| 08 | 94.6 | 6.4 | 1.3 |
| 10 | 247.0 | 22.6 | 2.0 |
| 11 | 607.1 | 79.4 | 8.0 |
| 14 | 128.8 | 16.7 | 16.0 |
| 15 | 165.3 | 4.9 | 2.2 |
| 16 | 1005.7 | 36.2 | 16.0 |
| 17 | 242.0 | 9.6 | 6.3 |
| 18 | 842.6 | 25.8 | 5.6 |
| 19 | 3.6 | 70.0 | 1.5 |
| 20 | 340.3 | 87.6 | 16.0 |

TABLE 4

| | Random Tests | | | Seizure Tests | | |
|---|---|---|---|---|---|---|
| | Mean (s) | SD (s) | Range (s) | Mean (s) | SD (s) | Range (s) |
| TIR-A | 22.0 | 17.3 | 0.2-83.5 | 27.1 | 19.8 | 0.6-75.0 |
| TIR-B | 37.2 | 25.0 | 0.2-92.0 | 42.8 | 24.2 | 0.6-82.2 |
| TIR-C | 55.5 | 24.8 | 2.0-103.0 | 56.1 | 23.9 | 0.6-88.7 |

TIR: Time to impaired response, with failure defined as: A. Either an incorrect response or a slow correct response (with latency exceeding the 90% tile of random test response latencies); B. Any incorrect response; C. Three consecutive incorrect responses All of the methods and apparatuses disclosed and claimed herein may be made and executed without undue experimentation in light of the present disclosure. While the methods and apparatus of this disclosure have been described in terms of particular embodiments, it will be apparent to those skilled in the art that variations may be applied to the methods and apparatus and in the steps, or in the sequence of steps, of the method described herein without departing from the concept, spirit, and scope of the disclosure, as defined by the appended claims. It should be especially apparent that the principles of the disclosure may be applied to selected cranial nerves other than, or in addition to, the vagus nerve to achieve particular results in treating patients having epilepsy, depression, or other medical conditions.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below.

In one embodiment, a method for determining a degree of responsiveness of a patient having brain state changes includes receiving an indication of a triggering event; administering to the patient, in response to the indication, a test of responsiveness; and/or determining, based upon a result of the test, at least one responsiveness parameter selected from the group consisting of (i) a time of occurrence of a change in the patient's responsiveness, (ii) a duration of a change in the patient's responsiveness; (iii) a magnitude of a change in the patient's responsiveness, (iv) a time interval from the indication of event occurrence to a change in the patient's responsiveness, (v) a type of change in the patient's responsiveness, (vi) an estimation of a seizure severity; (vii) a classification of a seizure into clinical or subclinical; (viii) a classification of a clinical seizure into simple partial, complex partial, or generalized; (ix) an assessment of efficacy of a therapy for the patient's medical condition; (x) an assessment of the state of the disease and formulation of a prognosis for the patient; (xi) an estimation of a risk of injury or death for the patient; and (xii) two or more thereof.

In another example, the triggering event is selected from the group consisting of a) an indication from a medical event detection algorithm that a medical event is occurring or is imminent; b) a manual signal to administer the responsiveness test to the patient; or c) a command to administer a responsiveness test to the patient in the absence of an indication from a medical event detection algorithm that a medical event is occurring or imminent.

In another example, the method may further include detecting a change in an autonomic index of the patient by analyzing at least one set of signals received from the patient and selected from the group consisting of cardiovascular signals, respiratory signals, skin signals, pupillary signals, temperature signals, peristaltic signals, autonomic nerve or ganglia signals, and two or more thereof. In addition, the method may further include detecting a change in a neurologic index of the patient by analyzing at least one set of signals received from the patient and selected from the group consisting of brain signals, cranial nerve signals, spinal cord signals, peripheral nerve signals, body kinetic, position and force signals, and two or more thereof. In addition, the patient may suffers from epilepsy, and administering is performed at a plurality of times, wherein at least one of the plurality of times is ictal and at least one of the plurality of times is nonictal. In addition, the method may further include selecting a first test of responsiveness having a first difficulty level, and, based on the patient's responsiveness according to the first test, selecting and administering a second test of responsiveness having a second difficulty level. In addition, the method may further include selecting a first test of responsiveness having a first duration, and, based on the patient's responsiveness according to the first test, selecting and administering a second test of responsiveness having a second duration. In addition, the test of responsiveness tests may be a patient's reflex, motor, and/or cognitive functions. In addition, the test of responsiveness tests is a cognitive function of the patient and the cognitive function may be selected from the group consisting of attention, verbal, non-verbal and procedural short-term memory, verbal, non-verbal and procedural long-term memory, language fluency and comprehension, visuo-spatial functions, auditory discrimination, visual discrimination, abstract reasoning, calculations, or two or more thereof. In addition, the method may further include delivering a therapy for a seizure event to the patient, wherein the therapy for the seizure event is selected from the group consisting of electrical stimulation of a cranial nerve of the patient, thermal manipulation of the cranial nerve of the patient, electrical stimulation of the brain of the patient, thermal manipulation of the brain of the patient, delivery of a chemical agent to the patient via the bloodstream, cerebrospinal fluid or directly into the brain, magnetic stimulation of a cranial nerve, magnetic stimulation of the brain a motor task, a perceptual task, a cognitive task, and two or more thereof. In addition, the method may further include based on the patient's responsiveness, instructing an external device to change an operating state thereof.

In another embodiment, a computer readable program storage unit encoded with instructions that, when executed by a computer, perform a method for determining a responsiveness of a patient having brain state changes including receiving an indication of a triggering event; administering to the patient, in response to the indication, a test of responsiveness; and/or determining, based upon a result of the test, at least one responsiveness parameter selected from the group consisting of (i) a time of occurrence of a change in the patient's responsiveness, (ii) a duration of a change in the patient's responsiveness; (iii) a magnitude of a change in the patient's responsiveness, (iv) a time interval from the indication of event occurrence to a change in the patient's responsiveness, (v) a type of change in the patient's responsiveness, (vi) an estimation of a seizure severity; (vii) a classification of a seizure into clinical or subclinical; (viii) a classification of a clinical seizure into simple partial, complex partial, or generalized; (ix) an assessment of efficacy of a therapy for the patient's medical condition; (x) an assessment of the state of the disease and formulation of a prognosis for the patient; (xi) an estimation of a risk of injury or death for the patient; and (xii) two or more thereof.

In addition, the triggering event is selected from the group consisting of a) an indication from a medical event detection algorithm that a medical event is occurring or is imminent; b) a manual signal to administer the responsiveness test to the patient; and/or c) a command to administer a responsiveness test to the patient in the absence of an indication from a medical event detection algorithm that a medical event is occurring or imminent. In addition, the method may further include detecting a change in an autonomic index of the patient by analyzing at least one set of signals received from the patient and selected from the group consisting of cardiovascular signals, respiratory signals, skin signals, pupillary signals, temperature signals, peristaltic signals, autonomic nerve or ganglia signals, and two or more thereof. In addition, the method may further include detecting a change in a neurologic index of the patient by analyzing at least one set of signals received from the patient and selected from the group consisting of brain signals, cranial nerve signals, spinal cord signals, peripheral nerve signals, body kinetic, position and force signals, and two or more thereof. In addition, the patient suffers from epilepsy, and administering is performed at a plurality of times, wherein at least at least one of the plurality of times is ictal and at least one of the plurality of times is nonictal. In addition, the method may include selecting a first test of responsiveness having a first difficulty level, and, based on the patient's responsiveness according to the first test, selecting and/or administering a second test of responsiveness having a second difficulty level. In addition, the method may include selecting a first test of responsiveness having a first duration, and, based on the patient's responsiveness according to the first test, selecting and/or administering a second test of responsiveness having a second duration. In addition, the test of responsiveness tests at least one of the patient's reflex, motor, and/or cognitive functions. In addition, the test of responsiveness tests a cognitive function of the patient, wherein the cognitive function is selected from the group consisting of attention, verbal, non-verbal and procedural short-term memory, verbal, non-verbal and procedural long-term memory, language fluency and comprehension, visuo-spatial functions, auditory discrimination, visual discrimination, abstract reasoning, calculations, or two or more thereof. In addition, the method may include delivering a therapy for a seizure event to the patient, wherein the therapy for the seizure event is selected from the group consisting of electrical stimulation of a cranial nerve of the patient, thermal manipulation of the cranial nerve of the patient, electrical stimulation of the brain of the patient, thermal manipulation of the brain of the patient, delivery of a chemical agent to the patient via the bloodstream, cerebrospinal fluid or directly into the brain, magnetic stimulation of a cranial nerve, magnetic stimulation of the brain a motor task, a perceptual task, a cognitive task, and two or more thereof.

In another embodiment, a medical device system for determining a responsiveness of a patient having brain state changes may include a receiving unit adapted to receive an indication of a triggering event; a responsiveness testing unit adapted to administer a test of responsiveness to a patient in response to the indication; and/or a determination unit adapted to receive a result of the test and to make at least one determination selected from the group consisting of (i) a time of occurrence of a change in the patient's responsiveness, (ii) a duration of a change in the patient's responsiveness; (iii) a magnitude of a change in the patient's responsiveness, (iv) a time interval from the indication of event occurrence to a change in the patient's responsiveness, (v) a type of change in the patient's responsiveness, (vi) an estimation of a seizure severity; (vii) a classification of a seizure into clinical or subclinical; (viii) a classification of a clinical seizure into simple partial, complex partial, or generalized; (ix) an assessment of efficacy of a therapy for the patient's medical condition; (x) an assessment of the state of the disease and formulation of a prognosis for the patient; (xi) an estimation of a risk of injury or death for the patient; and (xii) two or more thereof.

In addition, the medical device system may include a storage unit adapted to store at least one of the test result or the determination; an autonomic or neurologic index change detection unit adapted to detect a change in an autonomic or neurologic index of the patient; a medical event therapy unit adapted to deliver a therapy for a medical event to the patient; and/or a responsiveness test selection unit adapted to select at least one of a plurality of tests of responsiveness and instruct the responsiveness testing unit to administer the selected test.

In addition, a method for determining a degree of responsiveness of a patient having brain state changes may include receiving an indication of a triggering event; administering to the patient, in response to the indication, a test of responsiveness; and/or determining, based upon a result of the test, at least one responsiveness parameter selected from the group consisting of (i) a time of occurrence of a change in the patient's responsiveness, (ii) a duration of a change in the patient's responsiveness; (iii) a magnitude of a change in the patient's responsiveness, (iv) a time interval from the indication of event occurrence to a change in the patient's responsiveness, (v) a type of change in the patient's responsiveness, (vi) an estimation of a seizure severity; (vii) a classification of a seizure into clinical or subclinical; (viii) a classification of a clinical seizure into simple partial, complex partial, or generalized; (ix) an assessment of efficacy of a therapy for the patient's medical condition; (x) an assessment of the state of the disease and formulation of a prognosis for the patient; (xi) an estimation of a risk of injury or death for the patient; and (xii) two or more thereof.

In addition, a computer readable program storage unit encoded with instructions that, when executed by a computer, perform a method for determining a degree of responsiveness of a patient having brain state changes may include receiving an indication of a triggering event; administering to the patient, in response to the indication, a test of responsiveness; and/or determining, based upon a result of the test, at least one responsiveness parameter selected from the group consisting of (i) a time of occurrence of a change in the patient's responsiveness, (ii) a duration of a change in the patient's responsiveness; (iii) a magnitude of a change in the patient's responsiveness, (iv) a time interval from the indication of event occurrence to a change in the patient's responsiveness, (v) a type of change in the patient's responsiveness, (vi) an estimation of a seizure severity; (vii) a classification of a seizure into clinical or subclinical; (viii) a classification of a clinical seizure into simple partial, complex partial, or generalized; (ix) an assessment of efficacy of a therapy for the patient's medical condition; (x) an assessment of the state of the disease and formulation of a prognosis for the patient; (xi) an estimation of a risk of injury or death for the patient; and (xii) two or more thereof.

In addition, a method of determining a responsiveness of a patient having brain state changes, comprising receiving an indication of a triggering event; administering to the patient, in response to the indication, a test of responsiveness; determining, based upon a result of the test, at least one responsiveness parameter selected from the group consisting of (i) a time of occurrence of a change in the patient's responsiveness, (ii) a duration of a change in the patient's responsiveness; (iii) a magnitude of a change in the patient's responsiveness, (iv) a time interval from the indication of event occurrence to a change in the patient's responsiveness, (v) a type of change in the patient's responsiveness, (vi) an estimation of a seizure severity; (vii) a classification of a seizure into clinical or subclinical; (viii) a classification of a clinical seizure into simple partial, complex partial, or generalized; (ix) an assessment of efficacy of a therapy for the patient's medical condition; (x) an assessment of the state of the disease and formulation of a prognosis for the patient; (xi) an estimation of a risk of injury or death for the patient; and (xii) two or more thereof. A medical device system capable of implementing the method.

What is claimed:

1. A method of treating a medical condition in a patient using an implantable medical device, the implantable medical device including a first electrode coupled to a first cranial nerve structure and a second electrode coupled to a second cranial nerve structure, the method comprising:
   providing a first electrical signal to the first cranial nerve structure of the patient;
   providing a second electrical signal to the second cranial nerve structure of the patient;
   administering to the patient a responsiveness test and comparing a result of the responsiveness test to a baseline responsiveness test; and
   initiating a second therapy or issuing a warning based on the comparison of the result of the responsiveness test to the baseline responsiveness test;
   wherein at least one responsiveness parameter includes at least one of: (i) a duration of a change in the patient's responsiveness; (ii) a magnitude of a change in the patient's responsiveness, (iii) a time interval from an indication of the detection of the epileptic seizure to a change in the patient's responsiveness, (iv) a type of change in the patient's responsiveness, (v) an estimation of a seizure severity; (vi) a classification of a seizure into clinical or subclinical; (vii) a classification of a clinical seizure into simple partial, complex partial, or generalized; (viii) an assessment of efficacy of a therapy for the patient's medical condition; (ix) an assessment of the state of the disease and formulation of a prognosis for the patient; (x) an estimation of a risk of injury or death for the patient; and (xi) two or more thereof.

2. The method of claim 1, wherein one or more processors are configured to increase a sympathetic tone to increase a heart rate of the patient via at least one of the second therapy and a third therapy.

3. The method of claim 1, wherein one or more processors are configured to decrease a parasympathetic tone to increase a heart rate of the patient via at least one of the second therapy and a third therapy.

4. The method of claim 1, wherein one or more processors are configured to decrease a sympathetic tone to decrease a heart rate of the patient via at least one of the second therapy and a third therapy.

5. The method of claim 1, wherein one or more processors are configured to increase a parasympathetic tone to decrease a heart rate of the patient via at least one of the second therapy and a third therapy.

6. The method of claim 1, further comprising a seizure detection unit capable of analyzing at least one body data stream to determine an epileptic seizure status.

7. A method of treating a medical condition in a patient using an implantable medical device, the implantable medical device including a first electrode coupled to a first cranial nerve structure and a second electrode coupled to a second cranial nerve structure, the method comprising:
   providing a first electrical signal to the first cranial nerve structure of the patient;
   providing a second electrical signal to the second cranial nerve structure of the patient;
   administering to the patient a responsiveness test and comparing a result of the responsiveness test to a baseline responsiveness test;
   initiating a second therapy or issuing a warning based on the comparison of the result of the responsiveness test to the baseline responsiveness test;
   collecting body data of the patient by at least one of an electrocardiography (EKG) device, an accelerometer, an inclinometer, a pupillometer, a face or body temperature monitor, a skin resistance monitor, a sound sensor, or a pressure sensor;
   determining an autonomic index; and
   detecting a change in the autonomic index of the patient by analyzing at least one set of signals received from the patient and selected from a signal group consisting of cardiovascular signals, respiratory signals, skin signals, pupillary signals, temperature signals, peristaltic signals, autonomic nerve or ganglia signals, and two or more thereof.

8. The method of claim 1, further comprising:
   collecting body data of the patient by at least one of an electrocardiography (EKG) device, an accelerometer, an inclinometer, a pupillometer, a face or body temperature monitor, a skin resistance monitor, a sound sensor, or a pressure sensor;
   determining an autonomic index; and
   detecting a change in a neurologic index of the patient by analyzing at least one set of signals received from the patient and selected from a signal group consisting of brain signals, cranial nerve signals, spinal cord signals, peripheral nerve signals, body kinetic, position and force signals, and two or more thereof.

9. The method of claim 1, wherein the responsiveness test includes a first test of responsiveness having a first difficulty level, and, based on the patient's responsiveness according to the first test, selecting and administering a second test of responsiveness having a second difficulty level.

10. The method of claim 1, wherein the responsiveness test includes a first test of responsiveness having a first duration, and, based on the patient's responsiveness according to the first test, selecting and administering a second test of responsiveness having a second duration.

11. A method of treating a medical condition in a patient using an implantable medical device, the implantable medical device including a first electrode coupled to a first cranial nerve structure and a second electrode coupled to a second cranial nerve structure, the method comprising:
   providing a first electrical signal to the first cranial nerve structure of the patient;
   providing a second electrical signal to the second cranial nerve structure of the patient;
   administering to the patient a responsiveness test and comparing a result of the responsiveness test to a baseline responsiveness test; and
   initiating a second therapy or issuing a warning based on the comparison of the result of the responsiveness test to the baseline responsiveness test;
   wherein the test of responsiveness tests a cognitive function of the patient, wherein the cognitive function is selected from a cognitive function group consisting of: an attention; a reaction time; a verbal, a non-verbal and a procedural short-term memory; a verbal, a non-verbal and a procedural long-term memory; a language fluency and comprehension; a visuo-spatial functions; an auditory discrimination; a visual discrimination; an abstract reasoning; calculations; or two or more thereof.

12. The method of claim 1, further comprising, based on the patient's responsiveness, instructing an external device to change an operating state thereof.

13. The method of claim 1, wherein the test of responsiveness further comprises a test to determine a patient's capacity to perform the response.

14. The method of claim 1, wherein the test of responsiveness includes testing at least one of a reflex, a motor, or cognitive functions of the patient.

* * * * *